United States Patent
Dubensky, Jr. et al.

(10) Patent No.: US 9,895,435 B2
(45) Date of Patent: *Feb. 20, 2018

(54) VACCINES FOR HSV-2

(71) Applicant: IMMUNE DESIGN CORP., Seattle, WA (US)

(72) Inventors: Thomas W. Dubensky, Jr., Seattle, WA (US); Nancy A. Hosken, Seattle, WA (US); Scott H. Robbins, Seattle, WA (US); Margaret D. Moore, Seattle, WA (US)

(73) Assignee: IMMUNE DESIGN CORP., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/895,858

(22) Filed: May 16, 2013

(65) Prior Publication Data

US 2014/0127247 A1 May 8, 2014

Related U.S. Application Data

(60) Provisional application No. 61/647,764, filed on May 16, 2012, provisional application No. 61/679,387, filed on Aug. 3, 2012, provisional application No. 61/714,158, filed on Oct. 15, 2012.

(51) Int. Cl.
| | |
|---|---|
| *A61K 39/245* | (2006.01) |
| *A61K 39/12* | (2006.01) |
| *C07K 14/005* | (2006.01) |
| *A61K 39/00* | (2006.01) |
| *A61K 38/00* | (2006.01) |

(52) U.S. Cl.
CPC ............ *A61K 39/245* (2013.01); *A61K 39/12* (2013.01); *C07K 14/005* (2013.01); *A61K 38/00* (2013.01); *A61K 2039/545* (2013.01); *A61K 2039/55572* (2013.01); *C12N 2710/16622* (2013.01); *C12N 2710/16634* (2013.01)

(58) Field of Classification Search
CPC .. C07K 14/005; A61K 39/12; A61K 2300/00; A61K 39/00; A61K 2039/53; A61K 39/245; A61K 35/763; A61K 2039/55583; A61K 47/4833; A61K 38/162; C12N 2710/16634; C12N 7/00; C12N 2710/16622; C12N 15/86; C12N 2710/16632; C12N 2710/16643; C12N 15/63; C12N 2710/16034
See application file for complete search history.

(56) References Cited

U.S. PATENT DOCUMENTS

| | | | |
|---|---|---|---|
| 3,238,190 A | 3/1966 | Erbring et al. |
| 3,598,122 A | 8/1971 | Zaffaroni |
| 3,598,123 A | 8/1971 | Zaffaroni |
| 4,029,762 A | 6/1977 | Galanos et al. |
| 4,286,592 A | 9/1981 | Chandrasekaran |
| 4,314,557 A | 2/1982 | Chandrasekaran |
| 4,379,454 A | 4/1983 | Campbell et al. |
| 4,420,461 A | 12/1983 | Reckel et al. |
| 4,420,558 A | 12/1983 | De Mey et al. |
| 4,568,343 A | 2/1986 | Leeper et al. |
| 4,595,654 A | 6/1986 | Reckel et al. |
| 4,614,722 A | 9/1986 | Pasula |
| 4,629,722 A | 12/1986 | Ribi |
| 4,659,659 A | 4/1987 | Dwek et al. |
| 4,709,011 A | 11/1987 | Cohen et al. |
| 4,743,540 A | 5/1988 | Ralph et al. |
| 4,762,708 A | 8/1988 | Cohen et al. |
| 4,767,402 A | 8/1988 | Kost et al. |
| 4,769,330 A | 9/1988 | Paoletti et al. |
| 4,780,212 A | 10/1988 | Kost et al. |
| 4,818,694 A | 4/1989 | Watson et al. |
| 4,844,894 A | 7/1989 | Ribi |
| 4,866,034 A | 9/1989 | Ribi |
| 4,891,315 A | 1/1990 | Watson et al. |
| 4,897,268 A | 1/1990 | Tice et al. |
| 4,912,094 A | 3/1990 | Myers et al. |
| 4,948,587 A | 8/1990 | Kost et al. |
| 4,981,684 A | 1/1991 | MacKenzie et al. |
| 4,987,237 A | 1/1991 | Myers et al. |
| 5,017,487 A | 5/1991 | Stunnenberg et al. |
| 5,057,540 A | 10/1991 | Kensil et al. |
| 5,075,109 A | 12/1991 | Tice et al. |

(Continued)

FOREIGN PATENT DOCUMENTS

| | | |
|---|---|---|
| DE | 3833319 A1 | 4/1989 |
| EP | 0109942 B1 | 5/1984 |

(Continued)

OTHER PUBLICATIONS

Bowman BR, Baker ML, Rixon FJ, Chiu W, Quiocho FA. Structure of the herpesvirus major capsid protein. EMBO J. Feb. 17, 2003;22(4):757-65.*

Huang CJ, Wagner EK. The herpes simplex virus type 1 major capsid protein (VP5-UL19) promoter contains two cis-acting elements influencing late expression. J Virol. Sep. 1994;68(9):5738-47.*

Desai P, Person S. Second site mutations in the N-terminus of the major capsid protein (VP5) overcome a block at the maturation cleavage site of the capsid scaffold proteins of herpes simplex virus type 1. Virology. Sep. 1, 1999;261(2):357-66.*

(Continued)

*Primary Examiner* — Rachel B Gill
(74) *Attorney, Agent, or Firm* — Marshall, Gerstein & Borun LLP

(57) ABSTRACT

Compositions of recombinant HSV-2 proteins and an agonist of the innate immune system, such as an adjuvant, are provided as a vaccine. Proteins include an envelope glycoprotein and a structural protein other than an envelope glycoprotein, e.g., a capsid or tegument protein. The vaccine is for use in either HSV-2 seropositive or seronegative subjects.

14 Claims, 18 Drawing Sheets

(56) References Cited

U.S. PATENT DOCUMENTS

| | | |
|---|---|---|
| 5,124,141 A | 6/1992 | Makler |
| 5,147,785 A | 9/1992 | Pasula |
| 5,149,259 A | 9/1992 | Greco |
| 5,149,532 A | 9/1992 | Brunell |
| 5,162,990 A | 11/1992 | Odeyale et al. |
| 5,171,568 A | 12/1992 | Burke et al. |
| 5,231,168 A | 7/1993 | Dziegiel et al. |
| 5,278,302 A | 1/1994 | Caruthers et al. |
| 5,298,396 A | 3/1994 | Kotzin et al. |
| 5,411,865 A | 5/1995 | Reed |
| 5,422,109 A | 6/1995 | Brancq et al. |
| 5,424,067 A | 6/1995 | Brancq et al. |
| 5,457,041 A | 10/1995 | Ginaven et al. |
| 5,464,387 A | 11/1995 | Haak et al. |
| 5,530,113 A | 6/1996 | Christ et al. |
| 5,565,209 A | 10/1996 | Rijke |
| 5,591,139 A | 1/1997 | Lin et al. |
| 5,595,888 A | 1/1997 | Gray et al. |
| 5,612,041 A | 3/1997 | Burke et al. |
| 5,612,476 A | 3/1997 | Christ et al. |
| 5,618,275 A | 4/1997 | Bock |
| 5,650,155 A | 7/1997 | Cornelius et al. |
| 5,654,140 A | 8/1997 | Persico et al. |
| 5,656,016 A | 8/1997 | Ogden |
| 5,666,153 A | 9/1997 | Copeland |
| 5,667,784 A | 9/1997 | Cornelius et al. |
| 5,693,531 A | 12/1997 | Chiorini et al. |
| 5,709,860 A | 1/1998 | Raychaudhuri et al. |
| 5,709,879 A | 1/1998 | Barchfeld et al. |
| 5,718,904 A | 2/1998 | Hjorth |
| 5,719,263 A | 2/1998 | Reed |
| 5,722,397 A | 3/1998 | Eppstein |
| 5,747,039 A | 5/1998 | Burke et al. |
| 5,756,718 A | 5/1998 | Christ et al. |
| 5,776,468 A | 7/1998 | Hauser et al. |
| 5,786,148 A | 7/1998 | Bandman et al. |
| 5,795,577 A | 8/1998 | Kieny et al. |
| 5,837,260 A | 11/1998 | Cohen et al. |
| 5,840,871 A | 11/1998 | Hillman et al. |
| 5,843,464 A | 12/1998 | Bakaletz et al. |
| 5,843,918 A | 12/1998 | Christ et al. |
| 5,846,758 A | 12/1998 | Medenica |
| 5,851,533 A | 12/1998 | Berman et al. |
| 5,885,211 A | 3/1999 | Eppstein et al. |
| 5,888,519 A | 3/1999 | Alving |
| 5,912,166 A | 6/1999 | Reed et al. |
| 5,952,309 A | 9/1999 | Rossignol et al. |
| 5,955,306 A | 9/1999 | Gimeno et al. |
| 5,961,970 A | 10/1999 | Lowell et al. |
| 5,976,538 A | 11/1999 | Hilgers et al. |
| 5,981,215 A | 11/1999 | Meissner et al. |
| 5,993,800 A | 11/1999 | Linsley et al. |
| 6,005,099 A | 12/1999 | Davies et al. |
| 6,018,678 A | 1/2000 | Mitragotri et al. |
| 6,027,730 A | 2/2000 | Francotte et al. |
| 6,027,732 A | 2/2000 | Morein et al. |
| 6,033,928 A | 3/2000 | Eriguchi et al. |
| 6,057,427 A | 5/2000 | Smith et al. |
| 6,106,824 A | 8/2000 | Kaplitt et al. |
| 6,120,769 A | 9/2000 | Gefter et al. |
| 6,146,632 A | 11/2000 | Momin et al. |
| 6,212,102 B1 | 4/2001 | Georgakos et al. |
| 6,218,186 B1 | 4/2001 | Choi et al. |
| 6,231,861 B1 | 5/2001 | Barnwell |
| 6,235,724 B1 | 5/2001 | Asai et al. |
| 6,261,762 B1 | 7/2001 | Alizon et al. |
| 6,270,769 B1 | 8/2001 | Raychaudhuri et al. |
| 6,309,847 B1 | 10/2001 | Cohen et al. |
| 6,316,183 B1 | 11/2001 | Alizon et al. |
| 6,322,532 B1 | 11/2001 | D'Sa et al. |
| 6,375,944 B1 | 4/2002 | Trinchieri et al. |
| 6,413,518 B1 | 7/2002 | Koelle et al. |
| 6,451,325 B1 | 9/2002 | Van Nest et al. |
| 6,472,515 B1 | 10/2002 | Climent-Johansson et al. |
| 6,488,936 B1 | 12/2002 | Mishkin et al. |
| 6,491,919 B2 | 12/2002 | Crane |
| 6,512,102 B1 | 1/2003 | Xu et al. |
| 6,544,518 B1 | 4/2003 | Friede et al. |
| 6,544,728 B1 | 4/2003 | Alizon et al. |
| 6,555,653 B2 | 4/2003 | Alderson et al. |
| 6,572,861 B1 | 6/2003 | Roberts et al. |
| 6,587,792 B1 | 7/2003 | Thomas |
| 6,596,501 B2 | 7/2003 | Roth |
| 6,613,892 B2 | 9/2003 | Preston et al. |
| 6,630,161 B1 | 10/2003 | Leesman |
| 6,654,462 B1 | 11/2003 | Hedberg |
| 6,660,487 B2 | 12/2003 | Faustman |
| 6,676,961 B1 | 1/2004 | Lichter |
| 6,682,901 B2 | 1/2004 | Blaschuk et al. |
| 6,683,063 B2 | 1/2004 | Rossignol et al. |
| 6,685,699 B1 | 2/2004 | Eppstein et al. |
| 6,692,752 B1 | 2/2004 | Slaoui et al. |
| 6,706,872 B1 | 3/2004 | Barnwell |
| 6,713,068 B1 | 3/2004 | Audonnet et al. |
| 6,733,763 B2 | 5/2004 | Raychaudhuri et al. |
| 6,734,172 B2 | 5/2004 | Scholler et al. |
| 6,749,856 B1 | 6/2004 | Berzofsky et al. |
| 6,752,995 B2 | 6/2004 | Johnston et al. |
| 6,770,445 B1 | 8/2004 | Scholler et al. |
| 6,783,981 B1 | 8/2004 | Uden et al. |
| 6,797,276 B1 | 9/2004 | Glenn et al. |
| 6,814,969 B2 | 11/2004 | Koelle et al. |
| 6,821,519 B2 | 11/2004 | Day et al. |
| 6,828,155 B1 | 12/2004 | Kaneko et al. |
| 6,844,192 B2 | 1/2005 | Orlando et al. |
| 6,846,489 B1 | 1/2005 | Garcon et al. |
| 6,846,648 B2 | 1/2005 | Maes |
| 6,855,322 B2 | 2/2005 | Lyon et al. |
| 6,869,607 B1 | 3/2005 | Buschle et al. |
| 6,871,477 B1 | 3/2005 | Tucker |
| 6,875,610 B2 | 4/2005 | Higginbotham et al. |
| 6,893,820 B1 | 5/2005 | Plass |
| 6,908,453 B2 | 6/2005 | Fleming et al. |
| 6,911,434 B2 | 6/2005 | Baldridge et al. |
| 6,919,078 B2 | 7/2005 | Ni et al. |
| 6,919,210 B1 | 7/2005 | Okamoto |
| 6,929,796 B1 | 8/2005 | Conti-Fine |
| 6,932,972 B2 | 8/2005 | Stephenne et al. |
| 6,933,123 B2 | 8/2005 | Hu et al. |
| 6,936,255 B1 | 8/2005 | Wettendorff |
| 6,949,246 B2 | 9/2005 | Reed et al. |
| 6,969,704 B1 | 11/2005 | Pinsky et al. |
| 6,970,739 B1 | 11/2005 | Inoue |
| 6,974,588 B1 | 12/2005 | Miranda et al. |
| 6,977,073 B1 | 12/2005 | Cezayirli et al. |
| 6,979,535 B2 | 12/2005 | Alizon et al. |
| 6,979,730 B2 | 12/2005 | Reiter et al. |
| 6,991,791 B2 | 1/2006 | Le et al. |
| 7,001,770 B1 | 2/2006 | Atencio et al. |
| 7,008,774 B2 | 3/2006 | Ryan et al. |
| 7,012,134 B2 | 3/2006 | Ruben et al. |
| 7,018,345 B2 | 3/2006 | Mori et al. |
| 7,029,678 B2 | 4/2006 | Momin et al. |
| 7,029,685 B2 | 4/2006 | Lanar et al. |
| 7,030,232 B1 | 4/2006 | Reiter et al. |
| 7,033,598 B2 | 4/2006 | Lerner |
| 7,037,712 B2 | 5/2006 | Both et al. |
| 7,052,904 B2 | 5/2006 | Zheng et al. |
| 7,060,276 B2 | 6/2006 | Lanar et al. |
| 7,060,802 B1 | 6/2006 | Trakht et al. |
| 7,067,310 B2 | 6/2006 | Chartier et al. |
| 7,070,931 B2 | 7/2006 | Fujinaga et al. |
| 7,078,041 B2 | 7/2006 | Koelle et al. |
| 7,078,180 B2 | 7/2006 | Genetta |
| 7,084,256 B2 | 8/2006 | McCormick et al. |
| 7,087,231 B2 | 8/2006 | Guerin-Marchand et al. |
| 7,094,767 B2 | 8/2006 | Armstrong et al. |
| 7,264,817 B1 | 9/2007 | Berman et al. |
| 7,357,936 B1 | 4/2008 | Garcon |
| 7,666,434 B2 | 2/2010 | Koelle et al. |
| 7,744,899 B2 | 6/2010 | Whitley et al. |
| 7,744,903 B2 | 6/2010 | Koelle et al. |
| 7,820,627 B2 | 10/2010 | Jiang et al. |
| 8,067,010 B2 | 11/2011 | Koelle et al. |

(56) References Cited

U.S. PATENT DOCUMENTS

| | | | |
|---|---|---|---|
| 8,575,070 B2 * | 11/2013 | Watt et al. .................. 506/25 |
| 8,617,564 B2 | 12/2013 | Long et al. |
| 9,241,988 B2 | 1/2016 | Shaw et al. |
| 2002/0176867 A1 | 11/2002 | Andersen et al. |
| 2003/0068327 A1 * | 4/2003 | Hosken et al. ............ 424/186.1 |
| 2003/0118611 A1 * | 6/2003 | Koelle et al. ............. 424/231.1 |
| 2003/0165512 A1 | 9/2003 | Wheeler et al. |
| 2003/0165819 A1 * | 9/2003 | McGowan et al. ............... 435/5 |
| 2003/0165820 A1 * | 9/2003 | Day et al. ........................ 435/5 |
| 2003/0170249 A1 | 9/2003 | Hakomori et al. |
| 2003/0194391 A1 | 10/2003 | Ashman et al. |
| 2003/0215497 A1 | 11/2003 | Leesman |
| 2004/0120924 A1 | 6/2004 | Hone et al. |
| 2004/0161776 A1 | 8/2004 | Maddon et al. |
| 2005/0123550 A1 | 6/2005 | Laurent et al. |
| 2005/0130132 A1 * | 6/2005 | Day et al. ........................ 435/5 |
| 2005/0244419 A1 | 11/2005 | Tosi et al. |
| 2007/0072824 A1 | 3/2007 | Kawano et al. |
| 2008/0081768 A1 * | 4/2008 | Watt et al. ..................... 506/9 |
| 2008/0131466 A1 | 6/2008 | Reed et al. |
| 2008/0299140 A1 | 12/2008 | Georges et al. |
| 2009/0181078 A1 * | 7/2009 | Reed et al. .................... 424/450 |
| 2010/0160419 A1 | 6/2010 | Vilalta et al. |
| 2010/0310602 A1 | 12/2010 | Reed et al. |
| 2010/0330112 A1 | 12/2010 | Long et al. |
| 2011/0014274 A1 | 1/2011 | Reed et al. |
| 2011/0070290 A1 | 3/2011 | Reed et al. |
| 2012/0027789 A1 * | 2/2012 | Corey ............... A61K 39/245 424/186.1 |
| 2012/0039994 A1 | 2/2012 | Reed et al. |
| 2012/0263754 A1 * | 10/2012 | Dubensky et al. ....... 424/204.1 |
| 2012/0288515 A1 * | 11/2012 | Robbins et al. .......... 424/186.1 |
| 2012/0328655 A1 * | 12/2012 | Dubensky, Jr. .... A61K 39/0011 424/231.1 |
| 2013/0224236 A1 * | 8/2013 | Koelle et al. ............. 424/186.1 |
| 2014/0086947 A1 * | 3/2014 | Dubensky et al. ....... 424/186.1 |
| 2014/0127247 A1 * | 5/2014 | Dubensky et al. ....... 424/186.1 |
| 2014/0128268 A1 * | 5/2014 | Watt et al. ........................ 506/2 |
| 2014/0193460 A1 * | 7/2014 | Spector et al. ............ 424/231.1 |
| 2014/0227307 A1 * | 8/2014 | Long et al. ................ 424/186.1 |
| 2014/0328870 A1 * | 11/2014 | Long et al. ................ 424/186.1 |

FOREIGN PATENT DOCUMENTS

| | | | |
|---|---|---|---|
| EP | 0198474 A1 | 10/1986 |
| EP | 0224260 A2 | 6/1987 |
| EP | 0304578 A1 | 3/1989 |
| EP | 0324455 A2 | 7/1989 |
| EP | 0362279 A1 | 4/1990 |
| EP | 0366412 A2 | 5/1990 |
| EP | 0382271 A1 | 8/1990 |
| EP | 0414374 A2 | 2/1991 |
| EP | 0468520 A2 | 1/1992 |
| EP | 0729473 A1 | 9/1996 |
| EP | 0761231 A1 | 3/1997 |
| EP | 2068918 B1 | 5/2012 |
| GB | 2220211 A | 1/1990 |
| GB | 2232892 A | 1/1991 |
| JP | 63010728 A | 1/1988 |
| JP | 07055906 A | 3/1995 |
| JP | 10131046 A | 5/1998 |
| WO | WO-1989/001973 A2 | 3/1989 |
| WO | WO-1990/001496 A1 | 2/1990 |
| WO | WO-1990/006951 A1 | 6/1990 |
| WO | WO-1990/007936 A1 | 7/1990 |
| WO | WO-1991/000106 A1 | 1/1991 |
| WO | WO-1991/000107 A1 | 1/1991 |
| WO | WO-1991/002805 A2 | 3/1991 |
| WO | WO-1993/002184 A1 | 2/1993 |
| WO | WO-1993/010152 A1 | 5/1993 |
| WO | WO-1993/012778 A1 | 7/1993 |
| WO | WO-1993/025234 A1 | 12/1993 |
| WO | WO-1993/025698 A1 | 12/1993 |
| WO | WO-1994/000152 A1 | 1/1994 |
| WO | WO-1994/000153 A1 | 1/1994 |
| WO | WO-1994/003622 A1 | 2/1994 |
| WO | WO-1994/005792 A1 | 3/1994 |
| WO | WO-1994/020137 A1 | 9/1994 |
| WO | WO-1994/021292 A1 | 9/1994 |
| WO | WO-1995/014026 A1 | 5/1995 |
| WO | WO-1995/017209 A1 | 6/1995 |
| WO | WO-1995/017210 A1 | 6/1995 |
| WO | WO-1995/18148 A1 | 7/1995 |
| WO | WO-1995/020600 A1 | 8/1995 |
| WO | WO-1995/026204 A1 | 10/1995 |
| WO | WO-1996/002555 A1 | 2/1996 |
| WO | WO-1996/009310 A1 | 3/1996 |
| WO | WO-1996/011272 A2 | 4/1996 |
| WO | WO-1996/011711 A1 | 4/1996 |
| WO | WO-1996/026277 A1 | 8/1996 |
| WO | WO-1996/033739 A1 | 10/1996 |
| WO | WO-1997/011708 A1 | 4/1997 |
| WO | WO-1997/042947 A1 | 11/1997 |
| WO | WO-1998/001139 A1 | 1/1998 |
| WO | WO-1998/012302 A1 | 3/1998 |
| WO | WO-1998/016247 A1 | 4/1998 |
| WO | WO-1998/20016 A1 | 5/1998 |
| WO | WO-1998/020117 A1 | 5/1998 |
| WO | WO 9820016 A1 * | 5/1998 | ........... C07K 14/005 |
| WO | WO-1998/037418 A2 | 8/1998 |
| WO | WO-1998/043670 A2 | 10/1998 |
| WO | WO-1998/056414 A1 | 12/1998 |
| WO | WO-1998/058956 A2 | 12/1998 |
| WO | WO-1999/003884 A2 | 1/1999 |
| WO | WO-1999/010375 A2 | 3/1999 |
| WO | WO-1999/011241 A1 | 3/1999 |
| WO | WO-1999/012565 A1 | 3/1999 |
| WO | WO-1999/017741 A1 | 4/1999 |
| WO | WO-1999/028475 A2 | 6/1999 |
| WO | WO-1999/040188 A2 | 8/1999 |
| WO | WO-1999/051748 A2 | 10/1999 |
| WO | WO-1999/053061 A2 | 10/1999 |
| WO | WO-2000/004149 A2 | 1/2000 |
| WO | WO-2000/013029 A1 | 3/2000 |
| WO | WO-2000/018929 A2 | 4/2000 |
| WO | WO-2000/025815 A1 | 5/2000 |
| WO | WO-2000/042994 A2 | 7/2000 |
| WO | WO-2001/036433 A2 | 5/2001 |
| WO | WO-2001/090129 A2 | 11/2001 |
| WO | WO-2002/016560 A1 | 2/2002 |
| WO | WO-2002/028424 A2 | 4/2002 |
| WO | WO-2002/032450 A2 | 4/2002 |
| WO | WO-2002/032454 A1 | 4/2002 |
| WO | WO-03/086308 A2 | 10/2003 |
| WO | WO-2003/094850 A2 | 11/2003 |
| WO | WO-2005/014036 A1 | 2/2005 |
| WO | WO-2006/055729 A1 | 5/2006 |
| WO | WO-2007/097923 A2 | 8/2007 |
| WO | WO-2008/153541 A1 | 12/2008 |
| WO | WO-2009/143457 A2 | 11/2009 |
| WO | WO-2010/115172 A2 | 10/2010 |
| WO | WO-2010/141861 A1 | 12/2010 |
| WO | WO-2013/006569 A2 | 1/2013 |

OTHER PUBLICATIONS

Coler RN, Bertholet S, Moutaftsi M, Guderian JA, Windish HP, Baldwin SL, Laughlin EM, Duthie MS, Fox CB, Carter D, Friede M, Vedvick TS, Reed SG. Development and characterization of synthetic glucopyranosyl lipid adjuvant system as a vaccine adjuvant. PLoS One. Jan. 26, 2011;6(1):e16333.*

McGeoch DJ, Moss HW, McNab D, Frame MC. Major capsid protein UniProtKB/Swiss-Prot: P89442. Dep. Jun. 1, 2003.*

Ali et al., Characterization of an essential HSV-1 protein encoded by the UL25 gene reported to be involved in virus penetration and capsid assembly, Virol., 216(1):278-83 (1996).

Awasthi et al., Better neutralization of herpes simplex virus type 1 (HSV-1) than HSV-2 by antibody from recipients of GlaxoSmithKline HSV-2 glycoprotein D2 subunit vaccine, J. Infect. Dis., 210(4):571-5 (2014).

Awasthi et al., Immunization with a vaccine combining herpes simplex virus 2 (HSV-2) glycoprotein C (gC) and gD subunits

(56) References Cited

OTHER PUBLICATIONS improves the protection of dorsal root ganglia in mice and reduces the frequency of recurrent vaginal shedding of HSV-2 DNA in guinea pigs compared to immunization with gD alone, *J. Virol.*, 85(20):10472-86 (2011).
Awasthi et al., Status of prophylactic and therapeutic genital herpes vaccines, *Curr. Opin. Virol.*, 6:6-12 (2014).
Belshe et al., Efficacy results of a trial of a herpes simplex vaccine, *N. Engl. J. Med.*, 366(1):34-43 (2012).
Bernstein et al., Safety and immunogenicity of glycoprotein D-adjuvant genital herpes vaccine, *Clin. Infect. Dis.*, 40(9):1271-81 (2005).
Berstein et al., Potent adjuvant activity of cationic liposome-DNA complexes for genital herpes vaccines, *Clin. Vacc. Immunol.*, 16(5):699-705 (2009).
Blaho et al., An amino acid sequence shared by the herpes simplex virus 1 alpha regulatory proteins 0, 4, 22, and 27 predicts the nucleotidylylation of the UL21, UL31, UL47, and UL49 gene products, *J. Biol. Chem.*, 269(26):17401-10 (1994).
Bowman et al., Structural characterization of the UL25 DNA-packaging protein from herpes simplex virus type 1, *J. Virol.*, 80(5):2309-17 (2006).
Cattamanchi et al., Phase I study of a herpes simplex virus type 2 (HSV-2) DNA vaccine administered to healthy, HSV-2-seronegative adults by a needle-free injection system, *Clin. Vaccine Immunol.*, 15(11):1638-43 (2008).
Chentoufi et al., HLA-A Restricted CD+ Cytotoxic T Lymphocyte Epitopes Identified From Herpes Simplex Virus Glycoprotein D, *J. Immunol.*, 180:426-37 (2008).
Chiu et al., Effects of herpes simplex virus amplicon transduction on murine dendritic cells, *Hum. Gene Ther.* 20(5):442-52 (2009).
Cockrell et al., Role of the UL25 protein in herpes simplex virus DNA encapsidation, *J. Virol.*, 83(1):47-57 (2009).
Cohen et al., Structural analysis of the capsid polypeptides of herpes simplex virus types 1 and 2, *J. Virol.*, 34:521-31 (1980).
Coler et al., A Synthetic Adjuvant to Enhance and Expand Immune Responses to Influenza Vaccines, *PLoS One*, 5(10):e13677 (2010).
Corey et al., Recombinant glycoprotein vaccine for the prevention of genital HSV-2 infection: two randomized controlled trials. Chiron HSV Vaccine Study Group, *JAMA*, 282(4):331-40 (1999).
Dolan et al., The genome sequence herpes simplex virus type 2, *J. Virol.*, 72(3):2010-21 (1998).
Gebhardt et al., Memory T cells in nonlymphoid tissue that provide enhanced local immunity during infection with herpes simplex virus, *Nat. Immunol.*,10(5):524-30 (2009).
Hoshino et al., Protection from herpes simplex virus (HSV)-2 infection with replication-defective HSV-2 or glycoprotein D2 vaccines in HSV-1-seropositive and HSV-1-seronegative guinea pigs, *J. Infect. Dis.*, 200(7):1088-95 (2009).
Hosken et al., Diversity of the CD8+ T-cell response to herpes simplex virus type 2 proteins among persons with genital herpes, *J. Virol.*, 80(11):5509-15 (2006).
Hosken, Development of a therapeutic vaccine for HSV-2, *Vaccine*, 2395-8 (2005).
Ikeda et al., Antiherpes activity of chemically synthesized lipid A-subunit analogue GLA-60 in immunosuppressed mice, *Antiviral Research*, 11(4):173-180 (1989).
Kask et al., DNA vaccine delivery by densely-packed and short microprojection arrays to skin protects against vaginal HSV-2 challenge, *Vaccine*, 28:7483-91 (2010).
Khodai et al., Single and combination herpes simplex virus type 2 glycoprotein vaccines adjuvanted with CpG oligodeoxynucleotides or monophosphoryl lipid A exhibit differential immunity that is not correlated to protection in animal models, *Clin. Vaccine Immunol.*,18(10):1702-9 (2011).
Koelle et al., CD4 T-cell responses to herpes simplex virus type 2 major capsid protein VP5: comparison with responses to tegument and envelope glycoproteins, *J. Virol.*, 74(23):11422-5 (2000).

Koelle et al., CD8 CTL from genital herpes simplex lesions: recognition of viral tegument and immediate early proteins and lysis of infected cutaneous cell, *J. Immunol.*, 166(6):4049-58 (2001).
Koelle et al., Herpes simplex virus infection of human fibroblasts and keratinocytes inhibits recognition by cloned CD8+ cytotoxic T lymphocytes, *J. Clin. Invest.*, 91(3):961-8 (1993).
Koelle et al., Immunodominance among herpes simplex virus-specific CD8 T cells expressing a tissue-specific homing receptor, *Proc. Natl. Acad. Sci. USA*, 100(22):12899-904 (2003).
Koelle et al., Phase I dose-escalation study of a monovalent heat shock protein 70-herpes simplex virus type 2 (HSV-2) peptide-based vaccine designed to prime or boost CD8 T-cell responses in HSV-naïve and HSV-2-infected subjects, *Clin. Vaccine Immunol.*, 15(5):773-82 (2008).
Koelle et al., Recent progress in Herpes Simplex Virus Immunobiology and Vaccine Research, *Clin. Microbiol. Rev.*, 16(1):96-113 (2003).
Koelle et al., Tegument-specific, virus-reactive CD4 T cells localize to the cornea in herpes simplex virus interstitial keratitis in humans, *J. Virol.*, 74(23):10930-8 (2000).
Laing et al., Diversity in CD8(+) T cell function and epitope breadth among persons with genital herpes, *J. Clin. Immunol.*, 30(5):703-722 (2010).
Langenberg et al., A recombinant glycoprotein vaccine for herpes simplex virus type 2: safety and immunogenicity, *Ann. Intern. Med.*, 122(12):889-98 (1995).
Long et al., Identification of novel virus-specific antigens by $CD4^+$ and $CD8^+$ T cells from asymptomatic HSV-2 seropositive and seronegative donors, *Virol.*, 464-5:296-311 (2014).
Morello et al., Immunization with herpes simplex virus 2 (HSV-2) genes plus inactivated HSV-2 is highly protective against acute and recurrent HSV-2 disease, *J. Virol.*, 85(7):3461-72 (2011).
Morello et al., Inactivated HSV-2 in MPL/alum adjuvant provides nearly complete protection against genital infection and shedding following long term challenge and rechallenge, *Vaccine*, 30(46):6541-50 (2012).
Muller et al., Herpes simplex virus type 2 tegument proteins contain subdominant T-cell epitopes detectable in BALB/c mice after DNA immunization and infection, *J. Gen. Virol.*, 90(Pt 5):1153-60 (2009).
NCBI Genbank Reference Sequence: NP_044488.1; Major capsid Protein [Human herpesvirus 2]. Sub. Aug. 1, 2000; last revision Apr. 23, 2010.
Nishimura et al., Intraepithelial gammadelta T cells may bridge a gap between innate immunity and acquired immunity to herpes simplex virus type 2, *J. Virol.*, 78(9):4927-30 (2004).
Posavad et al., Detailed characterization of T cell responses to herpes simplex virus-2 in immune seronegative persons, *J. Immunol.*, 184(6):3250-9 (2010).
Posavad et al., Development of an interferon-gamma ELISPOT assay to detect human T cell responses to HSV-2, *Vaccine*, 29(40):7058-66 (2011).
Preston et al., The UL25 gene product of herpes simplex virus type 1 is involved in uncoating of the viral genome, *J. Virol.*, 82(13):6654-66 (2008).
Rajcani et al., Developments in herpes simplex virus vaccines: old problems and new challenges, *Folia Microbiol.*, 51(2):67-85 (2006).
Roth et al., HSV-2 vaccine: current state and insights into development of a vaccine that targets genital mucosal protection, *Microb. Pathog.*, 59:45-54 (2012).
Samandary et al., Associations of HLA-A, HLA-B and HLA-C alleles frequency with prevalence of herpes simplex virus infections and diseases across global populations: implication for the development of an universal CD8+ T-cell epitope-based vaccine, *Hum. Immunol.*, 75(8):715-29 (2014).
Sciortino et al., Of the three tegument proteins that package mRNA in herpes simplex virions, one (VP22) transports the mRNA to uninfected cells for expression prior to viral infection, *Proc. Natl. Acad. Sci. U.S.A.*, 99(12):8318-23 (2002).
Shlapobersky et al., Vaxfectin-adjuvanted plasmid DNA vaccine improves protection and immunogenicity in a murine model of genital herpes infection, *J. Gen. Virol.*, 9(Pt 6):1305-15 (2012).

(56) References Cited

OTHER PUBLICATIONS

Stanberry et al., Vaccination with recombinant herpes simplex virus glycoproteins: protection against initial and recurrent genital herpes. *J. Infect. Dis.*, 155:914-20 (1987).
Straus et al., Immunotherapy of recurrent genital herpes with recombinant herpes simplex virus type 2 glycoproteins D and B: results of a placebo-controlled vaccine trial, *J. Infect. Dis.*, 176(5):1129-34 (1997).
Tatman et al., Assembly of herpes simplex type 1 capsids using a panel of recombinant baculoviruses, *J. Gen. Virol.*, 75:1011-13 (1994).
Tigges et al., Human CD8+ herpes simplex virus-specific cytotoxic T-lymphocyte clones recognize diverse virion protein antigens, *J. Virol.*, 66(3):1622-34 (1992).
Tirabassi et al., A muscosal vaccination approach for herpes simplex virus type 2, *Vaccine*, 29:1090-8 (2011).
Verhagen et al., Nucleocytoplasmic shuttling of bovine herpesvirus 1 UL47 protein in infected cells, *J. Virol.*, 80(2):1059-63 (2006).
Wald et al., Safety and immunogenicity of long HSV-2 peptides complexed with rhHsc70 in HSV-2 seropositive persons, *Vaccine*, 29(47):8520-9 (2011).
Wang et al., The 2.2-kilobase latency-associated transcript of herpes simplex virus type 2 does not modulate viral replication, reactivation, or establishment of latency in transgenic mice, *J. Virol.*, 75(17):8166-72 (2001).
Zhang et al., A herpes simplex virus 2 (HSV-2) glycoprotein D-expressing nonreplicating dominant-negative HSV-2 virus vaccine is superior to a gD2 subunit vaccine against HSV-2 genital infection in guinea pigs, *PLoS one*, 9(6):e101373 (2014).
Zhu et al., Virus-specific CD8+ T cells accumulate near sensory nerve endings in genital skin during subclinical HSV-2 reactivation, *J. Exp. Med.*, 204(3):595-603 (2007).
Akamatsu et al., Synthesis of lipid A monosaccharide analogues containing acidic amino acid: Exploring the structural basis for the endotoxic and antagonistic activities, Bioorganic & Medicinal Chemistry, 14:6759-77 (2006).
Akamizu et al., molecular analysis of stimulatory anti-thyrotropin receptor antibodies (TSAbs) involved in Graves' Disease, J. Immunol., 157(7):3148-52 (1996).
Alexander et al., Bacterial lipopolysaccharides and innate immunity, J. Endotoxin Research, 7(3):167-202 (2001).
Alving et al., Lipid A and liposomes containing lipid A as antigens and adjuvants, Vaccine, 26:3036-45 (2008).
Alving, Lipopolysaccharide, Lipid A, and Liposomes Containing Lipid A as Immunologic Adjuvants, Immunobiol., 187:430-46 (1993).
Alving. et al., Liposomes containing lipid A: An effective, safe, generic adjuvant system for synthetic vaccines, Exp. Revs., 11(6):733-44 (2012).
American Thoracic Society, Standards for the diagnosis and care of patients with Chronic Obstructive Pulmonary Disease, Am. J. Respir. Crit. Care Med., 152(5 Pt 2):577-S121 (1995).
Andaloussi et al., Stimulation of TLR9 with CpG ODN enhances apoptosis of glioma and prolongs the survival of mice with experimental brain tumors, Glia, 54(6):526-35 (2006).
Apicella et al., Antigenic heterogeneity of lipid A of *Haemophilus imfluenzae*, Infect. Immun., 50:9-14 (1985).
Armant et al., Toll-like Receptors: a family of pattern-recognition receptors in mammals, Genome Biol., 3(8):3011.1-.6 (2002).
Asai, Development of an injectable formulation for the novel Lipid A analog E5531 using a 'pH-jump method, Yakugaku Zasshi, 24(12):965-72 (2004).
Avanti Polar Lipids, Certificate of Analysis #770030—Monophosphoryl Lipid A (Synthetic cGMP) Dated Jan. 15, 2008.
Avanti Polar Lipids, Inc., Product Data Sheet for Avanti Product No. 699200, Lipid A—Purified Detoxified Lipid A, http://www.avantilipds.com, download date Jan. 14, 2009.
Avanti Polar Lipids, Inc., Product Data Sheet for Avanti Product No. 699800, Lipid(Synthetic)(PHADTM) Monophosphoryl Lipid A (Synthetic)(PHADTM), http://www.avantilipds.com, download date Jan. 14, 2009.
Avanti, Advertising: Synthetic Adjuvant, J. Immunol., [Online] 178(10):1-5, May 15, 2007; XP002546530.
Avanti, Advertising: The New PHAD(tm) in vaccine technology Avanti's Synthetic Vaccine Adjuvant, J. Immunol., [Online] 179(12): 1-6, Dec. 15, 2007; XP002546531.
Badaro et al., Evaluation of micro enzyme-linked Immunosorbent Assay (ELISA) for antibodies in American Visceral Leishmaniasis: antigen selection for detection of infection-specific responses, Am. J. Trop. Med. Hyg., 35:72-8 (1986).
Badaro et al., rK39: A cloned antigen of Leishmania Chagasi that predicts active visceral leishmaniasis, J. Inf. Dis., 173(3):758-61 (1996).
Bainbridge et al., Expression of a *Porphyromonas gingivalis* lipid A palmitylacyl transferase in *Escherichia coli* yields a chimeric lipid A with altered ability to stimulate interleukin-8 secretion, *Cellular Microbiol.*, 8(1):120-9 (2006).
Baldridge et al., Monophosphoryl lipid A (MPL) formulations for the next generation of vaccines, *Methods*, 19:103-7 (1999).
Baldridge et al., Monophosphoryl lipid A enhances mucosol and systemic immunity to vaccine antigens following intranasal administration, Vaccine, 18:2416-25 (2000).
Baldridge et al., Taking a Toll on Human Disease: Toll-like receptor 4 agonists as vaccine adjuvants and monotherapeutic agents, *Expert Opin. Biol. Ther.*, 4(7):1129-38 (2004).
Bayes et al., Gateways to clinical trials, Methods Find Exp. Clin. Pharmacol., 27(3):193-219 (2005).
Berkner, Development of adenovirus vectors for the expression of heterologous genes, *Biotechniques*, 6(7):616-27 (1988).
Bertholet et al., Optimized subunit vaccine protects against experimental *leishmaniasis*, Vaccine, 27(50):7036-45 (2009).
Beutler et al., Cachectin and tumour necrosis factor as two sides of the same biological coin, Nature, 320:584-8 (1986).
Bhatia et al., Pilot Trial of Intratumoral G100, A toll-like Receptor-4 (TLR4) Agonist, In Patients with Merkel Cell Carcinoma: Final Clinical Results and Immunological Effects on the Tumor Microenviroment, cited as document D69 in Opposition against European Patent No. 2068918, dated Aug. 30, 2016.
Biological Tests, 151 Pyrogen Test (2016), cited as document D63d in Opposition against European Patent No. 2068918, Aug. 30, 2016.
Bomford et al., Adjuvanticity and ISCOM formation by structurally diverse saponins, Vaccine, 10(9):572-7 (1992).
Borges et al., Potent Stimulation of the Innate Immune System by a *Leishmania brasiliensis* Recombinant Protein, *Infection Immunity*, 69(9):5270-7 (2001).
Bortolatto et al., Toll-Like receptor 4 agonists adsorbed to aluminium hydroxide adjuvant attenuate ovalbumin-specific allergic airway disease: Role of MyD88 adaptor molecule and interleukin-12/interferon-y axis, *Clin. Exper. Allergy*, 38:1668-79 (2008).
Brade et al., Immunogenicity and antigenicity of synthetic *Escherichia coli* Lipid A, Infect. Immunity, 51(1):110-4 (1986).
Brade et al., The Immunogenicity and Antigenicity of Lipid A are influenced by its physicochemical state and environment, *Infect. Immunity*, 55(11):2636-44 (1987).
Brandenberg, Fourier transform infrared spectroscopy characterization of the lamellar and nonlamellar structures of free lipid A and Re lipopolysaccharides from Salmonella Minnesota and *Escherichia coli*, Bioohys. J., 64:1215-31 (1993).
Brandenburg et al., Conformational studies of synthetic lipid A analogues and partial structures by infrared spectroscopy, Biochimica et Biophysica Acta, 1329:183-201 (1997).
Brandenburg et al., Endotoxins: relationships between structure, function, and activity, *Current Topics in Medicinal Chemistry*, 4(11):1127-46 (2004).
Brandenburg et al., Physicochemical characteristics of triacyl lipid A partial structure OM-174 in relation to biological activity, *Eur. J. Biochem.*, 267:3370-7 (2000).
Bray et al., The immunology and serology of leishmaniasis. iv. result of ouchterlony double diffusion tests, Trans. R. Soc. Trop. Med. Hyg., 60(5):605-9 (1966).

(56) References Cited

OTHER PUBLICATIONS

Brazolot et al., CpG DNA can induce strong Th1 humoral and cell mediated immune responses against hepatitis B surface antigen in young mice, *Proc. Natl. Acad. Sci. USA*, 95(26):15553-8 (1998).
Bulusu et al., Acyclic analogs of lipid A: synthesis and biological activities, J. Med. Chem., 35(19):3463-9 (1992).
Burrell, Immunomodulation by bacterial endotoxin, Microbiology, 17(3):189-208 (1990).
Cady et al., Somnogenic activities of synthetic Lipid A, *Infect. Immunity*, 57(2):396-403 (1989).
Campagnari et al., Role of lipooligosaccharides in experimental dermal lesions caused by *Haemophilus ducreyi, Infect. Immun.*, 59:2601-8 (1991).
Casale et al., Safety of the intranasal toll-like receptor 4 agonist CRX-675 in allergic rhinitis, *Asthma & Immunology*, 97(4):454-6 (2006).
Chase et al., Effect of monophosphoryl lipid A on host resistance to bacterial infection, Infect. Immun., 53(3):711 (19896).
Chen et al., Distinct responses of lung and spleen dendritic cells to the TLR9 Against CpG oligodeoxynucleotide, J. Immunol., 177(4):2373-83 (2006).
Choudhary et al., An Indirect Fluorescent Antibody (IFA) test for the serodiagnosis of Kala-Azar, J. Comm. Dis., 24(1):32-6 (1992).
Choudhary et al., Enzyme-linked immunosorbent assay in the diagnosis of Kala-azar in Bhadohi (Varanasi), India, Trans. R. Soc. Trop. Med. Hyg., 84(3):363-6 (1990).
Ciprandi et al., Emerging anti-inflammatory agents for allergic rhinitis, Expert Opinion on Emerging Drugs, 10(4):689-705 (2005).
Coler et al., Immunization with a polyprotein vaccine consisting of the t-cell antigens thiol-specific antioxidant, leishmania major stress-inducible protein 1, and leishmania elongation initiation factor protects against leishmaniasis, *Infect. Immunity*, 70(8):4215-25 (2002).
Compendial Pyrogen Test at Charles River, France—Evaluation at CLPR Group (Research Center Borstel (RCB)) Table 1a .Summary of results according to specifications of European, US and Japanese Pharmacopoeias and Table 1b. Rating according to 1)Tmax and 2) momo-or biphasic form of fever curves (CLPR_RBC: Prof Ernest Ritschel, cited as document D63b in Opposition against European Patent No. 2068918, dated Aug. 30, 2016.
Cooper et al., CPG 7909 Adjuvant improves Hepatitis B virus vaccine seroprotection in antiretroviral-treated HIV-infected adults, AIDS, 19(14):1473-9 (2005).
Correale et al., In vitro generation of human cytotoxic t lymphocytes specific for peptides derived from prostate-specific antigen, J. National Cancer Institute, 89(4):293-300 (1997).
Cotten et al., High-efficiency receptor-mediated delivery of small and large (48 Kilobase Gene Constructs Using the Endosome-Disruption Activity of Defective or Chemically Inactivated Adenovirus Particles), *Proc. Natl. Acad. Sci. USA*, 89(13):6094-8 (1992).
Curiel et al., High efficiency gene transfer mediated by adenovirus coupled to DNA-polylysine complexes, Hum. Gene Ther., 3(2):147-54 (1992).
Darveau et al., Lipid A diversity and the innate host response to bacterial infection, Current Opinion in Microbiology, 1:36-42 (1998).
Datta et al., A Subset of Toll-Like Receptor ligands induces cross-presentation by bone marrow-derived dendritic cells, J. Immunol., 170(8):4102-10 (2003).
Davis et al., CpG DNA is a potent enhancer of specific immunity in mice immunized with recombinant Hepatitis B surface antigen, J. Immunol., 160(2):870-6 (1998).
Declaration of Dr. David T. Hickman submitted in support of opposition of European Patent No. EP-2068918 B1, dated Jan. 31, 2013.
Declaration of Dr. Maria Pilar Lopez-Deber submitted in support of opposition of European Patent No. EP-2068918 B1, dated Jan. 31, 2013.

Deng et al., CpG oligodeoxynucleotides stimulate protective innate immunity against pulmonary klebsiella infection, J. Immunol., 173:5148-55 (2004).
Diks et al., LPS signal transduction: The picture is becoming more complex, Curr. Topics Med. Chem., 4:1115-26 (2004).
Dixon et al., Lipopolysaccharide heterogeneity: Innate host responses to bacterial modification of Lipid A structure, J. Dent Res., 84(7):584-95 (2005).
Edelman, The development and use of vaccine adjuvants, *Mol. Biotechnol.*, 21(2):129-48 (2002).
Edelman, Vaccine adjuvants, Rev. Infect. Dis., 2(3):370-83 (1980).
El-On et al., Leishmania Donovani: Physicochemical, immunological, and biological characterization of excreted factor from promastigotes, Exper. Parasitol., 47(2):254-69 (1979).
European Application No. 07 875 082.5, Office Action dated Feb. 2, 2010.
European Pharmacopoeia, 2.6.8 Pyrogens 5923 (2016), cited as documents D63e in Opposition against European Patent No. 2068918, dated Aug. 30, 2016.
Experimental Report, Antitumor Activity study of MDR1 vaccines in a model of P388/ ADR tumor bearing B6D2F/J Mice, 1 (2006), cited as documents D66 in Opposition against European Patent No. 2068918, dated Aug. 30, 2016.
Falloon et al., A phase 1a, first-in-human, randomized study of a respiratory syncytial virus F protein vaccine with and without a toll-like receptor-4 agonist and stable emulsion adjuvant, *Vaccine*, 34(25):2847-54 (2016).
Fearon et al., The instructive role of innate immunity in the acquired immune response, Science, 272(5258):50-4 (1996).
Felgner et al., Lipofection: A highly efficient, lipid-mediated DNA-transfection procedure, *Proc. Natl. Acad. Sci. USA*, 84(21):7413-7 (1987).
Feuillet et al., Involvement of toll-like receptor 5 in the recognition of flagellated bacteria, *Proc. Natl. Acad. Sci. USA*, 103(33):12487-92 (2006).
Flad et al., Interleukin 1 and tumor necrosis factor: Studies on the induction by lipopolysaccharide partial structures, *Lymphokine Research*, 8(3) (1989).
Flesher et al., Characterization of lipopolysaccharide of *Haemophilus influenzae, J. Infect. Dis.*, 138:719-30 (1978).
Fujimoto et al., Synthesis of lipid A and its analogues for investigation of the structural basis for their bioactivity, J. Endotoxin Research, 11(6):341-7 (2005).
Fukuoka, et al., Structural characterization of lipid A component of Erwinia carotovora lipopolysaccharide, Arch Microbiol., 157:311-8 (1992).
Funatogawa et al., Relationship of structure and biological activity of monosaccharide lipid A analogues to induction of nitric oxide production by murine macrophase RAW264.7 cells, *Infect. Immun.*, 5792-8 (1998).
Galanos et al., Endotoxic properties of chemically synthesized lipid A part structures, Eur. J. Biochem., 140:221-7 (1984).
Galanos et al., Synthetic and natural *Escherichia coli* free lipid A express identical endotoxic activities, *Eur. J. Biochem.*, 148:1-5 (1985).
Garcon et al., The safety evaluation of adjuvants during vaccine development: The AS04 experience, *Vaccine*, 29:4453-9 (2011).
Garcon, Preclinical development of A504, *Methods in Molecular Biology*, 626:15-27 (2010).
Garidel et al., Divalent cations affect chain mobility and aggregate structure of lipopolysaccharide from Salmonella minnesota reflected in a decrease of its biological activity, Biochimica et Biophysica Acta, 17:122-31 (2005).
Gatouillat et al., Immunization with lipsome-anchored pegylated peptides modulates doxorubicin sensitivity in P-glycoprotein-expressing P388 cells. Can. Let., 257:165-71 (2007).
General Tests: Microbial Limit Test, 4.04 Pyrogen Test, 103, cited as document D63f in Opposition against European Patent No. 2068918, dated Aug. 30, 2016.
Gibson et al., Plasmacytoid dendritic cells produce cytokines and mature in response to the TLR7 agonists, imiquimod and resiquimod, Cell. Immunol., 218(1-2):74-86 (2002).

(56) References Cited

OTHER PUBLICATIONS

Gisvold, Digitonin and phytosterol from the seed of digitalis purpurea, Phytochem. Notes, Amer. Pharmacol. Assoc., 23(7):664-6 (1934).
Gluck, Immunopotentiating Reconstituted Influenza Virosomes (IRIVs) and other adjuvants for improved presentation of small antigens, Vaccine, 10(13):915-9 (1992).
Goldman, Translational mini-review series on toll-like receptors: Toll-like receptor ligands as novel pharmaceuticals for allergic disorders, Clin. Exper. Immunol., 147:208-16 (2007).
Gorden et al., Synthetic TLR agonists reveal functional differences between human TLR7 and TLR8, *J. Immunol.*, 174:1259-68 (2005).
Green et al., Mitochondria and apoptosis, Science, 281(5381):1309-12 (1998).
Griffiths et al., Studies toward Lipid A: Synthesis of differentially protected disaccharide fragments, J. Org. Chem., 62(11):3654-8 (1997).
Gutsmann et al., Lipopolysaccharide-binding protein-mediated interaction of lipid A from different origin with phospholipid membranes, Phys. Chem., 2:4521-8 (2000).
Hajjar et al., Human Toll-like receptor 4 recognizes host-specific LPS modifications, Nature Immunol., 3(4):354-9 (2002).
Hampton et al. Macrophage catabolism of lipid A is regulated by endotoxin stimulation, J. Biol. Chem., 266(29):19499-509 (1991).
Hasegawa et al., Elevated promotion of prostacyclin production by synthetic lipid A analogs in aged human endothelial cells in culture, Mechanisms of Ageing and Development, 78:155-62 (1995).
Hawkins et al., A novel class of endotoxin receptor agonists with simplified structure, Toll-like receptor 4-dependent immunostimulatory action, and Adjuvant Activity, J. Pharmacology Experimental Therapeutics, 300(2):655-61 (2002).
Helander et al., Chemical structure of the lipopolysaccharide of Haemophilus influenzae strain I-69 Rd-/b+, Eur. J. Biochem., 177:483-92 (1988).
Hemmi et al., Small anti-viral compounds activate immune cells via the TLR7 MyD88-dependent signaling pathway, Nat. Immunol., 3(2):196-200 (2002).
Hilgers et al., Synergistic effects of synthetic adjuvants on the humoral immune response, Mt. Archs. Allergy Appl. Immunol., 79(4):392-6 (1986).
Hilgers et al., Synthetic sulpholipopolysaccharides: novel adjuvants for humoral immune responses, Immunology, 60(1):141-6 (1987).
Homma et al., Structural Requirements of Lipid A Responsible for the Functions: A study with chemically synthesized lipid A and its analogues, J. Biochem., 98(2):395-406 (1985).
Horsmans et al., Isatoribine, an agonist of TLR7, reduces plasma virus concentration in chronic Hepatitis C infection, Hepatol., 42(3):724-31 (2005).
Hubert et al., Steap: A prostate-specific cell-surface antigen highly expressed in human prostate tumors, Prot. Natl. Acad. Sci. USA, 96(25):14523-8 (1999).
Immune Design Announces Start of Randomized Phase 2 Cancer Immunotherapy Combination Trial in Patients with Soft Tissue Sarcoma, Immune Design (2015), cited as documents D70 in Opposition against European Patent No. 2068918, dated Aug. 30, 2016.
Imoto et al., Chemical synthesis of phosphorylated tetraacyl disaccharide corresponding to a biosynthetic precursor of Lipid A, Tetrahedron Letters, 25(25):2667-70 (1984).
Imoto et al., Total synthesis of *Escherichia coli* lipid A, *Tetrahedron Lett.*, 26(12):1545-8 (1985).
Imoto et al., Total synthesis of *Escherichia coli* lipid A, the endotoxically active principle of the cell-surface lipopolysaccharide, *Bull. Chem. Soc. JP*, 60:2205-14 (1987).
Imoto et al., Total Synthesis of Lipid A, Active Principle of Bacterial Endotoxin, Proc. Japan Acad., 60(B):285-8 (1984).
Invoices for the sale of PHADTM from Avanti Polar Lipids, Inc. to AC Immune SA.
Jacobson et al, Epidemiology and estimated population burden of selected autoimmune diseases in the United States, Clin. Immunol. Immunopathol., 84(3):223-43 (1997).
Jiang et al., Lipid A structures containing novel lipid moieties: Synthesis and adjuvant properties, Bioorg. Med. Chem. Lett., 12:2193-96 (2002).
Jiang et al., Monophosphoryl lipid A analogues with varying 3-0-substitution: synthesis and potent adjuvant activity, Carbohydrate Research, 342(6):784-96 (2007).
Jiang et al., Novel lipid A mimetics derived from pentaerythritol: synthesis and their potent agonistic activity, Tetrahedron, 58:8833-42 (2002).
Johansen et al., Toll-like receptor ligands as adjuvants in allergen-specific immunotherapy, Clin. Exp. Allerg., 35(12):1591-8 (2005).
Johnson et al., 3-0-Desacyl monophosphoryl Lipid A derivatives: Synthesis and immunostimulant activities, *J. Med. Chem.*, 42(22):4640-9 (1999).
Johnson et al., A comparison of the immunomodulating properties of two forms of monophosphoryl lipid A Analogues, J. Immunother., 10:398-404 (1991).
Johnson et al., An Inactivate Rabies Virus-Based Ebola Vaccine, FILORAB1, Adjuvinated with Glycopyranosyl Lipid A in Stable Emulsion Confers Complete Protection in Nonhuman Primate Challenge Methods, *J. Infect Dis.*, S1 (2016).
Johnson et al., Chemical synthesis of the major constituents of Salmonella Minnesota moniphosphoryl lipid A, J. Carb. Chem., 7(9):1421-6 (1998).
Johnson et al., TLR4 agonists as vaccine adjuvants, *Vacc. Adjuv. Deliv. Syst.*, 131-56 (2007).
Johnson, Molecular adjuvants and immunomodulators: New approaches to immunization, Clin. Microbiol. Rev., 7(3):277-89 (1994).
Jurgens et al., Interaction of hemoglobin with enterobacterial lipopolysaccharide and lipid A, *Eur. J. Biochem.*, 268:4233-42 (2001).
Kaisho et al., Pleiotropic function of toll-like receptors, Microbes Infect., 6(15):1388-94 (2004).
Kanegasaki et al., Biological activities of analogues of lipid A based chemically on the revised structural model, Eur. J. Biochem., 143(2):237-42 (1984).
Kanegasaki et al., Structure-activity relationship of lipid A: comparison of biological activities of natural and synthetic lipid A's with different fatty acid compositions, J. Biochem., 99(4):1203-10 (1986).
Kanzler et al., Therapeutic targeting of innate immunity with Toll-like receptor agonists and antagonists, Nature Medicine, 13(5):552-9 (2007).
Kasai et al., Immunochemistry of lipid A, Adv. Exp. Med. Biol., 256:71-9 (1990).
Kasai et al., In Vitro antigenic reactivity of synthetic lipid A analogues as determined by monoclonal and conventional antibodies, Biochem. Biophys. Res. Commun., 128(2):607-12 (1985).
Kasai et al., Structure-activity relationships of endotoxic lipid A containing 2,3-diamino-2,3-dideoxy-D-glucose, in Cellular and Molecular Aspects of Endotoxin Reactions: Proceeding of the 1st congress of the international endotoxin society, Elsevier Science Publishers B.V. (Biomedical Division), San Diego, May 9-12, 121-8 (1990).
Kawahara et al., Modification of the structure and activity of lipid A in Yersinia pestis lipopolysaccharide by growth temperature, Infect. Immunity, 70(8):4092-8 (2002).
Kensil et al., Separation and characterization of saponins with adjuvant activity from Quillaja Saponaria molina cortex, J. Immunology, 46(2):431-7 (1991).
Kensil, Saponins as vaccine adjuvants, Crit. Rev. Ther. Drug Carrier Syst., 13(1-2):1-55 (1996).
Kersten et al., Liposomes and ISCOMs, Vaccine, 21:915-20 (2003).
Kim et al., Crystal Structure of the TLR4-MD-2 complex with bound endotoxin antagonist eritoran, Cell, 130:906-17 (2007).
Kim et al., Immunodominant epitopes in herpes simplex virus type 2 glycoprotein D are not recognized by CD4 lymphocytes from both HSV-1 and HSV-2 seropositive subjects, *J Immunol.* 181:6604-15 (2008).

(56) References Cited

OTHER PUBLICATIONS

Kiso et al., Synthesis of the Optically Active 4-0-phosphono-d-glucosamine derivatives related to the nonreducing-sugar subunit of bacterial lipid A, Carbohyd. Res., 162:127-40 (1987).
Knirel et al., Conserved and variable structural features in the lipopolysaccharide of Pseudomonas aeruginosa, J. Endotox. Res., 12(6):324-36 (2006).
Kolls et al., Prolonged and effective blockade of tumor necrosis factor activity through adenovirus-mediated gene transfer, Proc. Natl. Acad. Sci. USA, 91:215-9 (1994).
Kotani et al., Immunobiological activities of synthetic lipid A analogs with low endotoxicity, Infect. Immunity, 54(3): 673-8 (1986).
Kotani et al., Low endotoxic activities of synthetic salmonella-type lipid A with an additional acyloxyacyl Group on the 2-Amino group of beta(1-6)glucosamine disaccharide 1,4'-bisphosphate, Infect. Immunity, 52(3):872-84 (1986).
Kotani et al., Structural requirements of Lipid A. Endotoxicity and other biological activities—An Overview, Adv. Exp. Med. Biol., 256:13-43 (1990).
Kotani et al., Synthetic lipid A with endotoxic and related biological activities comparable to those of a natural lipid a from an Escherichia coli re-mutant, Infect. Immunity, 49(1):225-37 (1985).
Kriegler et al., A novel form of TNF/Cachectin is a cell surface cytotoxic transmembrane protein: Ramifications for the complex physiology of TNF, Cell, 53(1):45-53 (1988).
Kumazawa et al., Importance of Fatty Acid Substituents of Chemically Synthesized Lipid A-Subunit analogs in the expression of immunopharmacological activity, Infect. Immunity, 56(1):149-55 (1988).
Kusumoto et al., Structural basis for endotoxic and antagonistic activities: investigation with novel synthetic lipid A analogs, J. Endotox. Res., 9(6):361-6 (2003).
Kusumoto et al., Synthesis of endotoxic principle of bacterial lipopolysaccharide and its recognition by the innate immune systems of hosts, Chem. Record, 6:333-43 (2006).
Lacaille-Dubois et al., A review of the biological and pharmacological activities of saponins, Phytomedicine, 2(4):363-86 (1996).
Lee et al., Activation of anti-Hepatitis C virus responses via toll-like receptor 7, Proc. Nat. Acad. Sci. USA, 103(6):1828-33 (2006).
Letter from the Opponent, Opposition against EP 2068918, Opposition by Avanti Polar Lipids, Inc. dated Mar. 4, 2014.
Letter from Thomas G. Peterson to Steven G. Reed, Ph.D. dated Mar. 4, 2011.
Li et al., Assessment of recombinant adenoviral vectors for hepatic gene therapy, Hum. Gene Ther., 4(4):403-9 (1993).
Lien et al., A novel synthetic acyclic lipid A-like agonist activates cells via the lipopolysaccharide/Toll-like Receptor 4 signaling pathway, J. Biol. Chem., 276(3):1873-80 (2001).
Lien et al., Adjuvants and their signaling pathways: Beyond TLRs, Nat. Immunol., 4(12):1162-4 (2003).
Lin et al., Implication of toll-like receptor and tumor necrosis factor alpha signaling in septic shock, Shock, 24(3):206-9 (2005).
Liu et al., A divergent synthesis of lipid A and its chemically stable unnatural analogues, Bull. Chem. Soc. Jpn., 72:1377-85 (1999).
Liu et al., Enzymatic preparation of (S)-3-Hydroxytetradecanoic acid and synthesis of unnatural analogues of lipid A containing the (S)-Acid, Bull. Chem. Soc. Jpn., 70:1441-50 (1997).
Liu, Vaccine developments, Nature Med., 4(5):515-9 (1998).
Loppnow et al., Lipid A, The immunostimulatory principle of lipopolysaccharides?, Adv. Exp. Med. Biol., 256:561-6 (1990).
Lu et al., A Novel Gene (PLU-1) containing highly conserved putative dna/chromatin binding motifs is specifically up-regulated in breast cancer, J. Biol. Chem., 274(22):15633-45 (1999).
Luster, The role of chemokines in linking innate and adaptive immunity, Curr. Opin. Immunol., 14(1):129-35 (2002).
Maeda et al., Adjuvant activities of synthetic lipid A subunit analogues and its conjugates with muramyl dipeptide derivatives, Vaccine, 7(3):275-81 (1989).

Malakoff, Aluminum is put on trial as a vaccine booster, Science, 288(5470):1323-4 (2000).
Mallios, Predicting class II MHC/peptide multi-level binding with an iterative stepwise discriminant analysis meta-algorithm, Bioinformatics, 17:942-8 (2001).
Masoud et al., Investigation of the structure of lipid A from Actinobacillus actinomycetemcomitans strain Y4 and human clinical isolate PO 1021-7, Eur. J. Biochem., 200:775-9 (1991).
Mata-Haro et al., The vaccine adjuvant monophosphoryl lipid A as a TRIF-biased agonist of TLR4, Science, 316:1628-2 (2007).
McCluskie et al., CpG DNA is a potent enhancer of systemic and mucosal immune responses against hepatitis B surface antigen with intranasal administration to Mice, J. Immunol., 161(9):4463-6 (1998).
MEDI7510 for Respiratory Syncytial Virus Advances to Phase 2 Leverages Immune Design's GLAAS™ Discovery Platform, Immune Design (2015).
Medzhitov et al., Innate immunity: Impact on the adaptive immune response, Curr. Opin. Immunol., 9(1):4-9 (1997).
Medzhitov, Toll-like receptors and innate immunity, Nat. Rev. Immunol., 1(2):135-45 (2001).
Melaugh et al., Partial characterization of the major lipooligosaccharide from a strain of Haemophilus ducreyi, the causative agent of chancroid, a genital ulcer disease, J. Biol. Chem., 267:13434-9 (1992).
Merck Index Online (SM), CAS Registry No. 11024-24-1, Digitonin, 2005.
Merck Index Online (SM), CAS Registry No. 111-02-4, Squalene, 2005.
Merck Index Online (SM), CAS Registry No. 6805-41-0, Escin, 2005.
Mikhail et al., Structural characterization of lipid A from nontypeable and type f Haemophilus influenzae: Variability of fatty acid substitution, Analytical Biochem., 340:303-16 (2005).
Minutes of the MDR1 Teleconference, Jul. 26, 2005, cited as document D46 in Opposition against European Patent No. 2068918, dated Aug. 30, 2016.
Minutes of the MDR1 Teleconference, Aug. 23, 2005, cited as document D47 in Opposition against European Patent No. 2068918, dated Aug. 30, 2016.
Minutes of the MDR1 Teleconference, Aug. 30, 2005, cited as document D48 in Opposition against European Patent No. 2068918, dated Aug. 30, 2016.
Mitchell et al., Active Specific Immunotherapy for Melanoma: Phase I Trial of Allogeneic Lysates and a Novel Adjuvant, Cancer Res., 48:5883-93 (1988).
Mitchell et al., Expression of the pneumolysin gene in Escherichia Coli: Rapid purification and biological properties, Biochem. Biophys. Acta, 1007:67-72 (1989).
Moran, Biological and serological characterization of Campylobacter jejuni lipopolysaccharides with deviating core and lipid A structures, FEMS Immunol. and Med. Microbiol., 11:121-30 (1995).
Mueller et al., Aggregates are the biologically active units of endotoxin, J. Biol. Chem., 279(25):26307-313 (2004).
Muotiala, et al., Low biological activity of helicobacter pylori lipopolysaccharide, Infect. Immunity, 60(4):1714-16 (1992).
Myers et al., A critical determinant of lipid A endotoxic activity. Cellular and molecular aspects of endoxoix reactions, 145-56 (1990).
Myers et al., Monophosphoryl lipid A behaves as a T-cell-independent type 1 carrier for hapten-specific antibody response in mice, Infection and Immunity, 63(1):168 (1995).
Nakao et al., Surface-expressed TLR6 participates in the recognition of diacylated lipopeptide and peptidoglycan in human cells, J. Immunol., 174:1566-73 (2005).
Nelson et al., Molecular cloning and characterization of prostase, an androgen-regulated serine protease with prostate-restricted expression, Proc. Natl. Acad. Sci. USA, 96(6):3114-9 (1999).
Notice of Opposition Against European Patent No. 2 068 912-B1 (European Application No. 07 87 5082.5), Vaccine Composition Containing Synthetic Adjuvant, 36 pages, dated Feb. 1, 2013.

(56) References Cited

OTHER PUBLICATIONS

Persing et al., Taking Toll: Lipid A Mimetics as Adjuvants and Immunomodulators, *Trends in Microbiology*, 10(10):S32-7 (2002).
PHADTM advertisement, *J. Biol. Chem.*, 282 (2007).
Press Release—Immune Design Partners with Leading Cancer Organizations to Advance Novel Immunotherapy Research—Cancer Research Institute, Jul. 12, 2013.
Qureshi et al., Complete structural determination of lipopolysaccharide obtained from deep rough mutant of *Escherichia coli, J. Biol. Chem.*, 263:11971-6 (1988).
Qureshi et al., Monophosphoryl lipid A obtained from lipopolysaccharides of *Salmonella minnesota* R595, J. Biol. Chem., 260(9):5271-8 (1985).
Qureshi et al., Position of ester groups in the lipid A backbone of lipopolysaccharides obtained from Salmonella typhimurium, J. Biol. Chem., 258(21):12947-51 (1983).
Qureshi et al., Purification and structural determination of nontoxic lipid A obtained from the lipopolysaccharide of Salmonella Typhimurium, J. Biol. Chem., 257(19):11808-15 (1982).
Raetz et al., Kdo2-lipid A of *Escherichia coli*, a defined endotoxin that activates macrophages via TLR-4, J. Lipid Res., 47:1097-111 (2006).
Reed et al., An improved serodiagnostic procedure for visceral leishmaniasis, Am. J. Trop. Med. Hyg., 43(6):632-9 (1990).
Reed et al., New adjuvants for prophylactic and therapeutic vaccines, pp. 1-58, Oct. 13, 2009.
Reed et al., New horizons in adjuvants for vaccine development, Trends Immunol., 30(1):23-32 (2009).
Reiter et al., Prostate stem cell antigen: A cell surface marker overexpressed in prostate cancer, Proc. Nat. Acad. Sci. USA, 95(4):1735-40 (1998).
Ribi et al., Beneficial modification of the endotoxin molecule, *J. Biol. Resp. Modifiers*, 3:1-9 (1984).
Richards et al., Immunogenicity of liposomal malaria sporozoite antigen in monkeys: Adjuvant effects of aluminum hydroxide and non-pyrogenic liposomal lipid A, *Vaccine*, 7:506-12 (1989).
Rietschel et al., Bacterial endotoxin: molecular relationships of structure to activity and function, FASEB J., 8:217-25 (1994).
Rietschel et al., Endotoxic properties of synthetic pentaacyl lipid A precursor Ib and a structural isomer, Eur. J. Biochem., 169:27-31 (1987).
Rietschel et al., Lipid A, the endotoxic center of bacterial lipopolysaccharides: Relation of chemical structure to biological activity, Progr. Clin. Biol. Res., 231: 25-53 (1987).
Rietschel et al., The chemical structure of bacterial endotoxin in relation to bioactivity, Immunobiology, 187:169-90 (1993).
Robbins et al., Human tumor antigens recognized by T-Cells, Curr. Opin. Immunol., 8(5):628-36 (1996).
Rothenberg et al., Stimulation of rabbit synoviocyte prostaglandin E2 synthesis by lipopolysaccharides and their subunit structures, Arthritis and Rheumatism, 31(2) (1988).
Rubins et al., Pneumolysin in pneumococcal adherence and colonization, Microb. Pathog., 25(6):337-42 (1998).
Rudbach et al., Ribi Adjuvants: Chemistry, biology and utility in vaccines for human and veterinary medicine, theory and practical application of adjuvants, 13:287-313 (1995).
Salem et al., The adjuvant effects of the toll-like receptor 3 ligand polyinosinic-cytidylic acid poly (I:C) on antigen-specific CD8+ T cell responses are partially dependent on NK cells with the induction of a beneficial cytokine milieu, Vaccine, 24(24):5119-32 (2006).
Salkowski et al., Lipopolysaccharide and monophosphoryl lipid A differentially regulate interleukin-12, Gamma interferon, and interleukin-10 mRNA production in murine macrophages, *Infect. Immunity*, 65(8):3239-47 (1997).
Salomon et al., Cripto: A novel epidermal growth factor (EGF)-related peptide in mammary gland development and Neoplasia, BioEssays, 21(1):61-70 (1999).
Schirmbeck et al., Antigenic epitopes fused to cationic peptide bound to oligonucleotides facilitate toll-like receptor 9-Dependent, but CD4+ T cell help-independent priming of CD8+ T cells, J. Immunol., 171(10):5198-207 (2003).
Schmidt et al., Cytokine and Ig-production by CG-containing sequences with phosphorodiester backbone and dumbbell shape, Allergy, 61(1):56-63 (2006).
Schnur et al., Leishmanial serotypes as distinguished by the gel diffusion of factors excreted in vitro and in vivo, Isrl. J. Med. Sci., 8(7):932-42 (1972).
Schromm et al., Biological activities of lipopolysaccharides are determined by the shape of their lipid A portion, Eur. J. Biochem., 267:2008-13 (2000).
Second Declaration of Steven Reed, Ph.D. with Appendices A and B, executed on Apr. 30, 2012, filed in U.S. Appl. No. 11/862,122.
Senaldi et al., Serological diagnosis of visceral leishmaniasis by a dot-enzyme immunoassay for the detection of a leishmania donovani-related circulating antigen, J. Immunol. Methods, 193(1):9-15 (1996).
Seong et al., Hydrophobicity: an ancient damage-associated molecular pattern that initiates innate immune responses, *Nature Reviews Immunol.*, 4:469-78 (2004).
Sethi et al., Bacterial infection in Chronic Obstructive Pulmonary Disease in 2000: A State-of-the-Art Review, Clin. Microbiol. Rev., 14(2):336-63 (2001).
Seydel et al., Intrinsic conformation of lipid A is responsible for agonistic and antagonistic activity, Eur. J. Biochem., 267:3032-9 (2000).
Seydel et al. Physicochemical characterization of carboxymethyl lipid A derivatives in relation to biological activity, FEBS J., 272:327-40 (2005).
Seydel et al., Supramolecular structure of lipopolysaccharide and free lipid A under physiological conditions as determined by synchrotron small-angel X-ray diffraction, Eur. J. Biochem., 186:325-32 (1989).
Simon, CRC Desk Reference for Allergy and Asthma, CRC Press LLC, 20-3 (2000).
Smith et al, The active form of tumor necrosis factor is a trimer, *J. Biol. Chem.*, 262(15):6951-54 (1987).
Soboll et al., Expression of Toll-Like Receptors (TLR) and responsiveness to TLR agonists by polarized mouse uterine epithelial cells in culture, Biol. Reprod., 75(1):131-9 (2006).
Steers et al., Modulation of immunoproteasome subunits by liposomal lipid A, Vaccine, 26:2849-59 (2008).
Stover et al., Structure activity relationship of synthetic Toll-Like Receptor 4 agonists, J. Biol. Chem., 279(6):4440-9 (2004).
Takada et al., Immunopharmacological Activities of a Synthetic Counterpart of a Biosynthetic Lipid A precursor molecule and of its analogs, Infection Immunity, 48(1):219-27 (1985).
Takada et al., Structural requirements of lipid A for endotoxicity and other biological activities, *CRC Critical Reviews Microbiology*, 16(6):477-523 (1989).
Takada et al., Structural requirements of lipid A species in activation of clotting enzymes from the horseshoe crab, and the human complement cascade, Eur. J. Biochem., 175:573-80 (1988).
Takayama et al., Adjuvant Activity of non-ionic block copolymers V. Modulation of antibody isotype by lipopolysaccharides, lipid A and precursors, Vaccine, 9:257-65 (1991).
Takayama et al., Complete structure of lipid a obtained from the lipopolysaccharides of the heptoseless mutant of salmonella typhimurium, J. Biol. Chem., 258(21):12801-3 (1983).
Takayama et al., Influence of fine structure of lipid A in *Limulus* amebocyte lysate clotting and toxic activities, *Infect. Immun.*, 45(2):350-55 (1984).
Takeda et al., Toll-Like Receptors in Innate Immunity, Int. Immunol. 17(1):1-14 (2005).
Takeda et al., Toll-like receptors, *Ann. Rev. Immunol.*, 21:335-76 (2003).
Tamai et al., Cell activation by monosaccharide lipid A analogues utilizing Toll-like receptor 4, *Immunology*, 110:66-72 (2003).
Tanamoto, Dissociation of endotoxic activities in a chemically synthesized lipid a precursor after acetylation, Infection Immunity, 63(2):690-2 (1995).

(56) References Cited

OTHER PUBLICATIONS

Tanamoto, Salmonella-type heptaacylated Lipid A is inactive and acts as an antagonist of lipopolysaccharide action on human line cells, J. Immunol., 164:3149-56 (2000).
Teghanemt et al., Molecular basis of reduced potency of underacylated endotoxins, J. Immun., 175:4669-76 (2005).
Therisod et al., *Helicobacter mustelae* lipid A structure differs from that of *Helicobacter pylori*, FEBS Lett,. 499:1-5 (2001).
Thompson et al., The low-toxicity versions of LPS, MPL® adjuvant and RC529, are efficient djuvants for CD4 T cells, *J. Leukoc. Biol.*, 78:1273-80 (2005).
Trent et al., Diversity of endotoxin and its impact on pathogenesis, J. Endotox. Res., 12(4):205-23 (2006).
Triantafilou et al., Combinational clustering of receptors following stimulation by bacterial products determines lipopolysaccharide responses, Biochem. J., 381:527-36 (2004).
Triozzi et al., Effects of a beta-human chorionic gonadotropin subunit immunogen administered in aqueous solution with a novel nonionic block copolymer adjuvant in patients with advanced cancer, Clin. Cancer Res., 3(12 Pt 1):2355-62 (1997).
Tsan et al., Cytokine function of heat shock proteins, Am. J. Physiol. Cell Phsiol., 286(4):C739-44 (2004).
Tsan et al., Endogenous ligands of Toll-Like Receptors, J. Leukoc. Biol., 76(3):514-9 (2004).
U.S. Appl. No. 11/862,122, filed Sep. 26, 2007, Final Office Action dated Feb. 1, 2010.
U.S. Appl. No. 11/862,122, filed Sep. 26, 2007, Office Action dated Jul. 28, 2009.
U.S. Appl. No. 11/862,122, filed Sep. 26, 2007, Office Action dated May 5, 2011.
U.S. Appl. No. 12/351,710, filed Jan. 9, 2009, Office Action dated Dec. 13, 2010.
Ukei et al., Adjuvant and antitumour activities of synthetic lipid A analogues, Vaccine, 4:21-24 (1986).
Ulrich et al., Topics in vaccine adjuvant research, Chapter 12, The Adjuvant Activity of Monophosphoryl Lipid A, 133-43 (1991).
Ulrich et al., Vaccine design: The subunit and adjuvant approach, Plenum Press, New York, Chapter 21, Monophosphoryl Lipi A as an Adjuvant, 495-524 (1995).
Van Amersfoort et al., Receptors, mediators, and mechanisms involved in bacterial sepsis and septic shock, Clinical Microbiology Reviews, 16(3):379-414 (2003).
Van den Eynde et al., Tumor antigens recognized by t-lymphocytes, Mt. J. Clin. Lab. Res., 27:81-6 (1997).
Velasco et al., Toll-Like Receptor 4 or 2 agonists decrease allergic inflammation, Amer. J. Resp. Cell Mole. Biol., 32:218-24 (2005).
Vincent et al., Long-term correction of mouse dystrophic degeneration by adenovirus-mediated transfer of a minidystrophin gene, Nat. Genet., 5(2):130-4 (1993).
Vollmer et al., Immunopharmacology of CpG oligodeoxynucleotides and ribavirin, Antimicrob. Agents Chemother., 48(6):2314-7 (2004).
Vollmer, Progress in drug development of immunostimulatory CpG oligodeoxynucleotide ligands for TLR9, Exp. Opin. Biolog. Ther., 5(5):673-82 (2005).
Wang et al., Inhibition of endotoxin-induced interleukin-6 production by synthetic lipid A partial structure in human peripheral blood mononuclear cells, *Infect. Immun.*, 59(12):4655-64 (1991).
Wang et al., pH-sensitive Immunoliposomes Mediate Target-Cell-Specific Delivery and Controlled Expression of a Foreign Gene in Mouse, Proc. Natl. Acad. Sci. USA, 84:7851-5 (1987).
Wasylyk et al., The Ets Family of Transcription Factors, *Eur. J. Biochem.*, 211(1-2):7-18 (1993).

Webpage from List Biological Laboratories, Inc. showing the 'order products online' page for lipopolysaccharides.
Weeratna et al., TLR Agonists as Vaccine Adjuvants: Comparison of CpG ODN and Resiquimod (R-848), *Vaccine*, 23(45):5263-70 (2005).
Weihrauch et al., Phase I/II Combined chemoimmunotherapy with carcinoembryonic antigen-derived HLA-A2-restricted CAP-1 peptide and irinotecan, 5-Fluorouracil, and leucovorin in patients with primary metastatic colorectal cancer, *Clin. Cancer Res.*, 11(16):5993-6001 (2005).
Wheeler et al., Allergy vaccines—new approaches to an old concept, Expert Opinion on Biol. Ther., 4(9):1473-81 (2004).
Wu et al., Targeting genes: Delivery and persistent expression of a foreign gene driven by mammalian regulatory elements in vivo, J. Biol. Chem., 264(29):16985-87 (1989).
Xiong et al., Inhibition of interleukin-12 p40 Transcription and NF-kB activation by nitric oxide in murine macrophages and dendritic cells, J. Biol. Chem., 279(11):10776-83 (2004).
Yang et al., The immunogenicity-enhancing effect of emulsion vaccine adjuvants is independent of the dispersion type and antigen release rate-a revisit of the role of the hydrophile-lipophile balance (HLB) value, Vaccine, 23:2665-75 (2005).
Yasuda et al., Biological activity of chemically synthesized analogues of lipid A, Euro. J. Biochem., 124(2):405-7 (1982).
Yasuda et al., Further study of biological activities of chemically synthesized analogues of lipid A in artificial membrane vesicles, Eur. J. Biochem., 140(2):245-8 (1984).
Yeh et al., Improving protein delivery from microparticles using blends of Poly(DL Lactide Co-Glycolide) and Poly(Ethylene Oxide)-Poly(Propylene Oxide) Copolymers, Pharm. Res., 13(11):1693-8 (1996).
Yoshida et al., Endotoxic properties of chemically synthesized lipid A analogs, Microbiol. Immunol., 33(10):797-810 (1989).
Yoshida et al., Monophosphoryl Lipid A induces pharmacologic 'preconditioning' in rabbit hearts without concomitant expression of 70-kDa heat shock protein, *Molec. Cell. Biochem.*, 156:1-8 (1996).
Yoshikawa et al., Bioactive saponins and glycosides. III. Horse Chestnut. (1): The structures, inhibitory effects on ethanol absorbtion, and hypoglycemic activity of escins Ia, Ib, IIa, IIb, and IIIa from the seeds of aesculus Hippocastanum L., Chem. Pharm. Bull., 4(8):1454-64 (1996).
Zahringer et al., Molecular structure of lipid A, the endotoxic center of bacterial lipopolysaccharides, *Adv. Carbohydrate Chem. Biochem.*, 50:211-76 (1994).
Zijlstra et al., The direct agglutination test for diagnosis of visceral leishmaniasis under field conditions in sudan: comparison of aqueous and freeze-dried antigens, Trans. R. Soc. Trop. Med. Hyg., 91(6):671-3 (1997).
Boukhvalova et al., Efficacy of the Herpes Simplex Virus 2 (HSV-2) Glycoprotein D/AS04 Vaccine against Genital HSV-2 and HSV-1 Infection and Disease in the Cotton Rat Sigmodon hispidus Model, *J. Virol.*, 89(19):9825-40 (2015).
Cohen, Laboratory of Infectious Diseases, NIH, Slide Presentation, 16 Slides, Plus an additional page showing evidence of date; Slides available from <http://www/:globe-network.org/sites/default/files/documents/public/en/resources/conferences/2012/herpes-virus-infection-and-immunity/animal-models-for-hsv.pdf> (2012).
NCBI GenGank Reference Sequence: NP_044494.1; DNA packaging tegument protein UL25 (Human Herpesvirus 2). Sub. Aug. 1, 2000; last revision Apr. 23, 2010.
NCBI GenBank Reference Sequence: NP_044536.1; envelope glycoprotein D [Human Herpesvirus 2]. Sub. Aug. 1, 2000; last revision.
NCBI GenBank Accession No. ADG018878 DNA packaging tegument protein [Human Herpesvirus 2]. 1 Updated May 3, 2010.

* cited by examiner

SEQUENCE LISTING

```
<160> NUMBER OF SEQ ID NOS: 17

<210> SEQ ID NO 1
<211> LENGTH: 904
<212> TYPE: PRT
<213> ORGANISM: Herpes Simplex Virus 2

<400> SEQUENCE: 1

Met Arg Gly Gly Gly Leu Ile Cys Ala Leu Val Val Gly Ala Leu Val
```

-continued

```
  1               5                   10                  15
Ala Ala Val Ala Ser Ala Ala Pro Ala Ala Pro Ala Ala Pro Arg Ala
                 20                  25                  30
Ser Gly Gly Val Ala Ala Thr Val Ala Ala Asn Gly Gly Pro Ala Ser
                 35                  40                  45
Arg Pro Pro Val Pro Ser Pro Ala Thr Thr Lys Ala Arg Lys Arg
     50                  55                  60
Lys Thr Lys Lys Pro Pro Lys Arg Pro Glu Ala Thr Pro Pro Asp
 65                  70                  75                  80
Ala Asn Ala Thr Val Ala Ala Gly His Ala Thr Leu Arg Ala His Leu
                 85                  90                  95
Arg Glu Ile Lys Val Glu Asn Ala Asp Ala Gln Phe Tyr Val Cys Pro
                 100                 105                 110
Pro Pro Thr Gly Ala Thr Val Val Gln Phe Glu Gln Pro Arg Arg Cys
             115                 120                 125
Pro Thr Arg Pro Glu Gly Gln Asn Tyr Thr Glu Gly Ile Ala Val Val
             130                 135                 140
Phe Lys Glu Asn Ile Ala Pro Tyr Lys Phe Lys Ala Thr Met Tyr Tyr
145                 150                 155                 160
Lys Asp Val Thr Val Ser Gln Val Trp Phe Gly His Arg Tyr Ser Gln
                 165                 170                 175
Phe Met Gly Ile Phe Glu Asp Arg Ala Pro Val Pro Phe Glu Glu Val
             180                 185                 190
Ile Asp Lys Ile Asn Thr Lys Gly Val Cys Arg Ser Thr Ala Lys Tyr
             195                 200                 205
Val Arg Asn Asn Met Glu Thr Thr Ala Phe His Arg Asp Asp His Glu
             210                 215                 220
Thr Asp Met Glu Leu Lys Pro Ala Lys Val Ala Thr Arg Thr Ser Arg
225                 230                 235                 240
Gly Trp His Thr Thr Asp Leu Lys Tyr Asn Pro Ser Arg Val Glu Ala
                 245                 250                 255
Phe His Arg Tyr Gly Thr Thr Val Asn Cys Ile Val Glu Glu Val Asp
             260                 265                 270
Ala Arg Ser Val Tyr Pro Tyr Asp Glu Phe Val Leu Ala Thr Gly Asp
             275                 280                 285
Phe Val Tyr Met Ser Pro Phe Tyr Gly Tyr Arg Glu Gly Ser His Thr
             290                 295                 300
Glu His Thr Ser Tyr Ala Ala Asp Arg Phe Lys Gln Val Asp Gly Phe
305                 310                 315                 320
Tyr Ala Arg Asp Leu Thr Thr Lys Ala Arg Ala Thr Ser Pro Thr Thr
                 325                 330                 335
Arg Asn Leu Leu Thr Thr Pro Lys Phe Thr Val Ala Trp Asp Trp Val
             340                 345                 350
Pro Lys Arg Pro Ala Val Cys Thr Met Thr Lys Trp Gln Glu Val Asp
             355                 360                 365
Glu Met Leu Arg Ala Glu Tyr Gly Gly Ser Phe Arg Phe Ser Ser Asp
             370                 375                 380
Ala Ile Ser Thr Thr Phe Thr Asn Leu Thr Glu Tyr Ser Leu Ser
385                 390                 395                 400
Arg Val Asp Leu Gly Asp Cys Ile Gly Arg Asp Ala Arg Glu Ala Ile
                 405                 410                 415
Asp Arg Met Phe Ala Arg Lys Tyr Asn Ala Thr His Ile Lys Val Gly
             420                 425                 430
```

```
Gln Pro Gln Tyr Tyr Leu Ala Thr Gly Gly Phe Leu Ile Ala Tyr Gln
        435                 440                 445

Pro Leu Leu Ser Asn Thr Leu Ala Glu Leu Tyr Val Arg Glu Tyr Met
450                 455                 460

Arg Glu Gln Asp Arg Lys Pro Arg Asn Ala Thr Pro Ala Pro Leu Arg
465                 470                 475                 480

Glu Ala Pro Ser Ala Asn Ala Ser Val Glu Arg Ile Lys Thr Thr Ser
                485                 490                 495

Ser Ile Glu Phe Ala Arg Leu Gln Phe Thr Tyr Asn His Ile Gln Arg
            500                 505                 510

His Val Asn Asp Met Leu Gly Arg Ile Ala Val Ala Trp Cys Glu Leu
        515                 520                 525

Gln Asn His Glu Leu Thr Leu Trp Asn Glu Ala Arg Lys Leu Asn Pro
    530                 535                 540

Asn Ala Ile Ala Ser Ala Thr Val Gly Arg Arg Val Ser Ala Arg Met
545                 550                 555                 560

Leu Gly Asp Val Met Ala Val Ser Thr Cys Val Pro Val Ala Pro Asp
                565                 570                 575

Asn Val Ile Val Gln Asn Ser Met Arg Val Ser Ser Arg Pro Gly Thr
            580                 585                 590

Cys Tyr Ser Arg Pro Leu Val Ser Phe Arg Tyr Glu Asp Gln Gly Pro
        595                 600                 605

Leu Ile Glu Gly Gln Leu Gly Glu Asn Asn Glu Leu Arg Leu Thr Arg
    610                 615                 620

Asp Ala Leu Glu Pro Cys Thr Val Gly His Arg Arg Tyr Phe Ile Phe
625                 630                 635                 640

Gly Gly Gly Tyr Val Tyr Phe Glu Glu Tyr Ala Tyr Ser His Gln Leu
                645                 650                 655

Ser Arg Ala Asp Val Thr Thr Val Ser Thr Phe Ile Asp Leu Asn Ile
            660                 665                 670

Thr Met Leu Glu Asp His Glu Phe Val Pro Leu Glu Val Tyr Thr Arg
        675                 680                 685

His Glu Ile Lys Asp Ser Gly Leu Leu Asp Tyr Thr Glu Val Gln Arg
    690                 695                 700

Arg Asn Gln Leu His Asp Leu Arg Phe Ala Asp Ile Asp Thr Val Ile
705                 710                 715                 720

Arg Ala Asp Ala Asn Ala Ala Met Phe Ala Gly Leu Cys Ala Phe Phe
                725                 730                 735

Glu Gly Met Gly Asp Leu Gly Arg Ala Val Gly Lys Val Val Met Gly
            740                 745                 750

Val Val Gly Gly Val Val Ser Ala Val Ser Gly Val Ser Ser Phe Met
        755                 760                 765

Ser Asn Pro Phe Gly Ala Leu Ala Val Gly Leu Leu Val Leu Ala Gly
    770                 775                 780

Leu Val Ala Ala Phe Phe Ala Phe Arg Tyr Val Leu Gln Leu Gln Arg
785                 790                 795                 800

Asn Pro Met Lys Ala Leu Tyr Pro Leu Thr Thr Lys Glu Leu Lys Thr
                805                 810                 815

Ser Asp Pro Gly Gly Val Gly Gly Glu Gly Glu Gly Ala Glu Gly
            820                 825                 830

Gly Gly Phe Asp Glu Ala Lys Leu Ala Glu Ala Arg Glu Met Ile Arg
        835                 840                 845
```

```
Tyr Met Ala Leu Val Ser Ala Met Glu Arg Thr Glu His Lys Ala Arg
    850                 855                 860
Lys Lys Gly Thr Ser Ala Leu Leu Ser Ser Lys Val Thr Asn Met Val
865                 870                 875                 880
Leu Arg Lys Arg Asn Lys Ala Arg Tyr Ser Pro Leu His Asn Glu Asp
                885                 890                 895
Glu Ala Gly Asp Glu Asp Glu Leu
                900

<210> SEQ ID NO 2
<211> LENGTH: 393
<212> TYPE: PRT
<213> ORGANISM: Herpes Simplex Virus 2

<400> SEQUENCE: 2

Met Gly Arg Leu Thr Ser Gly Val Gly Thr Ala Ala Leu Leu Val Val
1               5                   10                  15
Ala Val Gly Leu Arg Val Val Cys Ala Lys Tyr Ala Leu Ala Asp Pro
                20                  25                  30
Ser Leu Lys Met Ala Asp Pro Asn Arg Phe Arg Gly Lys Asn Leu Pro
            35                  40                  45
Val Leu Asp Gln Leu Thr Asp Pro Pro Gly Val Lys Arg Val Tyr His
    50                  55                  60
Ile Gln Pro Ser Leu Glu Asp Pro Phe Gln Pro Ser Ile Pro Ile
65                  70                  75                  80
Thr Val Tyr Tyr Ala Val Leu Glu Arg Ala Cys Arg Ser Val Leu Leu
                85                  90                  95
His Ala Pro Ser Glu Ala Pro Gln Ile Val Arg Gly Ala Ser Asp Glu
                100                 105                 110
Ala Arg Lys His Thr Tyr Asn Leu Thr Ile Ala Trp Tyr Arg Met Gly
            115                 120                 125
Asp Asn Cys Ala Ile Pro Ile Thr Val Met Glu Tyr Thr Glu Cys Pro
130                 135                 140
Tyr Asn Lys Ser Leu Gly Val Cys Pro Ile Arg Thr Gln Pro Arg Trp
145                 150                 155                 160
Ser Tyr Tyr Asp Ser Phe Ser Ala Val Ser Glu Asp Asn Leu Gly Phe
                165                 170                 175
Leu Met His Ala Pro Ala Phe Glu Thr Ala Gly Thr Tyr Leu Arg Leu
            180                 185                 190
Val Lys Ile Asn Asp Trp Thr Glu Ile Thr Gln Phe Ile Leu Glu His
        195                 200                 205
Arg Ala Arg Ala Ser Cys Lys Tyr Ala Leu Pro Leu Arg Ile Pro Pro
210                 215                 220
Ala Ala Cys Leu Thr Ser Lys Ala Tyr Gln Gln Gly Val Thr Val Asp
225                 230                 235                 240
Ser Ile Gly Met Leu Pro Arg Phe Ile Pro Glu Asn Gln Arg Thr Val
                245                 250                 255
Ala Leu Tyr Ser Leu Lys Ile Ala Gly Trp His Gly Pro Lys Pro Pro
            260                 265                 270
Tyr Thr Ser Thr Leu Leu Pro Pro Glu Leu Ser Asp Thr Thr Asn Ala
        275                 280                 285
Thr Gln Pro Glu Leu Val Pro Glu Asp Pro Glu Asp Ser Ala Leu Leu
    290                 295                 300
Glu Asp Pro Ala Gly Thr Val Ser Ser Gln Ile Pro Pro Asn Trp His
305                 310                 315                 320
```

```
Ile Pro Ser Ile Gln Asp Val Ala Pro His Ala Pro Ala Ala Pro
            325                 330                 335

Ser Asn Pro Gly Leu Ile Ile Gly Ala Leu Ala Gly Ser Thr Leu Ala
            340                 345                 350

Val Leu Val Ile Gly Gly Ile Ala Phe Trp Val Arg Arg Ala Gln
            355                 360                 365

Met Ala Pro Lys Arg Leu Arg Leu Pro His Ile Arg Asp Asp Asp Ala
    370                 375                 380

Pro Pro Ser His Gln Pro Leu Phe Tyr
385                 390
```

<210> SEQ ID NO 3
<211> LENGTH: 306
<212> TYPE: PRT
<213> ORGANISM: Herpes Simplex Virus 2

<400> SEQUENCE: 3

```
Lys Tyr Ala Leu Ala Asp Pro Ser Leu Lys Met Ala Asp Pro Asn Arg
1               5                   10                  15

Phe Arg Gly Lys Asn Leu Pro Val Leu Asp Gln Leu Thr Asp Pro Pro
            20                  25                  30

Gly Val Lys Arg Val Tyr His Ile Gln Pro Ser Leu Glu Asp Pro Phe
        35                  40                  45

Gln Pro Pro Ser Ile Pro Ile Thr Val Tyr Tyr Ala Val Leu Glu Arg
    50                  55                  60

Ala Cys Arg Ser Val Leu Leu His Ala Pro Ser Glu Ala Pro Gln Ile
65                  70                  75                  80

Val Arg Gly Ala Ser Asp Glu Ala Arg Lys His Thr Tyr Asn Leu Thr
                85                  90                  95

Ile Ala Trp Tyr Arg Met Gly Asp Asn Cys Ala Ile Pro Ile Thr Val
            100                 105                 110

Met Glu Tyr Thr Glu Cys Pro Tyr Asn Lys Ser Leu Gly Val Cys Pro
        115                 120                 125

Ile Arg Thr Gln Pro Arg Trp Ser Tyr Tyr Asp Ser Phe Ser Ala Val
    130                 135                 140

Ser Glu Asp Asn Leu Gly Phe Leu Met His Ala Pro Ala Phe Glu Thr
145                 150                 155                 160

Ala Gly Thr Tyr Leu Arg Leu Val Lys Ile Asn Asp Trp Thr Glu Ile
                165                 170                 175

Thr Gln Phe Ile Leu Glu His Arg Ala Arg Ala Ser Cys Lys Tyr Ala
            180                 185                 190

Leu Pro Leu Arg Ile Pro Pro Ala Ala Cys Leu Thr Ser Lys Ala Tyr
        195                 200                 205

Gln Gln Gly Val Thr Val Asp Ser Ile Gly Met Leu Pro Arg Phe Ile
    210                 215                 220

Pro Glu Asn Gln Arg Thr Val Ala Leu Tyr Ser Leu Lys Ile Ala Gly
225                 230                 235                 240

Trp His Gly Pro Lys Pro Pro Tyr Thr Ser Thr Leu Leu Pro Pro Glu
                245                 250                 255

Leu Ser Asp Thr Thr Asn Ala Thr Gln Pro Glu Leu Val Pro Glu Asp
            260                 265                 270

Pro Glu Asp Ser Ala Leu Leu Glu Asp Pro Ala Gly Thr Val Ser Ser
        275                 280                 285

Gln Ile Pro Pro Asn Trp His Ile Pro Ser Ile Gln Asp Val Ala Pro
```

```
                290                 295                 300

His His
305

<210> SEQ ID NO 4
<211> LENGTH: 1374
<212> TYPE: PRT
<213> ORGANISM: Herpes Simplex Virus 2

<400> SEQUENCE: 4

Met Ala Ala Pro Ala Arg Asp Pro Pro Gly Tyr Arg Tyr Ala Ala
1               5                   10                  15

Met Val Pro Thr Gly Ser Ile Leu Ser Thr Ile Glu Val Ala Ser His
                20                  25                  30

Arg Arg Leu Phe Asp Phe Phe Ala Arg Val Arg Ser Asp Glu Asn Ser
            35                  40                  45

Leu Tyr Asp Val Glu Phe Asp Ala Leu Leu Gly Ser Tyr Cys Asn Thr
        50                  55                  60

Leu Ser Leu Val Arg Phe Leu Glu Leu Gly Leu Ser Val Ala Cys Val
65                  70                  75                  80

Cys Thr Lys Phe Pro Glu Leu Ala Tyr Met Asn Glu Gly Arg Val Gln
                85                  90                  95

Phe Glu Val His Gln Pro Leu Ile Ala Arg Asp Gly Pro His Pro Val
            100                 105                 110

Glu Gln Pro Val His Asn Tyr Met Thr Lys Val Ile Asp Arg Arg Ala
        115                 120                 125

Leu Asn Ala Ala Phe Ser Leu Ala Thr Glu Ala Ile Ala Leu Leu Thr
130                 135                 140

Gly Glu Ala Leu Asp Gly Thr Gly Ile Ser Leu His Arg Gln Leu Arg
145                 150                 155                 160

Ala Ile Gln Gln Leu Ala Arg Asn Val Gln Ala Val Leu Gly Ala Phe
                165                 170                 175

Glu Arg Gly Thr Ala Asp Gln Met Leu His Val Leu Leu Glu Lys Ala
            180                 185                 190

Pro Pro Leu Ala Leu Leu Pro Met Gln Arg Tyr Leu Asp Asn Gly
        195                 200                 205

Arg Leu Ala Thr Arg Val Ala Arg Ala Thr Leu Val Ala Glu Leu Lys
210                 215                 220

Arg Ser Phe Cys Asp Thr Ser Phe Phe Leu Gly Lys Ala Gly His Arg
225                 230                 235                 240

Arg Glu Ala Ile Glu Ala Trp Leu Val Asp Leu Thr Thr Ala Thr Gln
                245                 250                 255

Pro Ser Val Ala Val Pro Arg Leu Thr His Ala Asp Thr Arg Gly Arg
            260                 265                 270

Pro Val Asp Gly Val Leu Val Thr Thr Ala Ala Ile Lys Gln Arg Leu
        275                 280                 285

Leu Gln Ser Phe Leu Lys Val Glu Asp Thr Glu Ala Asp Val Pro Val
    290                 295                 300

Thr Tyr Gly Glu Met Val Leu Asn Gly Ala Asn Leu Val Thr Ala Leu
305                 310                 315                 320

Val Met Gly Lys Ala Val Arg Ser Leu Asp Asp Val Gly Arg His Leu
                325                 330                 335

Leu Glu Met Gln Glu Glu Gln Leu Glu Ala Asn Arg Glu Thr Leu Asp
            340                 345                 350
```

```
Glu Leu Glu Ser Ala Pro Gln Thr Arg Val Arg Ala Asp Leu Val
            355                 360                 365

Ala Ile Gly Asp Arg Leu Val Phe Leu Glu Ala Leu Glu Lys Arg Ile
370                 375                 380

Tyr Ala Ala Thr Asn Val Pro Tyr Pro Leu Val Gly Ala Met Asp Leu
385                 390                 395                 400

Thr Phe Val Leu Pro Leu Gly Leu Phe Asn Pro Ala Met Glu Arg Phe
                405                 410                 415

Ala Ala His Ala Gly Asp Leu Val Pro Ala Pro Gly His Pro Glu Pro
            420                 425                 430

Arg Ala Phe Pro Pro Arg Gln Leu Phe Phe Trp Gly Lys Asp His Gln
        435                 440                 445

Val Leu Arg Leu Ser Met Glu Asn Ala Val Gly Thr Val Cys His Pro
    450                 455                 460

Ser Leu Met Asn Ile Asp Ala Ala Val Gly Gly Val Asn His Asp Pro
465                 470                 475                 480

Val Glu Ala Ala Asn Pro Tyr Gly Ala Tyr Val Ala Ala Pro Ala Gly
                485                 490                 495

Pro Gly Ala Asp Met Gln Gln Arg Phe Leu Asn Ala Trp Arg Gln Arg
            500                 505                 510

Leu Ala His Gly Arg Val Arg Trp Val Ala Glu Cys Gln Met Thr Ala
        515                 520                 525

Glu Gln Phe Met Gln Pro Asp Asn Ala Asn Leu Ala Leu Glu Leu His
    530                 535                 540

Pro Ala Phe Asp Phe Phe Ala Gly Val Ala Asp Val Glu Leu Pro Gly
545                 550                 555                 560

Gly Glu Val Pro Pro Ala Gly Pro Gly Ala Ile Gln Ala Thr Trp Arg
                565                 570                 575

Val Val Asn Gly Asn Leu Pro Leu Ala Leu Cys Pro Val Ala Phe Arg
            580                 585                 590

Asp Ala Arg Gly Leu Glu Leu Gly Val Gly Arg His Ala Met Ala Pro
        595                 600                 605

Ala Thr Ile Ala Ala Val Arg Gly Ala Phe Glu Asp Arg Ser Tyr Pro
    610                 615                 620

Ala Val Phe Tyr Leu Leu Gln Ala Ala Ile His Gly Ser Glu His Val
625                 630                 635                 640

Phe Cys Ala Leu Ala Arg Leu Val Thr Gln Cys Ile Thr Ser Tyr Trp
                645                 650                 655

Asn Asn Thr Arg Cys Ala Ala Phe Val Asn Asp Tyr Ser Leu Val Ser
            660                 665                 670

Tyr Ile Val Thr Tyr Leu Gly Gly Asp Leu Pro Glu Glu Cys Met Ala
        675                 680                 685

Val Tyr Arg Asp Leu Val Ala His Val Glu Ala Leu Ala Gln Leu Val
    690                 695                 700

Asp Asp Phe Thr Leu Pro Gly Pro Glu Leu Gly Gly Gln Ala Gln Ala
705                 710                 715                 720

Glu Leu Asn His Leu Met Arg Asp Pro Ala Leu Leu Pro Pro Leu Val
                725                 730                 735

Trp Asp Cys Asp Gly Leu Met Arg His Ala Ala Leu Asp Arg His Arg
            740                 745                 750

Asp Cys Arg Ile Asp Ala Gly Gly His Glu Pro Val Tyr Ala Ala Ala
        755                 760                 765

Cys Asn Val Ala Thr Ala Asp Phe Asn Arg Asn Asp Gly Arg Leu Leu
```

-continued

```
            770                 775                 780
His Asn Thr Gln Ala Arg Ala Ala Asp Ala Ala Asp Asp Arg Pro His
785                 790                 795                 800

Arg Pro Ala Asp Trp Thr Val His His Lys Ile Tyr Tyr Tyr Val Leu
                805                 810                 815

Val Pro Ala Phe Ser Arg Gly Arg Cys Cys Thr Ala Gly Val Arg Phe
                820                 825                 830

Asp Arg Val Tyr Ala Thr Leu Gln Asn Met Val Val Pro Glu Ile Ala
                835                 840                 845

Pro Gly Glu Glu Cys Pro Ser Asp Pro Val Thr Asp Pro Ala His Pro
            850                 855                 860

Leu His Pro Ala Asn Leu Val Ala Asn Thr Val Asn Ala Met Phe His
865                 870                 875                 880

Asn Gly Arg Val Val Asp Gly Pro Ala Met Leu Thr Leu Gln Val
                885                 890                 895

Leu Ala His Asn Met Ala Glu Arg Thr Thr Ala Leu Leu Cys Ser Ala
                900                 905                 910

Ala Pro Asp Ala Gly Ala Asn Thr Ala Ser Thr Ala Asn Met Arg Ile
                915                 920                 925

Phe Asp Gly Ala Leu His Ala Gly Val Leu Leu Met Ala Pro Gln His
                930                 935                 940

Leu Asp His Thr Ile Gln Asn Gly Glu Tyr Phe Tyr Val Leu Pro Val
945                 950                 955                 960

His Ala Leu Phe Ala Gly Ala Asp His Val Ala Asn Ala Pro Asn Phe
                965                 970                 975

Pro Pro Ala Leu Arg Asp Leu Ala Arg His Val Pro Leu Val Pro Pro
                980                 985                 990

Ala Leu Gly Ala Asn Tyr Phe Ser  Ser Ile Arg Gln Pro  Val Val Gln
            995                 1000                1005

His Ala  Arg Glu Ser Ala Ala  Gly Glu Asn Ala Leu   Thr Tyr Ala
    1010                1015                1020

Leu Met  Ala Gly Tyr Phe Lys  Met Ser Pro Val Ala   Leu Tyr His
    1025                1030                1035

Gln Leu  Lys Thr Gly Leu His  Pro Gly Phe Gly Phe  Thr Val Val
    1040                1045                1050

Arg Gln  Asp Arg Phe Val Thr  Glu Asn Val Leu Phe  Ser Glu Arg
    1055                1060                1065

Ala Ser  Glu Ala Tyr Phe Leu  Gly Gln Leu Gln Val  Ala Arg His
    1070                1075                1080

Glu Thr  Gly Gly Gly Val Ser  Phe Thr Leu Thr Gln  Pro Arg Gly
    1085                1090                1095

Asn Val  Asp Leu Gly Val Gly  Tyr Thr Ala Val Ala  Ala Thr Ala
    1100                1105                1110

Thr Val  Arg Asn Pro Val Thr  Asp Met Gly Asn Leu  Pro Gln Asn
    1115                1120                1125

Phe Tyr  Leu Gly Arg Gly Ala  Pro Pro Leu Leu Asp  Asn Ala Ala
    1130                1135                1140

Ala Val  Tyr Leu Arg Asn Ala  Val Val Ala Gly Asn  Arg Leu Gly
    1145                1150                1155

Pro Ala  Gln Pro Leu Pro Val  Phe Gly Cys Ala Gln  Val Pro Arg
    1160                1165                1170

Arg Ala  Gly Met Asp His Gly  Gln Asp Ala Val Cys  Glu Phe Ile
    1175                1180                1185
```

-continued

```
Ala Thr Pro Val Ala Thr Asp Ile Asn Tyr Phe Arg Arg Pro Cys
    1190            1195                1200

Asn Pro Arg Gly Arg Ala Ala Gly Gly Val Tyr Ala Gly Asp Lys
    1205            1210                1215

Glu Gly Asp Val Ile Ala Leu Met Tyr Asp His Gly Gln Ser Asp
    1220            1225                1230

Pro Ala Arg Pro Phe Ala Ala Thr Ala Asn Pro Trp Ala Ser Gln
    1235            1240                1245

Arg Phe Ser Tyr Gly Asp Leu Leu Tyr Asn Gly Ala Tyr His Leu
    1250            1255                1260

Asn Gly Ala Ser Pro Val Leu Ser Pro Cys Phe Lys Phe Phe Thr
    1265            1270                1275

Ala Ala Asp Ile Thr Ala Lys His Arg Cys Leu Glu Arg Leu Ile
    1280            1285                1290

Val Glu Thr Gly Ser Ala Val Ser Thr Ala Thr Ala Ala Ser Asp
    1295            1300                1305

Val Gln Phe Lys Arg Pro Pro Gly Cys Arg Glu Leu Val Glu Asp
    1310            1315                1320

Pro Cys Gly Leu Phe Gln Glu Ala Tyr Pro Ile Thr Cys Ala Ser
    1325            1330                1335

Asp Pro Ala Leu Leu Arg Ser Ala Arg Asp Gly Glu Ala His Ala
    1340            1345                1350

Arg Glu Thr His Phe Thr Gln Tyr Leu Ile Tyr Asp Ala Ser Pro
    1355            1360                1365

Leu Lys Gly Leu Ser Leu
    1370

<210> SEQ ID NO 5
<211> LENGTH: 585
<212> TYPE: PRT
<213> ORGANISM: Herpes Simplex Virus 2

<400> SEQUENCE: 5

Met Asp Pro Tyr Tyr Pro Phe Asp Ala Leu Asp Val Trp Glu His Arg
1               5                   10                  15

Arg Phe Ile Val Ala Asp Ser Arg Ser Phe Ile Thr Pro Glu Phe Pro
                20                  25                  30

Arg Asp Phe Trp Met Leu Pro Val Phe Asn Ile Pro Arg Glu Thr Ala
            35                  40                  45

Ala Glu Arg Ala Ala Val Leu Gln Ala Gln Arg Thr Ala Ala Ala Ala
        50                  55                  60

Ala Leu Glu Asn Ala Ala Leu Gln Ala Ala Glu Leu Pro Val Asp Ile
65                  70                  75                  80

Glu Arg Arg Ile Arg Pro Ile Glu Gln Gln Val His His Ile Ala Asp
                85                  90                  95

Ala Leu Glu Ala Leu Glu Thr Ala Ala Ala Ala Glu Glu Ala Asp
            100                 105                 110

Ala Ala Arg Asp Ala Glu Ala Arg Gly Glu Gly Ala Ala Asp Gly Ala
        115                 120                 125

Ala Pro Ser Pro Thr Ala Gly Pro Ala Ala Ala Glu Met Glu Val Gln
    130                 135                 140

Ile Val Arg Asn Asp Pro Pro Leu Arg Tyr Asp Thr Asn Leu Pro Val
145                 150                 155                 160

Asp Leu Leu His Met Val Tyr Ala Gly Arg Gly Ala Ala Gly Ser Ser
```

```
            165                 170                 175
Gly Val Val Phe Gly Thr Trp Tyr Arg Thr Ile Gln Glu Arg Thr Ile
            180                 185                 190
Ala Asp Phe Pro Leu Thr Thr Arg Ser Ala Asp Phe Arg Asp Gly Arg
            195                 200                 205
Met Ser Lys Thr Phe Met Thr Ala Leu Val Leu Ser Leu Gln Ser Cys
            210                 215                 220
Gly Arg Leu Tyr Val Gly Gln Arg His Tyr Ser Ala Phe Glu Cys Ala
225                 230                 235                 240
Val Leu Cys Leu Tyr Leu Leu Tyr Arg Thr Thr His Glu Ser Ser Pro
            245                 250                 255
Asp Arg Asp Arg Ala Pro Val Ala Phe Gly Asp Leu Leu Ala Arg Leu
            260                 265                 270
Pro Arg Tyr Leu Ala Arg Leu Ala Ala Val Ile Gly Asp Glu Ser Gly
            275                 280                 285
Arg Pro Gln Tyr Arg Tyr Arg Asp Asp Lys Leu Pro Lys Ala Gln Phe
            290                 295                 300
Ala Ala Ala Gly Gly Arg Tyr Glu His Gly Ala Leu Ala Thr His Val
305                 310                 315                 320
Val Ile Ala Thr Leu Val Arg His Gly Val Leu Pro Ala Ala Pro Gly
            325                 330                 335
Asp Val Pro Arg Asp Thr Ser Thr Arg Val Asn Pro Asp Val Ala
            340                 345                 350
His Arg Asp Asp Val Asn Arg Ala Ala Ala Phe Leu Ala Arg Gly
            355                 360                 365
His Asn Leu Phe Leu Trp Glu Asp Gln Thr Leu Leu Arg Ala Thr Ala
            370                 375                 380
Asn Thr Ile Thr Ala Leu Ala Val Leu Arg Arg Leu Leu Ala Asn Gly
385                 390                 395                 400
Asn Val Tyr Ala Asp Arg Leu Asp Asn Arg Leu Gln Leu Gly Met Leu
            405                 410                 415
Ile Pro Gly Ala Val Pro Ala Glu Ala Ile Ala Arg Gly Ala Ser Gly
            420                 425                 430
Leu Asp Ser Gly Ala Ile Lys Ser Gly Asp Asn Asn Leu Glu Ala Leu
            435                 440                 445
Cys Val Asn Tyr Val Leu Pro Leu Tyr Gln Ala Asp Pro Thr Val Glu
            450                 455                 460
Leu Thr Gln Leu Phe Pro Gly Leu Ala Ala Leu Cys Leu Asp Ala Gln
465                 470                 475                 480
Ala Gly Arg Pro Leu Ala Ser Thr Arg Val Val Asp Met Ser Ser
            485                 490                 495
Gly Ala Arg Gln Ala Ala Leu Val Arg Leu Thr Ala Leu Glu Leu Ile
            500                 505                 510
Asn Arg Thr Arg Thr Asn Thr Thr Pro Val Gly Glu Ile Ile Asn Ala
            515                 520                 525
His Asp Ala Leu Gly Ile Gln Tyr Glu Gln Gly Leu Gly Leu Leu Ala
            530                 535                 540
Gln Gln Ala Arg Ile Gly Leu Ala Ser Asn Ala Lys Arg Phe Ala Thr
545                 550                 555                 560
Phe Asn Val Gly Ser Asp Tyr Asp Leu Leu Tyr Phe Leu Cys Leu Gly
            565                 570                 575
Phe Ile Pro Gln Tyr Leu Ser Val Ala
            580                 585
```

<210> SEQ ID NO 6
<211> LENGTH: 696
<212> TYPE: PRT
<213> ORGANISM: Herpes Simplex Virus 2

<400> SEQUENCE: 6

Met Ser Val Arg Gly His Ala Val Arg Arg Arg Ala Ser Thr Arg
1               5                   10                  15

Ser His Ala Pro Ser Ala His Arg Ala Asp Ser Pro Val Glu Asp Glu
                20                  25                  30

Pro Glu Gly Gly Gly Gly Gly Leu Met Gly Tyr Leu Arg Ala Val Phe
            35                  40                  45

Asn Val Asp Asp Asp Ser Glu Val Glu Ala Ala Gly Glu Met Ala Ser
50                  55                  60

Glu Glu Pro Pro Pro Arg Arg Arg Glu Ala Arg Gly His Pro Gly
65                  70                  75                  80

Ser Arg Arg Ala Ser Glu Ala Arg Ala Ala Pro Pro Arg Arg Ala
                85                  90                  95

Ser Phe Pro Arg Pro Arg Ser Val Thr Ala Arg Ser Gln Ser Val Arg
                100                 105                 110

Gly Arg Arg Asp Ser Ala Ile Thr Arg Ala Pro Arg Gly Gly Tyr Leu
            115                 120                 125

Gly Pro Met Asp Pro Arg Asp Val Leu Gly Arg Val Gly Gly Ser Arg
    130                 135                 140

Val Val Pro Ser Pro Leu Phe Leu Asp Glu Leu Ser Tyr Glu Glu Asp
145                 150                 155                 160

Asp Tyr Pro Ala Ala Val Ala His Asp Gly Ala Gly Ala Arg Pro
                165                 170                 175

Pro Ala Thr Val Glu Ile Leu Ala Gly Arg Val Ser Gly Pro Glu Leu
            180                 185                 190

Gln Ala Ala Phe Pro Leu Asp Arg Leu Thr Pro Arg Val Ala Ala Trp
        195                 200                 205

Asp Glu Ser Val Arg Ser Ala Leu Ala Leu Gly His Pro Ala Gly Phe
    210                 215                 220

Tyr Pro Cys Pro Asp Ser Ala Phe Gly Leu Ser Arg Val Gly Val Met
225                 230                 235                 240

His Phe Ala Ser Pro Ala Asp Pro Lys Val Phe Phe Arg Gln Thr Leu
                245                 250                 255

Gln Gln Gly Glu Ala Leu Ala Trp Tyr Val Thr Gly Asp Ala Ile Leu
            260                 265                 270

Asp Leu Thr Asp Arg Arg Ala Lys Thr Ser Pro Ser Arg Ala Met Gly
        275                 280                 285

Phe Leu Val Asp Ala Ile Val Arg Val Ala Ile Asn Gly Trp Val Cys
    290                 295                 300

Gly Thr Arg Leu His Thr Glu Gly Arg Gly Ser Glu Leu Asp Asp Arg
305                 310                 315                 320

Ala Ala Glu Leu Arg Arg Gln Phe Ala Ser Leu Thr Ala Leu Arg Pro
                325                 330                 335

Val Gly Ala Ala Ala Val Pro Leu Leu Ser Ala Gly Ala Ala Pro
            340                 345                 350

Pro His Pro Gly Pro Asp Ala Ala Val Phe Arg Ser Ser Leu Gly Ser
        355                 360                 365

Leu Leu Tyr Trp Pro Gly Val Arg Ala Leu Leu Gly Arg Asp Cys Arg

```
                  370                 375                 380
    Val Ala Arg Tyr Ala Gly Arg Met Thr Tyr Ile Ala Thr Gly Ala
    385                 390                 395                 400

Leu Leu Ala Arg Phe Asn Pro Gly Ala Val Lys Cys Val Leu Pro Arg
                    405                 410                 415

Glu Ala Ala Phe Ala Gly Arg Val Leu Asp Val Leu Ala Val Leu Ala
                    420                 425                 430

Glu Gln Thr Val Gln Trp Leu Ser Val Val Gly Ala Arg Leu His
                    435                 440                 445

Pro His Ser Ala His Pro Ala Phe Ala Asp Val Glu Gln Glu Ala Leu
                    450                 455                 460

Phe Arg Ala Leu Pro Leu Gly Ser Pro Gly Val Val Ala Ala Glu His
    465                 470                 475                 480

Glu Ala Leu Gly Asp Thr Ala Ala Arg Arg Leu Leu Ala Thr Ser Gly
                    485                 490                 495

Leu Asn Ala Val Leu Gly Ala Ala Val Tyr Ala Leu His Thr Ala Leu
                    500                 505                 510

Ala Thr Val Thr Leu Lys Tyr Ala Leu Ala Cys Gly Asp Ala Arg Arg
                    515                 520                 525

Arg Arg Asp Asp Ala Ala Ala Ala Arg Ala Val Leu Ala Thr Gly Leu
                    530                 535                 540

Ile Leu Gln Arg Leu Leu Gly Leu Ala Asp Thr Val Val Ala Cys Val
    545                 550                 555                 560

Ala Leu Ala Ala Phe Asp Gly Gly Ser Thr Ala Pro Glu Val Gly Thr
                    565                 570                 575

Tyr Thr Pro Leu Arg Tyr Ala Cys Val Leu Arg Ala Thr Gln Pro Leu
                    580                 585                 590

Tyr Ala Arg Thr Thr Pro Ala Lys Phe Trp Ala Asp Val Arg Ala Ala
                    595                 600                 605

Ala Glu His Val Asp Leu Arg Pro Ala Ser Ser Ala Pro Arg Ala Pro
                    610                 615                 620

Val Ser Gly Thr Ala Asp Pro Ala Phe Leu Leu Glu Asp Leu Ala Ala
    625                 630                 635                 640

Phe Pro Pro Ala Pro Leu Asn Ser Glu Ser Val Leu Gly Pro Arg Val
                    645                 650                 655

Arg Val Val Asp Ile Met Ala Gln Phe Arg Lys Leu Leu Met Gly Asp
                    660                 665                 670

Glu Glu Thr Ala Ala Leu Arg Ala His Val Ser Gly Arg Arg Ala Thr
                    675                 680                 685

Gly Leu Gly Gly Pro Pro Arg Pro
                    690                 695

<210> SEQ ID NO 7
<211> LENGTH: 15
<212> TYPE: PRT
<213> ORGANISM: Herpes simplex virus 2

<400> SEQUENCE: 7

Gln Pro Arg Trp Ser Tyr Tyr Asp Ser Phe Ser Ala Val Ser Glu
1               5                   10                  15

<210> SEQ ID NO 8
<211> LENGTH: 15
<212> TYPE: PRT
<213> ORGANISM: Herpes Simplex Virus 2
```

<400> SEQUENCE: 8

Ser Gln Ile Pro Pro Asn Trp His Ile Pro Ser Ile Gln Asp Val
1               5                   10                  15

<210> SEQ ID NO 9
<211> LENGTH: 15
<212> TYPE: PRT
<213> ORGANISM: Herpes Simplex Virus 2

<400> SEQUENCE: 9

Asn Tyr Phe Ser Ser Ile Arg Gln Pro Val Val Gln His Ala Arg
1               5                   10                  15

<210> SEQ ID NO 10
<211> LENGTH: 15
<212> TYPE: PRT
<213> ORGANISM: Herpes Simplex Virus 2

<400> SEQUENCE: 10

Cys Glu Phe Ile Ala Thr Pro Val Ala Thr Asp Ile Asn Tyr Phe
1               5                   10                  15

<210> SEQ ID NO 11
<211> LENGTH: 15
<212> TYPE: PRT
<213> ORGANISM: Herpes Simplex Virus 2

<400> SEQUENCE: 11

Met Asp Pro Tyr Tyr Pro Phe Asp Ala Leu Asp Val Trp Glu His
1               5                   10                  15

<210> SEQ ID NO 12
<211> LENGTH: 604
<212> TYPE: PRT
<213> ORGANISM: Herpes Simplex Virus 2

<400> SEQUENCE: 12

Arg Leu Ser Met Glu Asn Ala Val Gly Thr Val Cys His Pro Ser Leu
1               5                   10                  15

Met Asn Ile Asp Ala Ala Val Gly Gly Val Asn His Asp Pro Val Glu
                20                  25                  30

Ala Ala Asn Pro Tyr Gly Ala Tyr Val Ala Pro Ala Gly Pro Gly
            35                  40                  45

Ala Asp Met Gln Gln Arg Phe Leu Asn Ala Trp Arg Gln Arg Leu Ala
        50                  55                  60

His Gly Arg Val Arg Trp Val Ala Glu Cys Gln Met Thr Ala Glu Gln
65                  70                  75                  80

Phe Met Gln Pro Asp Asn Ala Asn Leu Ala Leu Glu Leu His Pro Ala
                85                  90                  95

Phe Asp Phe Phe Ala Gly Val Ala Asp Val Glu Leu Pro Gly Gly Glu
            100                 105                 110

Val Pro Pro Ala Gly Pro Gly Ala Ile Gln Ala Thr Trp Arg Val Val
        115                 120                 125

Asn Gly Asn Leu Pro Leu Ala Leu Cys Pro Val Ala Phe Arg Asp Ala
    130                 135                 140

Arg Gly Leu Glu Leu Gly Val Gly Arg His Ala Met Ala Pro Ala Thr
145                 150                 155                 160

Ile Ala Ala Val Arg Gly Ala Phe Glu Asp Arg Ser Tyr Pro Ala Val
                165                 170                 175

```
Phe Tyr Leu Leu Gln Ala Ala Ile His Gly Asn Glu His Val Phe Cys
                180                 185                 190

Ala Leu Ala Arg Leu Val Thr Gln Cys Ile Thr Ser Tyr Trp Asn Asn
            195                 200                 205

Thr Arg Cys Ala Ala Phe Val Asn Asp Tyr Ser Leu Val Ser Tyr Ile
        210                 215                 220

Val Thr Tyr Leu Gly Gly Asp Leu Pro Glu Glu Cys Met Ala Val Tyr
225                 230                 235                 240

Arg Asp Leu Val Ala His Val Glu Ala Leu Ala Gln Leu Val Asp Asp
                245                 250                 255

Phe Thr Leu Pro Gly Pro Glu Leu Gly Gly Gln Ala Gln Ala Glu Leu
                260                 265                 270

Asn His Leu Met Arg Asp Pro Ala Leu Leu Pro Pro Leu Val Trp Asp
            275                 280                 285

Cys Asp Gly Leu Met Arg His Ala Ala Leu Asp Arg His Arg Asp Cys
290                 295                 300

Arg Ile Asp Ala Gly Gly His Glu Pro Val Tyr Ala Ala Ala Cys Asn
305                 310                 315                 320

Val Ala Thr Ala Asp Phe Asn Arg Asn Asp Gly Arg Leu Leu His Asn
                325                 330                 335

Thr Gln Ala Arg Ala Ala Asp Ala Ala Asp Asp Arg Pro His Arg Pro
            340                 345                 350

Ala Asp Trp Thr Val His His Lys Ile Tyr Tyr Tyr Val Leu Val Pro
        355                 360                 365

Ala Phe Ser Arg Gly Arg Cys Cys Thr Ala Gly Val Arg Phe Asp Arg
370                 375                 380

Val Tyr Ala Thr Leu Gln Asn Met Val Val Pro Glu Ile Ala Pro Gly
385                 390                 395                 400

Glu Glu Cys Pro Ser Asp Pro Val Thr Asp Pro Ala His Pro Leu His
                405                 410                 415

Pro Ala Asn Leu Val Ala Asn Thr Val Lys Arg Met Phe His Asn Gly
            420                 425                 430

Arg Val Val Asp Gly Pro Ala Met Leu Thr Leu Gln Val Leu Ala
        435                 440                 445

His Asn Met Ala Glu Arg Thr Thr Ala Leu Leu Cys Ser Ala Ala Pro
450                 455                 460

Asp Ala Gly Ala Asn Thr Ala Ser Thr Ala Asn Met Arg Ile Phe Asp
465                 470                 475                 480

Gly Ala Leu His Ala Gly Val Leu Leu Met Ala Pro Gln His Leu Asp
                485                 490                 495

His Thr Ile Gln Asn Gly Glu Tyr Phe Tyr Val Leu Pro Val His Ala
            500                 505                 510

Leu Phe Ala Gly Ala Asp His Val Ala Asn Ala Pro Asn Phe Pro Pro
        515                 520                 525

Ala Leu Arg Asp Leu Ala Arg Asp Val Pro Leu Val Pro Pro Ala Leu
530                 535                 540

Gly Ala Asn Tyr Phe Ser Ser Ile Arg Gln Pro Val Val Gln His Ala
545                 550                 555                 560

Arg Glu Ser Ala Ala Gly Glu Asn Ala Leu Thr Tyr Ala Leu Met Ala
                565                 570                 575

Gly Tyr Phe Lys Met Ser Pro Val Ala Leu Tyr His Gln Leu Lys Thr
            580                 585                 590

Gly Leu His Pro Gly Phe Gly Phe Thr Val Val Arg
```

<210> SEQ ID NO 13
<211> LENGTH: 683
<212> TYPE: DNA
<213> ORGANISM: Human immunodeficiency virus type 1

<400> SEQUENCE: 13

```
cctagaaaaa catggagcaa tcacaagtag caatacagca gctaccaatg ctgattgtgc      60
ctggctagaa gcacaagagg aggaggaggt gggttttcca gtcacacctc aggtaccttt     120
aagaccaatg acttacaagg cagctgtaga tcttagccac ttttttaaaag aaaaggggggg     180
actggaaggg ctaattcact cccaacgaag acaagatatc cttgatctgt ggatctacca     240
cacacaaggc tacttccctg attggcagaa ctacacacca gggccaggga tcagatatcc     300
actgaccttt ggatggtgct acaagctagt accagttgag caagagaagg tagaagaagc     360
caatgaagga gagaacaccc gcttgttaca ccctgtgagc ctgcatggga tggatgaccc     420
ggagagagaa gtattagagt ggaggtttga cagccgccta gcatttcatc acatggcccg     480
agagctgcat ccggactgta ctgggtctct ctggttagac cagatctgag cctgggagct     540
ctctggctaa ctagggaacc cactgcttaa gcctcaataa agcttgcctt gagtgcttca     600
agtagtgtgt gcccgtctgt tgtgtgactc tggtaactag agatccctca gacccttta      660
gtcagtgtgg aaaatctcta gca                                             683
```

<210> SEQ ID NO 14
<211> LENGTH: 416
<212> TYPE: DNA
<213> ORGANISM: Human immunodeficiency virus type 1

<400> SEQUENCE: 14

```
cctagaaaaa catggagcaa tcacaagtag caatacagca gctaccaatg ctgattgtgc      60
ctggctagaa gcacaagagg aggaggaggt gggttttcca gtcacacctc aggtaccttt     120
aagaccaatg acttacaagg cagctgtaga tcttagccac ttttttaaaag aaaaggggggg     180
actggaaggg ctaattcact cccaacgaag acaagatctg cttttttgcct gtactgggtc     240
tctctggtta gaccagatct gagcctggga gctctctggc taactaggga acccactgct     300
taagcctcaa taagcttgcc ttgagtgct tcaagtagtg tgtgcccgtc tgttgtgtga     360
ctctggtaac tagagatccc tcagaccctt ttagtcagtg tggaaaatct ctagca         416
```

<210> SEQ ID NO 15
<211> LENGTH: 401
<212> TYPE: DNA
<213> ORGANISM: Human immunodeficiency virus type 1

<400> SEQUENCE: 15

```
cctagaaaaa catggagcaa tcacaagtag caatacagca gctaccaatg ctgattgtgc      60
ctggctagaa gcacaagagg aggaggaggt gggttttcca gtcacacctc aggtaccttt     120
aagaccaatg acttacaagg cagctgtaga tcttagccac ttttactgg aagggctaat     180
tcactcccaa cgaagacaag atctgctttt tgcctgtact gggtctctct ggttagacca     240
gatctgagcc tgggagctct ctggctaact agggaaccca ctgcttaagc ctcaataaag     300
cttgccttga gtgcttcaag tagtgtgtgc ccgtctgttg tgtgactctg gtaactagag     360
atccctcaga cccttttagt cagtgtggaa aatctctagc a                         401
```

-continued

<210> SEQ ID NO 16
<211> LENGTH: 4
<212> TYPE: PRT
<213> ORGANISM: HSV-2 fragment

<400> SEQUENCE: 16

Cys Ala Lys Tyr
1

<210> SEQ ID NO 17
<211> LENGTH: 4
<212> TYPE: PRT
<213> ORGANISM: HSV-2 modified fragment

<400> SEQUENCE: 17

Gly Leu Ala Val
1

VACCINES FOR HSV-2

CROSS REFERENCE TO RELATED APPLICATIONS

This application claims the benefit under 35 U.S.C. § 119(e) of U.S. Provisional Patent Application Nos. 61/647,764, filed May 16, 2012, 61/679,387, filed Aug. 3, 2012, and 61/714,158, filed Oct. 15, 2012, all of which are incorporated herein by reference in their entirety.

REFERENCE TO SEQUENCE LISTING

The sequence listing of this patent application is provided separately in a file named "47733A_SeqListing.txt". The content of this file, which was created on 16 May 2013, and consists of 45,969 bytes, is incorporated in its entirety.

TECHNICAL FIELD

Vaccines for herpes simplex virus-2 infection and related methods and compositions.

BACKGROUND

HSV-2 (herpes simplex virus-2) is a member of the family Herpetoviridae, a group of DNA viruses that often result in skin lesions (e.g., chickenpox and fever blisters) and are characterized by latent and recurrent infections. HSV-2 is the leading cause of genital ulcers, which can manifest as a cluster of small fluid-filled blisters that rupture and form painful sores, taking several weeks to heal. Additional symptoms may include fever, general sick feeling, muscle aches, painful urination, vaginal discharge, and enlarged, tender lymph nodes in the groin area. Recurring outbreaks are likely. The virus can exist in nerve cells for the life time of the infected subject and reactivate, forming skin ulcers, at irregular intervals. Even in the absence of actual ulcers, the virus can be produced and spread from individual to individual. It is presently incurable.

Genital herpes is the most prevalent sexually transmitted disease. In the United States, over 16% of the population, or about one out of six people, is infected with HSV-2, with a disproportionate burden on women—approximately 20% of women and 12% of men—and on African-Americans—about 40% of the population and nearly 50% of African-American women. (Morbidity and Mortality Weekly Report, 59: 456-459, Apr. 23, 2010). Altogether, about 50 million people in the U.S. are infected, of which about 80% are unaware of their infection, but may still be infectious. Elsewhere in the world, HSV-2 also attains epidemic proportions. A WHO team estimated that in 2003, 536 million people world-wide were infected, and new infections were occurring at about 23 million yearly (Looker et al., Bull World Health Organ. 86: 805-812, 2008). Although prevalence varied by region, generally prevalence increased with age and was higher among women than among men. In addition, HSV-2 prevalence is higher in developing countries than in developed countries—with the exceptions of North America, which has a high HSV-2 prevalence, and south Asia, which has a relatively low HSV-2 prevalence. The highest prevalence is found in Sub-Saharan Africa where nearly 80% of women and 45% of men are infected with HSV-2. Other regions, notably eastern Asia and southeast Asia, approach this level. In addition to sexual transmission, HSV-2 can be transmitted from a woman to a baby, typically at the time of delivery. Concomitant with the HSV-2 epidemic in the adult U.S. population, the incidence of neonatal infection has also dramatically increased. About 1,800 cases of neonatal HSV infection occur yearly in the U.S., which is a higher number of cases than neonatal HIV infection.

The health implications of HSV-2 infection are staggering. Although the vast majority of infected individuals are asymptomatic, virus can still be transmitted. Those with symptoms suffer painful sores on their genitals and anal region and often flu-like symptoms such as fever and swollen glands. Unfortunately, those with a first outbreak of HSV-2 are likely to have several additional outbreaks (typically four or five) within the first year alone. Regardless of the severity of symptoms, knowledge of infection often causes stress and can negatively impact quality of life (Rosenthal, et al., Sex Transm Infect. 82: 154, 2006; Crosby et al Sex Health, 5:279-283, 2008). In neonates infected with HSV-2, neonatal encephalitis from HSV infection has a mortality of >15% even with treatment, and the neurological morbidity among HSV-2 infected infants is an additional 30-50% of surviving cases Coupled with the high prevalence of HSV-2, there is a stark realization that HSV-2 infection substantially increases the risk for HIV-1 acquisition and transmission. Data from Africa show that HSV-2 infection can increase the risk for HIV transmission by as much as seven-fold and that up to one-half of newly acquired HIV cases are directly attributed to HSV-2 infection. Overall, the relative risk of HIV acquisition increases more than two-fold in HSV-2-infected individuals. The synergistic effect on HIV acquisition is greater for HSV-2 than for any other sexually transmitted infection, underscoring the need for an effective public health strategy capable of minimizing the effects of the current HSV-2 epidemic.

The increasing prevalence of HSV-2 in the adult and pediatric populations persists despite the widespread use of pharmacological intervention. Antiviral medication, such as acyclovir, given at high doses early in infection can reduce HSV transmission, but this does not prevent latent infection of the neuronal ganglion. Antiviral therapy has many drawbacks, including as side effects nausea, vomiting, rashes, and decreased kidney function, and should be used with caution because they can be teratogenic as well as be toxic to developing embryos. Furthermore, continuous suppressive administration with valcyclovir reduced HSV transmission by less than 50% despite early intervention. Even if this level of effect were acceptable, the approach is impractical considering the high cost and that 80% of those infected are unaware of their status. Alternatives to antiviral drugs, such as topical microbicides are unproven clinically, and physical barriers (e.g., condoms) have marginal "real-world" efficacy. For these reasons, vaccination is essential for combating and diminishing the health impact of HSV-2 infection.

The first vaccine for HSV was developed in the 1920s, and since then, a variety of vaccine approaches have been tried—all to no avail. The conventional, time-honored types of vaccines including whole, inactivated virus, attenuated live virus, modified live virus, and cell culture-derived subunits were largely unsuccessful or had low efficacy (Stanberry, Herpes 11 (Suppl 3) 161A-169A, 2004). With the advent of recombinant DNA technology, recombinant subunit vaccines have been developed. These vaccines comprised one or two of the envelope glycoproteins in combination with adjuvants. The glycoproteins were attractive candidates mainly because they are the targets of neutralizing antibodies and they are highly conserved among HSV-2 strains. In the last decade, extensive clinical trials on two candidate vaccines, one developed by Chiron and the other by GlaxoSmithKline, were both halted due to insufficient efficacy. Chiron's vaccine comprised truncated forms of two HSV-2 glycoproteins, gD2 and gB2, in combination with the adjuvant MF59. The vaccine at best provided transient protection against HSV-2 although high titers of antibodies to HSV-2 were generated (Stanberry, ibid). GlaxoSmithKline (GSK) developed and tested a similar vaccine; however it contained only a single glycoprotein, gD2, and alum and MPL as adjuvants. Following eight years of studies and clinical trials, GSK pronounced it as a failure in October 2010. The vaccine was unsuccessful in preventing infection in seronegative women, the only group in early clinical trials that had seemed to benefit.

SUMMARY

The claimed invention is directed to compositions and methods useful in preventing or treating HSV-2 (herpes simplex virus 2) infections in subjects, preferably humans, in one embodiment the human is female, while in another embodiment the human is male. The compositions comprise (i) an envelope glycoprotein of HSV-2 or an immunogenic fragment of the HSV-2 envelope glycoprotein, (ii) an HSV-2 structural protein or immunogenic fragment of the HSV-2 structural protein, wherein the structural protein is not one of the envelope glycoproteins, (iii) an agent that activates innate immunity in a subject and (iv) a pharmaceutically acceptable carrier. In certain embodiments, the envelope glycoprotein is gD2 and the composition has either gD2 or in an alternative embodiment, an immunogenic fragment derived from gD2. In some embodiments, the structural protein is one or more of UL47, ICP0, ICP4, ICP47, UL5, UL8, UL15, UL19, UL25, UL30, UL32, UL46, UL39 (ICP10), UL7, UL40, UL54 and UL26 and if immunogenic fragments are present, they are derived from UL47, ICP0, ICP4, ICP47, UL5, UL8, UL15, UL19, UL25, UL30, UL32, UL46, UL39 (ICP10), UL7, UL40, UL54 and/or UL26. It is understood that the exact sequence of a protein may vary from one herpesvirus to another, and thus all references to an HSV-2 protein encompasses any such protein obtainable from any naturally occurring HSV-2. In other embodiments, both UL19 and UL25, or fragments from UL19 (e.g. SEQ ID NO. 12, a type of Upper Domain Fragment) and UL25, or a mixture of whole protein and fragments are present, e.g. a mixture of full length UL25 and a fragment of UL19, e.g., SEQ ID NO. 12, optionally with UL47 or a fragment thereof. At times, the agent that activates innate immunity is an adjuvant. In particular the adjuvant can be GLA or another MALA adjuvant. In one embodiment the immunogenic, pharmaceutical composition comprises gD2, GLA or another MALA adjuvant, and two or three antigens selected from full length or fragments of UL25, UL19, and UL47, and a pharmaceutically acceptable carrier. In related embodiments, the immunogenic, pharmaceutical composition comprises a MALA adjuvant, preferably GLA having the structural formula of FIG. 1, gD2, UL25, UL19 Upper Domain Fragment, and a pharmaceutically acceptable carrier; optionally such a composition further comprises one or more additional HSV-2 structural proteins, or fragments thereof.

In some embodiments, the compositions comprise an antigenic portion of an envelope glycoprotein of HSV-2 and a pharmaceutically acceptable carrier. The terms "immunogenic fragment" and "immunological fragment" and "antigenic portion" are used interchangeably herein to designate fragments or portions of proteins that elicit an antibody response or a cellular cytotoxic response that retains specificity for (cross-reactivity with) the full length protein. In certain embodiments, the antigenic portion binds to neutralizing antibodies. In certain embodiments, the antigenic portion is from gD2 or gB2, and in other embodiments, the antigenic portion, whether from gD2, gB2 or another envelope glycoprotein, comprises at least part and optionally all of the leader sequence. In any of the embodiments, the antigenic portion comprises two or more linear epitopes or comprises two or more discontinuous epitopes from the envelope glycoprotein. In any of the embodiments, the composition further comprises an agent that activates innate immunity. The agent may be an adjuvant, such as GLA as disclosed in, for example, US Publication No. 2009/0181078.

The methods can be used to treat an HSV-2 infection or to generate an immune response, which may prevent or ameliorate an HSV-2 infection. Suitable subjects for the methods include those who are seropositive for HSV-2 as well as those who are seronegative for HSV-2. In the methods, one of the compositions described herein is administered to a subject.

Some exemplary statements of the present invention are set forth as follows, using the designation (xy) where each of x and y denote a letter, the designation denoting an embodiment, or group of embodiments when more than one (xy) is identified within an embodiment. (AA) An immunogenic, pharmaceutical composition comprising (i) an envelope glycoprotein of HSV-2, or an immunological fragment thereof; (ii) a structural protein of HSV-2 other than an envelope glycoprotein of HSV-2, or an immunological fragment thereof; (iii) an agent that activates innate immunity; and (iv) a pharmaceutically acceptable carrier. (AB) Composition (AA) wherein the envelope glycoprotein of HSV-2 is gD2, and the composition comprises gD2. (AC) Composition (AA) wherein the composition comprises an immunological fragment of gD2. (AD) A composition of any one or more of (AA), (AB) and (AC), wherein the structural protein of HSV-2 is one or more proteins selected from the group consisting of UL47, ICP0, UL25, UL46, UL39, UL7, and UL26. (AE) Composition (AA) wherein the structural protein of HSV-2 is UL19. (AF) The composition of (AB) wherein the structural protein of HSV-2 is UL19. (AG) Composition (AA) wherein the structural protein of HSV-2 is an immunological fragment of UL19, e.g., SEQ ID NO. 12. (AH) Composition (AB) wherein the structural protein of HSV-2 is an immunological fragment thereof UL47. (AI) Composition (AA) wherein the structural protein of HSV-2 is UL25. (AJ) Composition (AB) wherein the structural protein of HSV-2 is UL25. (AK) Composition (AA) wherein the structural protein of HSV-2 is an immunological fragment of UL25. (AL) Composition (AB) wherein the structural protein of HSV-2 is ICP0. (AM) Composition (AA) wherein the structural protein of HSV-2 is UL47. (AN) Composition (AB) wherein the structural protein of HSV-2 is a fragment of UL47. (AO) Composition (AA) wherein the structural protein of HSV-2 other than an envelope glycoprotein of HSV-2 is UL47, and is an immunological fragment thereof. (AP) Composition (AB) wherein the structural protein of HSV-2 other than an envelope glycoprotein of HSV-2 is UL47, and is an immunological fragment thereof. (AQ) A composition of any one or more of (AA), (AB), (AC), (AD), (AE), (AF), (AG), (AH), (AI), (AJ), (AK), (AL), (AM), (AN), (AO), (AP) further comprising a second structural protein of HSV-2 other than an envelope glycoprotein of HSV-2, or an immunological fragment thereof. (AR) Composition (AQ) wherein the second structural protein of HSV-2 other than an envelope glycoprotein of HSV-2 is selected from the group consisting of UL19, UL25 and UL47, where the second structural protein is non-identical to the structural protein. (AS) Composition (AR) comprising the second structural protein. (AT) Composition (AR) comprising an immunological fragment of the second structural protein. (AU) A composition of any one or more of (AE), (AF), (AG) and/or (AH) further comprising UL25. (AV) A composition of any one or more of (AE), (AF), (AG) and/or (AH) further comprising an immunological fragment of UL25. (AW) A composition of any one or more of (AE), (AF), (AG) and/or (AH) further comprising UL47. (AX) A composition of any one or more of (AE), (AF), (AG) and/or (AH) further comprising an immunological fragment of UL47. (AY) A composition of any one or more of (AI), (AJ), (AK) and/or (AL) further comprising UL19. (AZ) A composition of any one or more of (AI), (AJ), (AK) and/or (AL) further comprising an immunological fragment of UL19, e.g., SEQ ID NO 12. (BA) A composition of any one or more of (AI), (AJ), (AK) and/or (AL) further comprising UL47. (BB) A composition of any one or more of (AI), (AJ), (AK) and/or (AL) further comprising an immunological fragment of UL47. (BC) A composition of any one or more of (AM), (AN), (AO) and/or (AP) further comprising UL19. (BD) A composition of any one or more of (AM), (AN), (AO) and/or (AP) further comprising an immunological fragment of UL19. (BE) A composition of any one or more of (AM), (AN), (AO) and/or (AP) further comprising UL25. (BF) A composition of any one or more of (AM), (AN), (AO) and/or (AP) further comprising an immunological fragment of UL25. (BG) A composition of any one or more of (AA), (AB), (AC), (AD), (AE), (AF), (AG), (AH), (AI), (AJ), (AK), (AL), (AM), (AN), (AO), (AP), (AQ), (AR), (AS), (AT), (AU), (AV), (AW), (AX), (AY), (AZ), (BA), (BB), (BC), (BD), (BE), and (BF) wherein the agent is an adjuvant. (BH) A composition selected from (BG) wherein the adjuvant is GLA or another MALA adjuvant, and each and every one of the options in (BG) is independently selected as a distinct embodiment of the present invention. (BI) Composition (AA) comprising gD2; UL25; UL19; GLA or another MALA adjuvant; and a pharmaceutically acceptable carrier. (BJ) Composition (AA) comprising gD2, UL25 and an immunological fragment of UL19. (BK) Composition (AA) comprising gD2, UL19, and an immunological fragment of UL25. (BL) A composition of any one or more of (BI), (BJ) and (BK) further comprising UL47. (BM) A composition of any one or more of (BI), (BJ) and (BK) further comprising an immunological fragment of UL47. (BN) A method for treating an HSV-2 infection in a subject, comprising administering the composition of any one or more of (AA), (AB), (AC), (AD), (AE), (AF), (AG), (AH), (AI), (AJ), (AK), (AL), (AM), (AN), (AO), (AP), (AQ), (AR), (AS), (AT), (AU), (AV), (AW), (AX), (AY), (AZ), (BA), (BB), (BC), (BD), (BE), (BF), (BG), (BH), (BI), (BJ), (BK), (BL), and (BM) to the subject. (BO) A method for generating an immune response to HSV-2 in a subject, comprising administering the composition of any one or more of (AA), (AB), (AC), (AD), (AE), (AF), (AG), (AH), (AI), (AJ), (AK), (AL), (AM), (AN), (AO), (AP), (AQ), (AR), (AS), (AT), (AU), (AV), (AW), (AX), (AY), (AZ), (BA), (BB), (BC), (BD), (BE), (BF), (BG), (BH), (BI), (BJ), (BK), (BL), (BM), and (BN) to the subject. (BQ) Method (BO) wherein the subject is seropositive for HSV-2 and seropositive for HSV-1. (BR) Method (BO) wherein the subject is seropositive for HSV-2 and seronegative for HSV-1.

In one embodiment there is provided a composition comprising an envelope glycoprotein of HSV-2 or an immunological fragment thereof; two structural proteins of HSV-2 other than an envelope glycoprotein of HSV-2, or an immunological fragment thereof; an agent that activates innate immunity; and a pharmaceutically acceptable carrier. Exemplary is a composition that comprises gD2, UL25, and SEQ ID NO. 12 (a fragment of UL19) and a monophosphoryl lipid A (MALA) adjuvant, e.g., GLA. In addition to gD2-specific antibody responses, vaccination with this composition may elicit robust HSV-2 antigen-specific CD4 and CD8 effector and memory T cells that respond to subsequent infection with live virus. Notably, prophylactic immunization with this composition may largely or completely protect against lethal intravaginal HSV-2 infection in C57BL/6 mice, with sterilizing immunity in both the genital mucosa and dorsal root ganglia. This composition may expand both CD4 and CD8 T cells induced by previous infection with an attenuated strain of HSV-2. Consistent with this, when applied as a therapy for recurrent HSV-2 lesions in guinea pigs, this composition may reduce the frequency of recurrent lesions.

Kits are also provided. In some kits, there is a vial comprising the pharmaceutical composition comprising an antigenic portion of an HSV-2 envelope glycoprotein and a pharmaceutically acceptable carrier.

These and other aspects and embodiments of the present invention will become evident upon reference to the following detailed description and attached drawings.

DETAILED DESCRIPTION

Figure 1A:
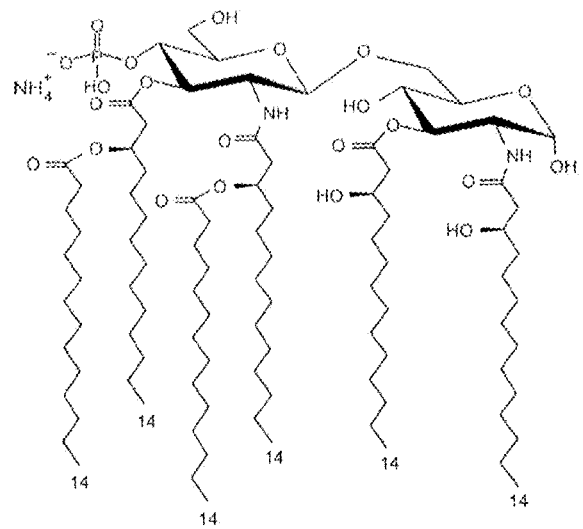
FIGS. 1A-B present a drawing of GLA (the adjuvant used in the Examples) and a schematic of an exemplary oil droplet with surfactants phosphatidycholine and Pluronic F68.

The present disclosure provides immunogenic, pharmaceutical compositions and methods for treatment of or for prevention of herpes simplex virus infections, including HSV-1 and HSV-2 infections. The compositions comprise immunogenic HSV-2 viral proteins or immunogenic portions of the viral proteins, such as fragments or peptides, and at least one agent that activates the innate immune system, preferably a TLR4 agonist, for example, a MALA adjuvant as described herein. The viral proteins (and fragments and peptides) comprise at least one envelope glycoprotein and at least one, two, three or four structural proteins other than an envelope glycoprotein. Alternatively, the viral proteins (and fragments and peptides) comprise at least one antigenic epitope and may comprise part of or all of a leader peptide of an envelope protein. Immunogenic fragments may be used. Some specific agents useful in the compositions include adjuvants, substances that enhance the immune response to an antigen. The proteins and fragments are typically produced by a recombinant technology in which the protein(s) or fragment(s) are expressed in cultured cells. Peptides can also be chemically synthesized.

A. HSV-2 Protein as a Component of a Vaccine

HSV-2 (herpes simplex virus type 2) is an enveloped virus. Its genome expresses over 75 different proteins. Many of the proteins are structural and are used to form the capsid and tegument, while some others are part of the envelope. Major capsid proteins include those expressed from open reading frames (protein names are in parentheses if the common name differs from the ORF name) UL6, UL18 (VP23), UL19 (VP5), UL35 (VP26) and UL38; major tegument proteins include UL7, UL11, UL13, UL14, UL16, UL17, UL21, UL25, UL36, UL37, UL41, UL46 (VP11/12), UL47 (VP13/14), UL48 (VP16), UL49, UL51, and US11; major envelope proteins include UL1 (glycoprotein L (gL)), UL10 (gM), UL20, UL22 (gH), UL27 (gB), UL43, UL44 (gC), UL49A (gN), UL53 (gK), US4 (gG), US5, (gJ), US6 (gD), US7 (gI), and US8 (gE). (Other protein names may have been used in the literature.) An exemplary HSV-2 genome sequence is found in GenBank Accession No. NC 001798.1 (update date 23 Apr. 2010, 2:16 pm, accessed 10 Jan. 2011; incorporated in its entirety). It is understood that the commonly used protein names may be different from the gene names, e.g. UL19 encodes VP5, but reference to the gene name herein is the same as a reference to the encoded protein. It is also understood that the exact sequence of a protein may vary from one herpesvirus to another, and thus all references to an HSV-2 protein (structural or envelope or non-envelope) encompass any such protein obtainable from any naturally occurring HSV-2. A number of sequences are already known and deposited in databases. Nucleic acid encoding an HSV-2 protein with an alternative sequence can be readily isolated or amplified from one or more HSV-2 (e.g. a deposited HSV-2 or a clinical isolate) with appropriate oligonucleotide probes or primers (e.g. that specifically hybridize to a reference sequence under stringent conditions). Within such a group of nucleic acids that encode an HSV-2 protein, e.g. an UL protein, one nucleic acid of the group will hybridize to the complement of another nucleic acid within the group, under stringent conditions.

The term "stringent conditions" refers to conditions under which a probe will hybridize preferentially to its target subsequence, and to a lesser extent to, or not at all to, other sequences. "Stringent hybridization" and "stringent hybridization wash conditions" in the context of nucleic acid hybridization experiments such as Southern and Northern hybridizations are sequence-dependent, and are different under different environmental parameters. An extensive guide to the hybridization of nucleic acids is found in Tijssen, Laboratory Techniques in Biochemistry and Molecular Biology—Hybridization with Nucleic Acid Probes, Part I, Chapter 2 in "Overview of principles of hybridization and the strategy of nucleic acid probe assays", Elsevier (New York, 1993). In certain embodiments, highly stringent hybridization and wash conditions are about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. In certain embodiments, very stringent conditions are equal to the $T_m$ for a particular probe.

An example of stringent hybridization conditions for hybridization of complementary nucleic acids that have more than 100 complementary residues on a filter in a Southern or Northern blot is 50% formalin with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see Sambrook et al. for a description of SSC buffer). A high stringency wash can be preceded by a low stringency wash to remove background probe signal. An example of medium stringency wash for a duplex of, e.g., more than 100 nucleotides, is 1×SSC at 45° C. for 15 minutes. An example of low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

Because one or more envelope proteins is involved in viral entry into host cells, antibodies to envelope proteins can neutralize the virus, that is prevent infection or re-infection by the virus. Without wishing to be held to a mechanistic theory, eliciting antibodies to one or more of those envelope proteins necessary for cellular entry is one way to obtain neutralizing antibodies. Vaccines comprising whole virus, typically inactivated virus, naturally present envelope proteins to immune cells. For a vaccine comprising individual viral proteins, one strategy to obtaining a neutralizing antibody response is to include one or more envelope proteins or immunogenic protein fragments or immunogenic peptides or some combination of these in a vaccine.

HSV-2 encodes 14 or more envelope-associated proteins, at least some of which are involved with cellular entry, including but not limited to gB, gD, gH, and gL. gD appears to bind specifically to an HSV-2 receptor on cells, and gB, along with the heterodimer gH/gL, appears to mediate membrane fusion. Thus, these four envelope glycoproteins are excellent choices as immunogens for inclusion in a vaccine because antibodies elicited to these envelope glycoproteins may include neutralizing antibodies. Alternatively, or in addition, envelope glycoproteins involved in virus shedding are also candidates as immunogens for inclusion in a vaccine.

Most of the structural proteins of HSV-2 other than envelope proteins are found in the capsid and the tegument. The tegument occupies the space between the capsid and the envelope. There are approximately 20 viral proteins found in the tegument. Tegument proteins are important for a variety of viral functions, including immune modulation, viral assembly and final egress. Capsid proteins form a structure that surrounds the nucleic acid genome of the virion. VP5, the product of UL19 is the major capsid protein. A cellular response is often elicited to structural proteins and to a variety of HSV proteins (Hosken et al., J Virol 80:5509-55515, 2006). Generally, the cellular response involves both CD4 and CD8 T cells, cell types that play a role in combating HSV infections.

The immunogenic, pharmaceutical composition (e.g., a vaccine) disclosed herein comprises as immunogens two or more structural proteins, one of which is an envelope glycoprotein and another of which is other than an envelope glycoprotein. Although any of the structural proteins can be used, the choice may be guided by ease of production, ability to formulate into a pharmaceutical composition, information on protein structure, and high expression levels. Because T cell responses are typically MHC-restricted, a vaccine generally contains proteins or peptides that are responded to by the highest number of MHC types, and it may also contain multiple proteins or peptides in order to increase number of individuals that will respond.

Immunogenic pharmaceutical compositions are preferably sterile, free or substantially free of other viral contaminants, and free or substantially free of pyrogenic substances such as LPS. Such compositions are for use as vaccines.

The envelope and non-envelope structural proteins for use in a vaccine as immunogens are typically full-length, but can also be a precursor protein, fragment, or part of a fusion protein. A full-length protein refers to a mature protein; for example, in the case of an envelope protein, a mature protein is the form found in the envelope (e.g., lacking a leader peptide). A precursor protein (pre-protein) is the nascent, translated protein before any processing occurs or a partially-processed protein. As part of a fusion protein, the HSV-2 protein may be present as a precursor or full-length protein or a protein fragment. A fragment of a protein should be immunogenic, containing one or more epitopes that elicit an immune response.

In some embodiments, the immunogenic, pharmaceutical composition (e.g., a vaccine) disclosed herein comprises as immunogens (i) an α group gene product of HSV-2, or an immunological fragment thereof; and/or (ii) a β1 group gene product of HSV-2, or an immunological fragment thereof; and/or (iii) a β2 group gene product of HSV-2, or an immunological fragment thereof; and/or (iv) a γ1 group gene product of HSV-2, or an immunological fragment thereof; and/or (v) a γ2 group gene product of HSV-2, or an immunological fragment thereof. The α, β1, β2, γ1, and γ2 genes are well-known in the art. See, for example, *Herpesviruses and Their Replication* in FUNDAMENTAL VIROLOGY, Chapter 29, 1986.

Thus, any use of the term "immunogen" herein refers to the entire group of polypeptides that are: (a) full length antigen, (2) immunogenic fragments of the antigen, (3) immunogenic variants of the full length antigen or immunogenic fragment, (4) chimeric fusions thereof comprising portions of a different polypeptide, and (5) conjugates thereof. In various embodiments, the envelope and non-envelope structural proteins for use in a vaccine include a polypeptide comprising any of an immunogenic fragment thereof or a variant thereof capable of inducing an immune response specific for the protein.

For example, such immunogenic variants retain at least 90% amino acid identity over at least 10 contiguous amino acids of the antigen, or at least 85% amino acid identity over at least 15 contiguous amino acids of the antigen (e.g. an envelope protein or non-envelope structural protein). As another example, such immunogenic fragments comprise at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 48 or 50 contiguous amino acids of the antigen. The immunogenic fragment may comprise any number of contiguous amino acids between the aforementioned such that, for example, an immunogenic fragment is between about 6-10, 10-15, 15-20, 20-30, 30-40, 40-50, 50-60, 60-70, 70-80, 80-90, 90-100, or more contiguous amino acids of an immunogenic polypeptide. Other examples include at least 70%, 75%, 80%, 85%, 90%, 91%, 92%, 93%, 94%, 95%, 96%, 97%. 98%, or 99% identity over at least 50 contiguous amino acids of the antigen, or over at least 100 contiguous amino acids of the antigen. In some embodiments, the variant is a naturally occurring variant.

Short fragments, often called peptides, are chosen to complex with MHC molecules for binding to T cell receptors and are generally up to about 30 amino acids long, or up to about 25 amino acids long, or up to about 20 amino acids long, or up to about 15 amino acids long, up to about 12 amino acids long, up to about 9 amino acids long, up to about 8 amino acids long. In general, shorter peptides bind to or associate with MHC Class 1 molecules and longer peptides bind to or associate with MHC Class II molecules. Suitable peptides can be predicted using any of a number of bioinformatic programs and tested using well-known methods. Short fragments, also called herein "peptides" are typically from 15-100 amino acids long; longer fragments typically are from 100 amino acids up to full-length, although the length ranges for peptides (short fragments) and longer fragments are not rigid.

As disclosed herein, suitable proteins include precursor proteins, mature proteins, fragments, fusion proteins and peptides. In the compositions, the proteins may be present in the same form or as a mixture of these forms. For example, an envelope glycoprotein may be present as a mature protein and a structural protein as a fragment or an envelope glycoprotein may be present as a fragment and a structural protein as a fragment. For cellular production of the glycoprotein, a signal peptide may be part of the precursor protein. Signal peptides include the glycoprotein D native sequence or others known in the art. It may also be desirable to use a protein without a transmembrane or intracellular region or both.

As discussed herein, one or more portions, also called fragments, of an envelope glycoprotein are chosen for containing one or more epitopes that bind to neutralizing antibodies. Portions containing epitopes may be identified by an assay, such as inhibition of neutralizing antibodies on viral infection of cells. Briefly, overlapping portions of an HSV-2 envelope glycoprotein are mixed with neutralizing antibodies (e.g., serum from an infected animal or human), and the mixture added to HSV-2 and a permissive cell line. If a portion has an epitope that binds to the antibodies, the cell line will be infected with HSV-2. If the portion doesn't have an epitope, the cell line will not be infected.

Compositions that comprise at least one immunogenic fragment of an immunogenic HSV-2 polypeptide may be used as immunogens. In some embodiments, the immunogenic fragment is encoded by the recombinant expression vectors described herein. The immunogenic fragment may consist of at least 6, 10, 15, 20, 30, 40, 50, 60, 70, 80, 90, 100, or more contiguous amino acids of an immunogenic polypeptide. The immunogenic fragment may comprise any number of contiguous amino acids between the aforementioned such that, for example, an immunogenic fragment is between about 6-10, 10-15, 15-20, 20-30, 30-40, 40-50, 50-60, 60-70, 70-80, 80-90, 90-100, or more contiguous amino acids of an immunogenic polypeptide. The immunogenic fragments may comprise a sufficient number of contiguous amino acids that form a linear epitope and/or may comprise a sufficient number of contiguous amino acids that permit the fragment to fold in the same (or sufficiently similar) three-dimensional conformation as the full-length polypeptide from which the fragment is derived to present a non-linear epitope or epitopes (also referred to in the art as conformational epitopes). Assays for assessing whether the immunogenic fragment folds into a conformation comparable to the full-length polypeptide include, for example, the ability of the protein to react with mono- or polyclonal antibodies that are specific for native or unfolded epitopes, the retention of other ligand-binding functions, and the sensitivity or resistance of the polypeptide fragment to digestion with proteases (see, e.g., Sambrook et al., Molecular Cloning: A Laboratory Manual, 3d ed., Cold Spring Harbor Laboratory Press, NY (2001)). Accordingly, by way of example, the three-dimensional conformation of a polypeptide fragment is sufficiently similar to the full-length polypeptide when the capability to bind and the level of binding of an antibody that specifically binds to the full-length polypeptide is substantially the same for the fragment as for the full-length polypeptide (i.e., the level of binding has been retained to a statistically, clinically, and/or biologically sufficient degree compared with the immunogenicity of the exemplary or wild-type full-length antigen).

Fragments that are screened in an assay, such as that described above, are generally short. Generally, the length of a candidate fragment is up to about 40 amino acids long, or up to about 25 amino acids long, or up to about 20 amino acids long, or up to about 15 amino acids long, or up to about 12 amino acids long, or up to about 9 amino acids long, or up to about 8 amino acids long. Fragments used for screening are typically overlapping. For example, a set of fragments might comprise 20 amino acid long fragments that overlap by 16 amino acids (i.e., staggered every 4 amino acids). Typically, the overlapping sets start at the N-terminus of an unprocessed glycoprotein, i.e., contains a leader sequence, and ends at the C-terminal amino acid of the extracellular domain.

Fragments that bind to neutralizing antibody are chosen and may be used in a pharmaceutical composition as disclosed herein. The fragments may be used "as-is" or engineered further or in combination with other fragments. For fragments that are big enough and complex enough to be immunogenic, they may be used in pharmaceutical compositions. Fragments less than about 1000 MW are unlikely to be immunogenic, although complexity can also play a role in whether a fragment is immunogenic. For example, homopolymers consisting of repeating units of a single amino acid are poor immunogens regardless of their size, whereas co-polymers of 2 or 3 amino acids may be good immunogens. A co-polymer of glutamic acid and lysine needs to be at least about 30-40,000 MW to be immunogenic. Amino acids with aromatic side chains increase immunogenicity, such that a fragment of only about 4000 MW that comprises tyrosine and phenylalanine may be immunogenic. Fragments that are too short or not complex enough to be immunogenic may be conjugated to a carrier protein, such as KLH (keyhole limpit hemocyanin), ovalbumim, bovine serum albumin, or other protein that is foreign to the subject receiving the pharmaceutical composition, or the fragments may be coupled together to create an immunogenic protein. Whether or not a fragment is immunogenic may be determined in an animal. For example, the fragment may be administered to an animal in a prime-boost regimen, and antibodies to the fragment assayed in an e.g., ELISA using serum drawn 7-10 days following the boost. A detectable signal indicates that the fragment is immunogenic. Higher signals are desirable. Other assays for immunogenicity are well known to one of average skill.

In some embodiments, the fragments used in the compositions are synthetic long peptides. "Synthetic long peptide" (SLP) refers to a protein sequence manufactured ex vivo and having a length as short as about 25 amino acids and as long as about 100 amino acids. An SLP should be long enough to be taken up and processed by dendritic cells for presentation on their cell surface with MHC class I or class II molecules. SLPs are peptides derived from proteins against which an immune response is desired. In one embodiment, the immune response is a T cell response. The proteins may be known antigens or, in the case of some proteins, they may be candidate antigens.

An SLP comprises at least one CD4 epitope or at least one CD8 epitope or at least one CD4 and at least one CD8 epitope. A CD4 epitope refers to an amino acid sequence that binds to class II MHC and a CD8 epitope refers to an amino acid sequence that binds to class I MHC. Epitope sequences are derived from the amino acid sequence of an immunogen; in vivo, briefly, the immunogen is taken up or synthesized by antigen-processing cells (e.g., dendritic cells) and degraded into peptides, which associate with MHC molecules and are presented on the cell surface as an MHC-peptide complex. Peptides complexed with MHC class I molecules interact with the T cell antigen receptor and CD8 on CD8+ T cells, these peptides are called CD8 epitopes; peptides complexed with MHC class II molecules interact with T cell antigen receptor and CD4 on CD4+ T cells, these peptides are called CD4 epitopes. Activated CD8+ T cells become cytotoxic T cells, which recognize and kill target cells displaying the MHC class I-CD8 epitopes. Often, target cells are infected or tumor cells. Activated CD4+ T cells become helper T cells, and depending on their subtype, help B cells to produce antibody or activate natural killer cells, phagocytes and CD8+ T cells. Activation of both CD4+ T cells and CD8+ T cells contribute to a comprehensive cellular immune response.

As disclosed above, an SLP should be long enough to be taken up and processed by dendritic cells and presented on their cell surface with MHC molecules. Peptides complexed with MHC class I molecules are generally 8-11 amino acids in length, and peptides complexed with MHC class II molecules are generally 13-17 amino acids in length, although longer or shorter lengths are not uncommon. As such, an SLP will typically be at least 25 amino acids long and as long as 100 amino acids long (e.g., at least 30 aa, at least 35 aa, at least 40 aa, at least 45 aa, at least 50 aa, at least 55 aa, at least 60 aa, at least 65 aa, at least 70 aa, at least 75 aa, at least 80 aa, at least 85 aa, at least 90 aa, at least 95 aa). The length of an SLP will generally be about 45 aa or about 50 aa in length.

Epitopes may have known sequence or unknown sequence. A plethora of proteins have been mapped for CD4 and CD8 epitopes. For SLPs comprising one or more of these epitopes, the length will typically be about 45 aa. Moreover, the epitope may be flanked by about 15 aa at the N-terminal and at the C-terminal sides. The flanking sequences are typically the sequences that flank the epitope sequence in the native protein. As discussed above, an SLP may comprise more than one epitope, the multiple epitopes may be all CD4 or CD8 epitopes or a mixture of CD4 and CD8 epitopes. Furthermore, the epitopes may overlap in sequence (see Example 1 for some exemplary SLPs that comprise overlapping epitopes). The total number of SLPs used may be such that all known CD4 and CD8 epitopes are represented.

SLPs may be synthesized by any of a variety of methods (see Corradin et al., Sci Translational Med 2:1, 2010 for a general discussion of synthesis methods). Automated peptide synthesizers are commercially available, and many companies provide synthesis services (e.g., Abbiotec, American Peptide Company, AnaSpec, Bachem, Covance Research Products, Invitrogen). Following synthesis, peptides are purified, typically by HPLC, although alternative purification methods such as ion exchange chromatography and gel filtration chromatography may be used. Acceptable purity is at least 90% or at least 95% or at least 98% as assessed by analytical HPLC.

When a protein has not been mapped for CD4 epitopes or CD8 epitopes or both, a set of SLPs that comprise the entire protein sequence may be synthesized. Each SLP will typically be about 50 aa, and consecutive SLPs may overlap in sequence by about 25 aa. Alternatively, or in addition, algorithms and computer programs can be used to predict sequences that will bind to MHC class I and class II molecules. Such programs are readily available, e.g., RANKPEP (Reche et al., Human Immunol 63: 701, 2002), Epipredict (Jung et al., Biologicals 29: 179, 2001) and MHCPred (Guan et al. Nucl Acids Res 31: 3621, 2003 and Guan et al., Appl Bioinformatics 5: 55, 2006), EpiMatrix (EpiVax, Inc.).

The sequence of an SLP may be adjusted as necessary for optimum production. For example, one or more amino acids at the ends of a peptide derived from a native sequence may be omitted in order to improve solubility or stability, or to increase or decrease the overall charge. As a specific example, a peptide sequence with a high content of hydrophobic amino acids may be difficult to solubilize. As a guide, hydrophobic content is ideally less than 50%. Peptides containing cysteine, methionine, or tryptophan residues, especially multiple Cys, Met, or Trp residues, may be difficult to synthesize. Substitution of another amino acid, either a standard or a non standard amino acid, such as hydroxyproline, gamma-aminobutyric acid, norleucine, may improve synthesis efficiency or purity. Other considerations in designing an SLP include the extent of β-sheet formation, N-terminal amino acid (e.g., an N-terminal Gln can cyclize), minimizing adjacent Ser and Pro residues.

Some structural proteins that are especially useful for inclusion in a pharmaceutical composition include UL19 (SEQ ID No. 4), UL19 Upper Domain Fragment, UL 25 (SEQ ID No. 5) and UL47 (SEQ ID No. 6). Structure of viral proteins may be found in MMDB (Molecular Modeling Database) of NCBI. Molecular structure information is available for UL25 (MMDB ID: 37706, Bowman et al. J. Virol. 80:2309, 2006, incorporated in its entirety), VP5 (product of UL19) (MMDB ID: 26005, Bowman et al., EMBO J. 22: 757-765, 2003, incorporated in its entirety), VP13/14 (product of UL47) (MMDB ID: 6022), and envelope protein gD2 (MMDB ID: 36244, Krummenacher et al. EMBO J. 24:4144-4153, 2005, incorporated in its entirety), ICP34.5, as well as many other HSV-2 proteins. In addition, some T-cell epitopes of viral proteins are known (Koelle et al., J Virol 74:10930-10938, 2000; Muller et al., J Gen Virol 90:1153-1163, 2009; Koelle et all, J Immunol 166:4049-4058, 2001; BenMohamed et al., J Virol 77:9463-9473, 2003; U.S. Pat. No. 6,855,317; P.C.T. Pub. No. WO 2004/009021, all of which references are incorporated in their entirety).

Immunogenic fragments, variants and fusion proteins of any of these are proteins, especially UL19, UL19 Upper Domain Fragment, UL25 and UL47, are specifically contemplated for use in the immunogenic compositions herein. Thus, the disclosure includes fragments or variants of any one of SEQ ID NO: 4, 5, 6, or 12 that retain at least 90% amino acid identity over at least 10 contiguous amino acids thereof, or at least 85% amino acid identity over at least 15 contiguous amino acids thereof. As another example, the disclosure includes immunogenic fragments comprising at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 48 or 50 contiguous amino acids of the sequence, or between about 6-10, 10-15, 15-20, 20-30, 30-40, 40-50, 50-60, 60-70, 70-80, 80-90, 90-100, or more contiguous amino acids of the sequence. The disclosure also includes variants having at least 70%, 75%, 80%, 85%, 90%, 91%, 92%, 93%, 94%, 95%, 96%, 97%. 98%, or 99% identity over at least 50 contiguous amino acids of the sequence, or over at least 100 contiguous amino acids of the sequence. In some embodiments, the variant is a naturally occurring variant, preferably one that hybridizes under stringent conditions to a polynucleotide encoding any one of SEQ ID NO: 4, 5, 6 or 12.

As disclosed herein, immunogenic fragments, including peptides, of a non-envelope structural protein (e.g., UL19 (SEQ ID Nos. 9 and 10) and UL25 (SEQ ID No. 11)) and of an envelope protein (e.g., gD2 (SEQ ID Nos. 7 and 8) may be used or may be part of a longer sequence (i.e., fragment) derived from the protein. Peptides, as used herein, refer to short sequences of amino acids, generally from at least 15 residues and generally up to about 100 residues, or from about 20 residues to about 80 residues, or from about 30 residues to about 70 residues. Fragments, as used herein, refer to any length of polypeptide less than full-length protein and are generally at least 100 amino acids long, although the size range of fragments can overlap the size range of peptides (e.g., fragments from about 50 residues long). In particular, a UL19 Upper Domain Fragment is missing at least 75%, 80%, 85%, 90%, 95% or all of residues 1-450 and residues 1055-1374 of UL19. As such, the Upper Domain Fragment may begin, for example, at any one of residues 337-451, and end at any one of residues 1055-1294 (and is lacking at least amino acids 1-336 and 1295-1374 of SEQ ID NO: 4). For example, a UL19 fragment may be from about residue 451 to about 1054 (SEQ ID NO:12). A UL19 Upper Domain Fragment may comprise about 50, 100, 150, 200, 250, 300, 350, 400, 450, or 500 amino acids or more of SEQ ID NO: 12.

In addition, the peptides and fragments herein may be fused to heterologous peptides. Examples of heterologous peptides include sequences from other proteins (e.g., in the case of UL19, a UL19 Upper Domain Fragment may be fused to a sequence from another protein that is not UL19), or tag sequences, such as hexa-histidine, which generally will be located at either the N-terminus or the C-terminus. Thus, the immunogenic fragments or variants described herein may be fused to another peptide that enhances immunogenicity, another peptide that serves as a tag or marker, or another peptide from another HSV-2 structural protein. As such, an immunogenic polypeptide may comprise a fragment consisting of a designated fragment of an HSV-2 structural protein. In one example, an immunogenic polypeptide comprises a fragment of UL19 consisting of SEQ ID NO: 12 or a fragment of SEQ ID NO: 12, optionally fused to a non-UL19 peptide. In another example, an immunogenic polypeptide comprises a peptide consisting of an amino acid sequence that is at least 80% or 90% identical over 50 contiguous amino acids of SEQ ID NO: 12, optionally fused to a non-UL19 peptide.

Surprisingly, the examples herein show that a UL19 Upper Domain Fragment has the ability to elicit protective antibodies to HSV-2 infection, such that the remainder of the UL19 protein is not needed as an immunogen.

Typically the proteins in a pharmaceutical composition will be other than a precursor protein because expression in a eukaryotic cell will typically result in a mature protein, lacking the leader sequence (also known as a signal peptide). The leader sequence of gD encompasses approximately residues 1-25. The leader sequence of gB encompasses approximately residues 1-22. Glycoprotein D (SEQ ID No. 2) is 393 amino acid protein and has an extracellular region spanning approximately residues 26-340, a transmembrane region spanning approximately residues 341-361 and a cytoplasmic region spanning approximately residues 362-393, and a number of N-linked glycosylation sites at residues 119, 146, 287 (UniProtKB/Swiss-Prot accession number Q69467, version 49 of entry and version 1 of sequence). An exemplary gD fragment (herein alternatively referred to as gD2) comprises the sequence shown in SEQ ID No. 3.

In some embodiments, antigenic and immunogenic fragments from envelope glycoproteins may comprise part or all of a leader sequence, which is sometimes called a signal peptide. The leader sequence is usually approximately 15-20 amino acids, and in normal cellular processes, it may be cleaved off by cellular apparatus, however, some of the glycoprotein in intact virions may have the leader sequence. Leader sequences usually have some polar amino acids at the N-terminus and the internal amino acids are generally hydrophobic. As discussed above, the leader sequences for some of the HSV-2 envelope glycoproteins have been determined. For other HSV-2 envelope glycoproteins, computer programs may be used to predict the signal peptide. Some of these programs include SIG-Pred (bmbpcu36.leeds.ac.uk/prot_analysis/Signal.html), PrediSi (www.predisi.de), OCTOPUS (octopus.cbr.su.se), and sigcleave (emboss-.sourceforge.net/apps/cvs/emboss/apps/sigcleave.html).

A variety of techniques may be used to inhibit cleavage of the signal peptide during cellular production of an antigenic or immunogenic fragment containing the leader sequence for use in the compositions described herein. For example, one or more of the amino acids flanking the cleavage site may be altered to a different amino acid, resulting in a sequence that is not recognized or cleaved by cellular apparatus. For this method, alterations are designed based on cleavage sites known in the art: glycine is not preferentially used in any of the positions, tyrosine, is rarely found in the first few positions after cleavage sites, whereas proline is often found in many cleavage sites except at the +1 position and glutamine is commonly found at the +1 residue (Zhang and Henzel, Protein Sci. 13: 219, 2004). The proposed sequence may be evaluated with a prediction program to determine if cleavage is likely to be inhibited. If cleavage is likely, then additional alterations are made and the newly proposed sequence re-evaluated. Other techniques to inhibit cleavage of a signal peptide include addition of one or more amino acids at the recognition and cleavage sequence, N-terminal addition of a signal peptide and recognition sequence such that the added signal peptide is preferentially cleaved, and production in a host cell that lacks the machinery to cleave the signal peptide.

In certain embodiments, a fragment comprises an HSV-2 glycoprotein, including the leader sequence. In other embodiments, a fragment comprises a portion of a HSV-2 glycoprotein including from the leader sequence to the start of the transmembrane domain. In yet other embodiments, a fragment comprises a portion of an HSV-2 glycoprotein including from the leader sequence and ending within the extracellular domain. In other embodiments, a fragment comprises non-contiguous portions of an HSV-2 glycoprotein, in which one of the portions comprises an antigenic epitope in the leader sequence. In yet other embodiments, a fragment comprises non-contiguous portions of an HSV-2 glycoprotein, in which the portions comprise an epitope or it comprises portions from different HSV-2 glycoproteins, in which the portions comprise an epitope.

Glycoprotein B (SEQ ID No. 1) has an extracellular region spanning approximately residues 23-771, a transmembrane region spanning approximately residues 772-792 and a cytoplasmic region spanning approximately residues 793-904, and a number of N-linked glycosylation sites at residues 82, 136, 393, 425, 486, 671 (UniProtKB/Swiss-Prot accession number P08666, version 60 of entry and version 2 of sequence). Glycoprotein K is a 338 amino acid protein with a 30 amino acid leader sequence at its N-terminal end (Ramaswarmy and Holland, Virology 186:579-587, 1992). Glycoprotein C has a predicted 27 amino acid leader sequence, glycoprotein E has a predicted 23 amino acid leader sequence, and glycoprotein L has a predicted 16 amino acid leader sequence (Signal Peptide Resource, proline.bic.nus.edu.sg, accessed 6 Oct. 2011).

Proteins or protein fragments are preferably immunogenic. An "immunogen" is capable of inducing an immune response. Immunogenic peptide sequences are generally recognized by T cells (e.g., CD4 or CD8 T cells) in at least some seropositive subjects. Peptide sequences can be identified by screening peptides derived from the complete sequence, generally using a series of overlapping peptides. A variety of assays can be used to determine if T cells recognize and respond to a peptide. For example, a chromium-release cytotoxicity assay (Kim et al., J Immunol 181:6604-6615, 2008, incorporated for its assay protocol), ELISPOT assay, an intracellular cytokine staining assay and MHC multimer staining (Novak et al. J Clin Invest 104: R63-R67, 1999; Altman et al., Science 274:94-96, 1996) are among suitable assays. In some cases, the fragment(s) comprise immunodominant peptide sequences. Some immunodominant epitopes have been identified for HSV-2 glycoproteins and structural proteins (e.g., Kim et al. J Immunol 181:6604-6615, 2008; Chentoufi et al., J. Virol. 82:11792-11802, 2008; Koelle et al., Proc Natl Acad Sci USA 100: 12899-12904, 2003; all references are hereby incorporated in their entirety). Immunogenic peptides can also be predicted by bioinformatic software (Flower, Methods in Molecular Biology vol. 409, 2007). Some exemplary programs and databases include FRED (Feldhahn et al. Bioinformatics 15:2758-9, 2009), SVMHC (Donnes and Kohlbacher, Nucleic Acids Res 34:W1940197, 2006), AntigenDB (Ansari et al., Nucleic Acids Res 38:D847-853, 2010), TEPITOPE (Bian and Hammer Methods 34:468-475, 2004), Any of the HSV-2 proteins, including precursor proteins, mature proteins and fragments, including peptides, can be incorporated as part of a fusion protein. The fusion partner or partners can be any of the HSV-2 proteins or a non-HSV-2 protein sequence. Some common reasons to use fusion proteins are to improve expression or aid in purification of the resulting protein. For example, a signal peptide sequence tailored for the host cell of an expression system can be linked to an HSV-2 protein or a tag sequence for use in protein purification can be linked, and subsequently cleaved if a cleavage sequence is also incorporated. Multiple peptide epitopes from one or more of the proteins can be fused or fragments from one or more of the proteins can be fused. For example, structural proteins or fragments of structural proteins can be linked, such as a fusion protein of VP13/14 (UL47) and major capsid protein (UL19) or UL25 and UL47 or UL25 and UL19. The segments of a fusion protein can be in any order, that is for a fusion of UL19 and UL47, either protein can be at the N-terminus. Similarly, multiple peptide epitopes can be in any order.

Manufacture of HSV-2 proteins, including precursor proteins, fragments, and fusion proteins is generally achieved by expression in cultured cells or by chemical synthesis. ("HSV-2 proteins" is used herein to include all these forms.) Short fragments are commonly synthesized chemically, either using a machine (many are commercially available) or manually. If produced by cells, a variety of suitable expression systems, both prokaryotic and eukaryotic systems, are well known and may be used. Host cells often used and suitable for production of proteins include *E. coli*, yeast, insect, and mammalian. Expression vectors and host cells are commercially available (e.g., Invitrogen Corp., Carlsbad, Calif., USA) or may be constructed. An exemplary vector comprises a promoter and cloning site for the sequence encoding a protein of interest such that the promoter and sequence are operatively linked. Other elements may be present, such as a secretion signal sequence (sometimes called a leader sequence), a tag sequence (e.g., hexa-His), transcription termination signal, an origin of replication, especially if the vector is replicated extra-chromosomally, and a sequence encoding a selectable product. Methods and procedures to transfect host cells are also well known.

Expressed proteins are collected and may be used "as-is" or more typically, analyzed and further purified. Typical procedures for determining purity or quantity include gel electrophoresis, Western blotting, mass spectrometry, and ELISA. Activity of proteins is generally assessed in a biological assay, such as those described in the Examples. If necessary or desired, proteins may be further purified. Many purification methods are well known and include size chromatography, anion or cation exchange chromatography, affinity chromatography, precipitation, and immune precipitation. Intended use of the protein will typically determine the extent of purification, with use in humans requiring likely the highest level of purity.

B. Agents that Activate Innate Immunity

The innate immune system comprises cells that provide defense in a non-specific manner to infection by other organisms. Innate immunity is an immediate defense but it is not long-lasting or protective against future challenges. Immune system cells that generally have a role in innate immunity are phagocytic, such as macrophages and dendritic cells. The innate immune system interacts with the adaptive (also called acquired) immune system in a variety of ways. Cells of the innate immune system can participate in antigen presentation to cells of the adaptive immune system, including expressing lymphokines that activate other cells, emitting chemotactic molecules that attract cells that may be specific to the invader, and secreting cytokines that recruit and activate cells of the adaptive immune system. The immunogenic pharmaceutical compositions disclosed herein include an agent that activates innate immunity in order to enhance the effectiveness of the composition.

Many types of agents can activate innate immunity. Organisms, like bacteria and viruses, can activate innate immunity, as can components of organisms, chemicals such as 2'-5' oligo A, bacterial endotoxins, RNA duplexes, single stranded RNA and other molecules. Many of the agents act through a family of molecules—the Toll-like receptors (TLRs). Engaging a TLR can also lead to production of cytokines and chemokines and activation and maturation of dendritic cells, components involved in development of acquired immunity. The TLR family can respond to a variety of agents, including lipoprotein, peptidoglycan, flagellin, imidazoquinolines, CpG DNA, lipopolysaccharide and double stranded RNA (Akira et al. Biochemical Soc Transactions 31: 637-642, 2003). These types of agents are sometimes called pathogen (or microbe)-associated molecular patterns.

In one aspect, one or more adjuvants are included in the composition, in order to provide an agent(s) that activates innate immunity. An adjuvant is a substance incorporated into or administered simultaneously with antigen that increases the immune response. A variety of mechanisms have been proposed to explain how different adjuvants work (e.g., antigen depots, activators of dendritic cells, macrophages). Without wishing to be bound by theory, one mechanism involves activating the innate immune system, resulting in the production of chemokines and cytokines, which in turn activate the adaptive (acquired) immune response. In particular, some adjuvants activate dendritic cells through TLRs. Thus, an adjuvant is one type of agent that activates the innate immune system that may be used in a vaccine to HSV-2. An adjuvant may act to enhance an acquired immune response in other ways too. Preferably the adjuvant is a TLR4 agonist.

One adjuvant that may be used in the compositions described herein is a monoacid lipid A (MALA) type molecule. An exemplary MALA is MPL® adjuvant as described in, e.g., Ulrich J. T. and Myers, K. R., "Monophosphoryl Lipid A as an Adjuvant" Chapter 21 in Vaccine Design, the Subunit and Adjuvant Approach, Powell, M. F. and Newman, M. J., eds. Plenum Press, NY 1995. Another exemplary MALA is described by the chemical formula (I):

(I)

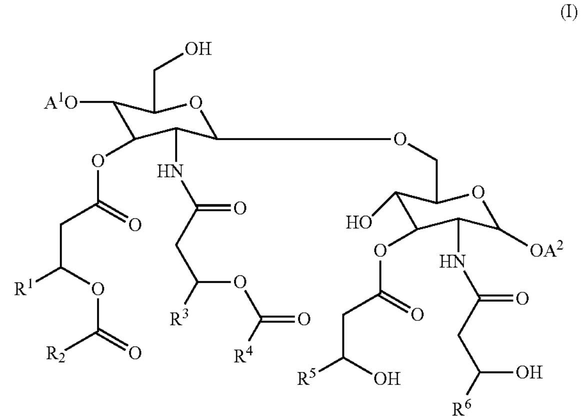

wherein the moieties $A^1$ and $A^2$ are independently selected from the group of hydrogen, phosphate, phosphate salts, carboxylate, carboxylate salts, sulfate, sulfate salts, sulfite, sulfite salts, aspartate, aspartate salts, succinate, succinate salts, carboxymethylphosphate and carboxymethylphosphate salts. Sodium and potassium are exemplary counterions for the phosphate and carboxylate salts. At least one of $A^1$ and $A^2$ is hydrogen. The moieties $R^1$, $R^2$, $R^3$, $R^4$, $R^5$, and $R^6$ are independently selected from the group of hydrocarbyl having 3 to 23 carbons, preferably a straight chain alkyl, represented by $C_3$-$C_{23}$. For added clarity it will be explained that when a moiety is "independently selected from" a specified group having multiple members, it should be understood that the member chosen for the first moiety does not in any way impact or limit the choice of the member selected for the second moiety. The carbon atoms to which $R^1$, $R^3$, $R^5$ and $R^6$ are joined are asymmetric, and thus may exist in either the R or S stereochemistry. In one embodiment all of those carbon atoms are in the R stereochemistry, while in another embodiment all of those carbon atoms are in the S stereochemistry.

"Hydrocarbyl" or "alkyl" refers to a chemical moiety formed entirely from hydrogen and carbon, where the arrangement of the carbon atoms may be straight chain or branched, noncyclic or cyclic, and the bonding between adjacent carbon atoms maybe entirely single bonds, i.e., to provide a saturated hydrocarbyl, or there may be double or triple bonds present between any two adjacent carbon atoms, i.e., to provide an unsaturated hydrocarbyl, and the number of carbon atoms in the hydrocarbyl group is between 3 and 24 carbon atoms. The hydrocarbyl may be an alkyl, where representative straight chain alkyls include methyl, ethyl, n-propyl, n-butyl, n-pentyl, n-hexyl, and the like, including undecyl, dodecyl, tridecyl, tetradecyl, pentadecyl, hexadecyl, heptadecyl, octadecyl, etc.; while branched alkyls include isopropyl, sec-butyl, isobutyl, tert-butyl, isopentyl, and the like. Representative saturated cyclic hydrocarbyls include cyclopropyl, cyclobutyl, cyclopentyl, cyclohexyl, and the like; while unsaturated cyclic hydrocarbyls include cyclopentenyl and cyclohexenyl, and the like. Unsaturated hydrocarbyls contain at least one double or triple bond between adjacent carbon atoms (referred to as an "alkenyl" or "alkynyl", respectively, if the hydrocarbyl is non-cyclic, and cycloalkeny and cycloalkynyl, respectively, if the hydrocarbyl is at least partially cyclic). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like. For example, "C6-11 alkyl" mean an alkyl as defined above, containing from 6-11 carbon atoms, respectively.

The adjuvant of formula (I) may be obtained by synthetic methods known in the art, for example, the synthetic methodology disclosed in PCT International Publication No. WO 2009/035528, which is incorporated herein by reference, as well as the publications identified in WO 2009/035528, where each of those publications is also incorporated herein by reference. Certain of the adjuvants may also be obtained commercially. A preferred adjuvant is Product No. 699800 as identified in the catalog of Avanti Polar Lipids, Alabaster Ala., wherein R1, R3, R5 and R6 are undecyl and R2 and R4 are dodecyl.

Figure 1B:
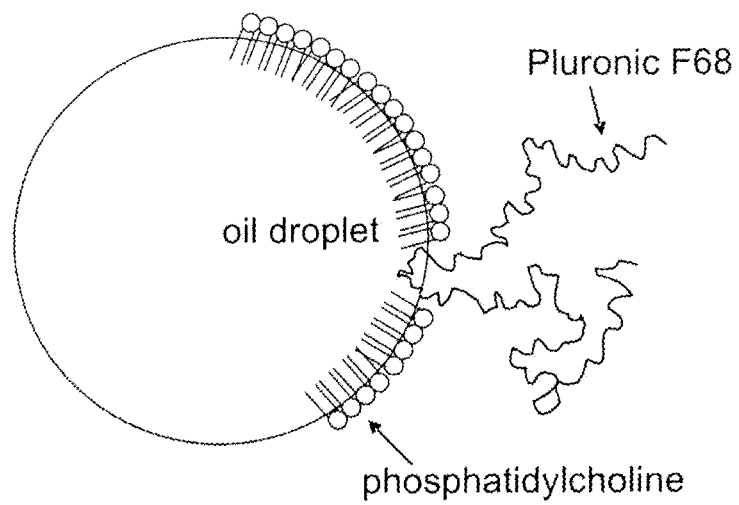

In various embodiments of the invention, the adjuvant has the chemical structure of formula (I) but the moieties A1, A2, R1, R2, R3, R4, R5, and R6 are selected from A1 being phosphate or phosphate salt and A2 is hydrogen; and R1, R3, R5 and R6 are selected from C7-C15 alkyl; and R2 and R4 are selected from C9-C17 hydrocarbyl. In a preferred embodiment of the invention, the GLA used in the examples herein has the structural formula set forth in FIG. 1, wherein R1, R3, R5 and R6 are undecyl and R2 and R4 are tridecyl.

The MALA adjuvants described above are a preferred adjuvant class for use in the immunogenic pharmaceutical compositions described herein. However, any of the following adjuvants may also be used alone, or in combination with an MALA adjuvant, in formulating an immunogenic pharmaceutical composition.

The adjuvant may be alum, where this term refers to aluminum salts, such as aluminum phosphate (AlPO4) and aluminum hydroxide (Al(OH)3). When alum is used as the adjuvant or as a co-adjuvant, the alum may be present, in a dose of immunogenic pharmaceutical composition in an amount of about 100 to 1,000 µg, or 200 to 800 µg, or 300 to 700 µg or 400 to 600 µg. If the adjuvant of formula (1) is co-formulated with alum, the adjuvant of formula (1) is typically present in an amount less than the amount of alum, in various aspects the adjuvant of formula (1), on a weight basis, is present at 0.1-1%, or 1-5%, or 1-10%, or 1-100% relative to the weight of alum. In one aspect of the invention, the composition excludes the presence of alum.

The adjuvant may be an emulsion having vaccine adjuvant properties. Such emulsions include oil-in-water emulsions. Freund's incomplete adjuvant (IFA) is one such adjuvant Another suitable oil-in-water emulsion is MF-59™ adjuvant which contains squalene, polyoxyethylene sorbitan monooleate (also known as Tween™ 80 surfactant) and sorbitan trioleate. Squalene is a natural organic compound originally obtained from shark liver oil, although also available from plant sources (primarily vegetable oils), including amaranth seed, rice bran, wheat germ, and olives. Other suitable emulsion adjuvants are Montanide™ adjuvants (Seppic Inc., Fairfield N.J.) including Montanide™ ISA 50V which is a mineral oil-based adjuvant, Montanide™ ISA 206, and Montanide™ IMS 1312. While mineral oil may be present in the adjuvant, in one embodiment, the oil component(s) of the compositions of the present invention are all metabolizable oils.

The adjuvant may be AS02™ adjuvant or AS04™ adjuvant. AS02™ adjuvant is an oil-in-water emulsion that contains both MPL™ adjuvant and QS-21™ adjuvant (a saponin adjuvant discussed elsewhere herein). AS04™ adjuvant contains MPL™ adjuvant and alum. The adjuvant may be Matrix-M™ adjuvant.

The adjuvant may be a saponin such as those derived from the bark of the *Quillaja saponaria* tree species, or a modified saponin, see, e.g., U.S. Pat. Nos. 5,057,540; 5,273,965; 5,352,449; 5,443,829; and 5,560,398. The product QS-21™ adjuvant sold by Antigenics, Inc. Lexington, Mass. is an exemplary saponin-containing co-adjuvant that may be used with the adjuvant of formula (1). Related to the saponins is the ISCOM™ family of adjuvants, originally developed by Iscotec (Sweden) and typically formed from saponins derived from *Quillaja saponaria* or synthetic analogs, cholesterol, and phospholipid, all formed into a honeycomb-like structure.

The adjuvant may be a cytokine that functions as an adjuvant, see, e.g., Lin R. et al. Clin. Infec. Dis. 21(6):1439-1449 (1995); Taylor, C. E., Infect. Immun. 63(9):3241-3244 (1995); and Egilmez, N. K., Chap. 14 in Vaccine Adjuvants and Delivery Systems, John Wiley & Sons, Inc. (2007). In various embodiments, the cytokine may be, e.g., granulocyte-macrophage colony-stimulating factor (GM-CSF); see, e.g., Change D. Z. et al. Hematology 9(3):207-215 (2004), Dranoff, G. Immunol. Rev. 188:147-154 (2002), and U.S. Pat. No. 5,679,356; or an interferon, such as a type I interferon, e.g., interferon-α (IFN-α) or interferon-β (IFN- β), or a type II interferon, e.g., interferon-γ (IFN-γ), see, e.g., Boehm, U. et al. Ann. Rev. Immunol. 15:749-795 (1997); and Theofilopoulos, A. N. et al. Ann. Rev. Immunol. 23:307-336 (2005); an interleukin, specifically including interleukin-1α (IL-1α), interleukin-1β (IL-1β), interleukin-2 (IL-2); see, e.g., Nelson, B. H., J. Immunol. 172(7):3983-3988 (2004); interleukin-4 (IL-4), interleukin-7 (IL-7), interleukin-12 (IL-12); see, e.g., Portielje, J. E., et al., Cancer Immunol. Immunother. 52(3): 133-144 (2003) and Trinchieri. G. Nat. Rev. Immunol. 3(2):133-146 (2003); interleukin-15 (I1-15), interleukin-18 (IL-18); fetal liver tyrosine kinase 3 ligand (Flt3L), or tumor necrosis factor α (TNFα).

The adjuvant may be unmethylated CpG dinucleotides, optionally conjugated to the antigens described herein.

Examples of immunopotentiators that may be used in the practice of the methods described herein as co-adjuvants include: MPL™; MDP and derivatives; oligonucleotides; double-stranded RNA; alternative pathogen-associated molecular patterns (PAMPS); saponins; small-molecule immune potentiators (SMIPs); cytokines; and chemokines.

In various embodiments, the co-adjuvant is MPL™ adjuvant, which is commercially available from GlaxoSmithKline (originally developed by Ribi ImmunoChem Research, Inc. Hamilton, Mont.). See, e.g., Ulrich and Myers, Chapter 21 from Vaccine Design: The Subunit and Adjuvant Approach, Powell and Newman, eds. Plenum Press, New York (1995). Related to MPL™ adjuvant, and also suitable as co-adjuvants for use in the compositions and methods described herein, are AS02™ adjuvant and $AS_{04}$™ adjuvant. AS02™ adjuvant is an oil-in-water emulsion that contains both MPL™ adjuvant and QS-21™ adjuvant (a saponin adjuvant discussed elsewhere herein). AS04™ adjuvant contains MPL™ adjuvant and alum. MPL™ adjuvant is prepared from lipopolysaccharide (LPS) of *Salmonella minnesota* R595 by treating LPS with mild acid and base hydrolysis followed by purification of the modified LPS.

When two adjuvants are utilized in combination, the relative amounts of the two adjuvants may be selected to achieve the desired performance properties for the composition which contains the adjuvants, relative to the antigen alone. For example, the adjuvant combination may be selected to enhance the antibody response of the antigen, and/or to enhance the subject's innate immune system response. Activating the innate immune system results in the production of chemokines and cytokines, which in turn may activate an adaptive (acquired) immune response. An important consequence of activating the adaptive immune response is the formation of memory immune cells so that when the host re-encounters the antigen, the immune response occurs quicker and generally with better quality.

The adjuvant(s) may be pre-formulated prior to their combination with the HSV-2 proteins. The adjuvant(s) may be formulated in an oil-in-water emulsion in which the adjuvant is incorporated in the oil phase. For use in humans, the oil is preferably metabolizable. The oil may be any vegetable oil, fish oil, animal oil or synthetic oil; the oil should not be toxic to the recipient and is capable of being transformed by metabolism. Nuts (such as peanut oil), seeds, and grains are common sources of vegetable oils. Particularly suitable metabolizable oils include squalene (2,6,10,15,19,23-hexamethyl-2,6,10,14,18,22-tetracosahexane), an unsaturated oil found in many different oils, and in high quantities in shark-liver oil. Squalene is an intermediate in the biosynthesis of cholesterol. In addition, the oil-in-water emulsions typically comprise an antioxidant, such as alpha-tocopherol (vitamin E, U.S. Pat. No. 5,650,155, U.S. Pat. No. 6,623,739). Stabilizers, such as a triglyceride, ingredients that confer isotonicity, and other ingredients may be added. An exemplary oil-in-water emulsion using squalene is known as "SE" and comprises squalene, glycerol, phosphatidylcholine or lecithin or other block co-polymer as a surfactant in an ammonium phosphate buffer, pH 5.1, with alpha-toceraphol.

The method of producing oil-in-water emulsions is well known to a person skilled in the art. Commonly, the method comprises mixing the oil phase with a surfactant, such as phosphatidylcholine, poloxamer, block co-polymer, or a TWEEN80® solution, followed by homogenization using a homogenizer. For instance, a method that comprises passing the mixture one, two, or more times through a syringe needle is suitable for homogenizing small volumes of liquid. Equally, the emulsification process in a microfluidiser (M110S microfluidics machine, maximum of 50 passes, for a period of 2 min at maximum pressure input of 6 bar (output pressure of about 850 bar)) can be adapted to produce smaller or larger volumes of emulsion. This adaptation can be achieved by routine experimentation comprising the measurement of the resultant emulsion until a preparation was achieved with oil droplets of the desired diameter. Other equipment or parameters to generate an emulsion may also be used. Disclosures of emulsion compositions, and method of their preparation, may be found in, e.g., U.S. Pat. Nos. 5,650,155; 5,667,784; 5,718,904; 5,961,970; 5,976,538; 6,572,861; and 6,630,161.

C. Pharmaceutical Compositions and Uses

1. Formulation

A claimed pharmaceutical composition comprises an HSV-2 glycoprotein or an immunogenic fragment thereof, an HSV-2 structural protein other than an envelope glycoprotein or an immunogenic fragment thereof, an agent that is an agonist for the innate immune system, and a pharmaceutically acceptable carrier. The composition may comprise more than one glycoprotein (or fragment), more than one structural protein (or fragment) or more than one agent.

In some aspects, the pharmaceutical composition comprises an antigenic portion of an HSV glycoprotein, a pharmaceutically acceptable carrier, and optionally an agent that is an agonist for the innate immune system. The composition may comprise more than one glycoprotein portion and one or more than one agent. The carrier may optionally have adjuvant properties, e.g., some emulsion carriers have adjuvant properties. Although herein primarily the HSV glycoproteins that are discussed are from HSV-2, glycoproteins from HSV-1 may also be used.

In certain embodiments, the glycoprotein or the structural protein or both may be a precursor protein, a mature protein, a fragment, a fusion protein, or a peptide. The glycoprotein and structural protein elements may be part of the same or different fusion proteins. Similarly, if there is more than one glycoprotein or more than one structural protein, they may be part of a single fusion protein or parts of separate fusion proteins. If there is more than one glycoprotein or more than one structural protein, each of the more than one proteins can be a precursor protein, mature protein, fragment, etc. that is, for example, two glycoproteins may comprise a fragment and a peptide or for example, two different fragments of the same glycoprotein or for example, two fragments of different glycoproteins.

The amount of each of the proteins or immunologic fragments in each vaccine dose typically ranges from about 0.5 μg to about 50 μg, or about 0.5 μg, about 1.0 μg, about 2 μg, about 5 μg, about 10 μg, about 15 μg, about 20 μg, about 30 μg, about 40 μg, about 50 μg, about 75 μg, about 100 µg, or about 15 µg or about 200 µg or about 250 µg or any other suitable amount that would be determined to provide efficacy against HSV-2. The proteins or immunologic fragments may be present in a variety of ratios, including equimolar ratios, which provides equal epitope representation, and equimass ratios, which provides equal mass of each individual protein. Equimolar and equimass ratios that are within about 20% (e.g., 0.8:1.2), or within about 10% (e.g., 0.9:1.1) or within about 5% (e.g., 0.95: 1.05) of equivalence are still considered to be equimolar or equimass. The dose will typically be determined by pharmacological activity of the composition, purpose (therapeutic or prophylactic), and the size and condition of the subject.

The proteins may be supplied as a solution, but can also be desiccated (dry) in which case, a user adds the necessary liquid. Typically, additives such as buffers, stabilizers, tonicity agents, surfactants, preservatives, carriers, and other non-active ingredients will also be present. The additives are typically pharmaceutically acceptable and bio-compatible. Preferably, the additives, immunogens, agents, etc. are substantially free of other endotoxins, toxic compounds, and contaminants that can cause unwanted side-effects. Formulations may vary according to the route of administration. For example, a formulation for administration by i.m. injection will generally be isotonic and aqueous, while a formulation for oral administration may be encapsulated as a slow-release form or contain flavors. Formations for aerosol administration will generally be packaged under pressure and contain a propellant.

The agent, which may be an adjuvant, may be provided as a solution, desiccated, or emulsified, generally as a stable oil-in-water emulsion. Any of these may also comprise buffers, stabilizers, preservatives, carriers, or other non-active ingredients. The additives are typically pharmaceutically acceptable and bio-compatible. More than one agent may be present, and one, some or all of the agents may also be an adjuvant or co-adjuvant. In addition, an adjuvant, or co-adjuvant, that is not also an agent may also be provided. Antigen depots, such as oils or at least some oil emulsions may also be present.

The amount of an adjuvant agent such as GLA or another MALA adjuvant is typically about 0.5 µg, about 1 µg, about 2 µg, about 2.5 µg, about 5 µg, about 7.5 µg, about 10 µg, about 15 µg, about 20 µg or about 25 µg. An emulsion, such as SE, may be present at about 0.1%, about 0.5%, about 1.0%, about 1.5%, about 2%, about 2.5%, about 3%, about 4%, about 5%, about 7.5% or about 10%

The agent and proteins may be provided in separate containers and mixed on-site or pre-mixed. In addition, the proteins may be presented in separate containers or combined in a single container. The agent and proteins may be provided in a concentrated form and provided with a diluent. Suitable diluents include saline and PBS. A container can a vial, ampoule, tube, well of a multi-well device, reservoir, syringe or any other kind of container. The container or containers may be provided as a kit. If one or more of the containers comprises desiccated ingredients the liquids for reconstitution may be provided in the kit as well or provided by the user. The amount of solution in each container or that is added to each container is commensurate with the route of administration and how many doses are in each container. A vaccine given by injection is typically from about 0.1 ml to about 2.0 ml, while a vaccine that is given orally may be a larger volume, from about 1 ml to about 10 ml for example. Suitable volumes may also vary according to the size and age of the subject.

2. Administration

The composition may be used for treatment of an HSV-2 infection in subjects. As used herein, "treatment" is a clinical intervention that may be therapeutic or prophylactic. In therapeutic applications, pharmaceutical compositions or medicants are administered to a subject suspected of having or known to have an HSV-2 infection. The composition is given in an amount sufficient to generate (induce) an immune response that can cure, or at least partially arrest, the symptoms of the disease and its complications. In prophylactic applications, pharmaceutical compositions or medicants are administered to a subject susceptible to, or otherwise at risk of, an HSV-2 infection in an amount sufficient to induce an immune response that will inhibit infection or reduce the risk or delay the outset of the disease or ameliorate one or more of the effects of infection. An amount adequate to accomplish this is defined as a therapeutically- or pharmaceutically-effective dose. Such an amount can be administered as a single dosage or can be administered according to a regimen, whereby it is effective. The amount can cure a disease but, typically, is administered in order to ameliorate the symptoms of a disease, or to effect prophylaxis of a disease or disorder from developing.

In both therapeutic and prophylactic regimes, agents are usually administered in several dosages until a sufficient immune response has been achieved. Typically, the immune response is monitored and repeated dosages are given if the immune response starts to fade. Treatment need not completely eliminate a disease, nor need it completely prevent a subject from becoming ill with the disease or disorder. In some embodiments, only a single dosage is administered. More often, multiple dosages will be administered. Generally, the first dosage is called a "priming" dosage and the second and subsequence dosages are called "boosting" dosages. Multiple dosages may consist of two administrations, of three administrations, of four administrations, and at times, of five or more administrations. Ideally, the number is one or two administrations. When multiple administrations are provided, the timing of the second, and subsequent, administrations will generally be at least two weeks following the last administration, and may be at least one month, two months, three months, six months, or 1 year following the last administration. Ideally, an immune response is monitored in order to determine if multiple dosages would be advantageous. The multiple dosages may contain equivalent amount of immunogens and agonist or may contain different amounts of these ingredients. For example, a boosting dosage may comprise lower amounts of immunogens. Furthermore, additives may differ between dosages.

In some embodiments, the priming composition that is administered to the subject is a live attenuated HSV-2 virus and the boosting composition that is administered to the subject is any composition claimed or described herein. In some embodiments, the priming composition that is administered to the subject is any composition claimed or described herein and the boosting composition that is administered to the subject is a live attenuated HSV-2 virus.

Whether used as a prophylactic or as a therapeutic, administration preferably raises an immune response to HSV-2. The immune response can be humoral (antibody mediated) or cellular (typically, although not exclusively T cell mediated) or both. The immunized subject may also have activated monocytes, macrophages, NK cells, dendritic cells, and other innate immune cell types. Assays for an immune response are described herein and are well known by one of average skill.

Vaccine is administered at a dose sufficient to effect a beneficial therapeutic response (therapeutically effective dose) e.g., effective immune response to ameliorate, alleviate, cure or partially ameliorate symptoms of disease or infection, or prophylactic response, e.g., prevent infection or disease symptoms. Indicators of a beneficial therapeutic response is fewer herpes lesions in any given outbreak or a lower number of lesions on average, or less frequent outbreaks. Other indicators include smaller lesions, lesions that heal more quickly, inure less pain. Still other indicators are development of antibodies to HSV-2 vaccine components, in particular presence of antibodies to HSV-2 envelope glycoproteins, e.g., antibodies to gD2, and also particularly development of neutralizing antibodies. There are many well known procedures to detect and quantify antibodies, including ELISA and inhibition of virus infection (neutralization) assays. In one implementation, the ELISA assay is performed by coating wells of a multi-well plate with gD2 protein, capturing gD2-specific antibody from serum onto the plates, detecting the gD2-specific antibody with labeled anti-human antibody, followed by a readout of the label. Label can be radioactive, but is more usually an enzyme, such as horse radish peroxidase, that converts a substrate to one that can be detected colorimetrically. An exemplary HSV neutralization assay is based on a plaque assay in which neutralizing antibody is detected by inhibition of plaque formation. Other indicators include an increased amount or function or frequency of CD8 or CD4 T cells responsive to HSV-2, a reduction in virus shedding, reduction in viral transmission to sexual partners, and reduction of size or frequency or both of symptomatic lesions.

Assays for T cell function include IFN-γ ELISPOT and ICS (intracellular cytokine staining). The ELISPOT assay detecting interferon-gamma is widely used to quantize CD4 and CD8 T cell responses to candidate vaccines. The ELISPOT assay is based on the principle of the ELISA detecting antigen-induced secretion of cytokines trapped by an immobilized antibody and visualized by an enzyme-coupled second antibody. ICS is a routinely used method to quantify cytotoxic T cells by virtue of cytokine expression following stimulation with agonists, such as antibodies to T cell surface molecules or peptides that bind MHC Class molecules. Exemplary procedures of ICS and ELISPOT are described below.

Subjects to receive the vaccine include both HSV-2 seropositive and HSV-2 seronegative individuals. For seropositive individuals, the vaccine is intended to be therapeutic. For seronegative individuals, the vaccine is intended to be protective. In some cases, subjects are seropositive for HSV-1 and in other cases, are seronegative for HSV-1, independent of HSV-2 status. That is, subjects may include those who are HSV-1 seropositive/HSV-2 seropositive, HSV-1 seronegative/HSV-2 seropositive, HSV-1 seropositive/HSV-2 seronegative, HSV-1 seronegative/HSV-2 seronegative. Moreover, subjects include human and other mammalian subjects that can be infected by HSV-2.

The vaccine can be administered by any suitable delivery route, such as intradermal, mucosal (e.g., intranasal, oral), intramuscular, subcutaneous, sublingual, rectal, and vaginal. Other delivery routes are well known in the art.

The intramuscular route is one suitable route for the composition. Suitable i.m. delivery devices include a needle and syringe, a needle-free injection device (for example Biojector, Bioject, Oreg. USA), or a pen-injector device, such as those used in self-injections at home to deliver insulin or epinephrine. Intradermal and subcutaneous delivery are other suitable routes. Suitable devices include a syringe and needle, syringe with a short needle, and jet injection devices.

The composition may be administered by a mucosal route, e.g., intranasally. Many intranasal delivery devices are available and well known in the art. Spray devices are one such device. Oral administration can as simple as providing a solution for the subject to swallow.

Vaccine may be administered at a single site or at multiple sites. If at multiple sites, the route of administration may be the same at each site, e.g., injection in different muscles, or may be different, e.g., injection in a muscle and intranasal spray. Furthermore, the vaccine may be administered at a single time point or multiple time points. Generally if administered at multiple time points, the time between doses has been determined to improve the immune response.

Recombinant Expression Vectors, Viral Vectors, and Virus-Like Particles

In one embodiment, recombinant expression vectors are provided that comprise a polynucleotide sequence encoding at least one HSV2 immunogen that induces an immune response to the immunogen and to its respective designated antigen. To obtain efficient transcription and translation of the immunogen, the encoding polynucleotide sequences in each vector include at least one appropriate expression control sequence (also called a regulatory expression sequence or feature) (e.g., promoter, enhancer, leader), which are described in greater detail herein, that is operatively linked to the encoding polynucleotide sequence(s). These recombinant expression vectors are thus provided for directing expression of the immunogen or for directing co-expression of at least two immunogens in any appropriate host cell that has been transformed, transduced, or transfected with the recombinant expression vector or vector particle containing the recombinant expression vector.

The recombinant expression vectors described herein may encode one or more HSV-2 immunogens (i.e., at least one, at least two, at least three immunogens, etc.), which immunogens are described in greater detail herein. In particular embodiments, at least one, two, or three, or more immunogens from HSV-2 may be encoded by a recombinant expression vector. By way of example, an immunogen may be an HSV-2 protein, such as UL19 (e.g., UL19 Upper Domain Fragment or an immunogenic fragment or variant thereof) and/or gD, (or an immunogenic fragment or variant thereof) and/or UL47 (or an immunogenic fragment or variant thereof), or may be another immunogenic fragment or region of the HSV-2 protein.

A. Recombinant Production of Protein

A recombinant expression vector that comprises a polynucleotide sequence that encodes an immunogen may be used for production of the immunogen. Recombinant expression vectors include at least one regulatory expression sequence, such as a promoter or enhancer, that is operatively linked to the polynucleotide encoding the immunogen. Each of the expression vectors may be used to transform, transducer, or transfect an appropriate host cell for recombinant production of a respective immunogen. Suitable host cells for production of the immunogen include prokaryotes, yeast and higher eukaryotic cells (e.g., CHO and COS). The immunogen may each be isolated from the respective host cell or host cell culture using any one of a variety of isolation methods (e.g., filtration, diafiltration, chromatography (including affinity chromatography, high pressure liquid chromatography), and preparative electrophoresis) known and routinely practiced in the protein art. In certain embodiments, as described herein, the isolated immunogen may then be formulated with a pharmaceutically suitable excipient to provide an immunogenic composition.

Particular methods for producing polypeptides recombinantly are generally well known and routinely used. For example, molecular biology procedures are described by Sambrook et al. (Molecular Cloning, A Laboratory Manual, 2nd ed., Cold Spring Harbor Laboratory, New York, 1989; see also Sambrook et al., 3rd ed., Cold Spring Harbor Laboratory, New York, (2001)). DNA sequencing can be performed as described in Sanger et al. (Proc. Natl. Acad. Sci. USA 74:5463 (1977)) and the Amersham International plc sequencing handbook and including improvements thereto.

B. Recombinant Expression Vectors for Delivery of Protein to Subjects

Recombinant expression vectors may be used for expression of any one or more of the immunogens described herein. In particular embodiments, the recombinant expression vector is delivered to an appropriate cell (for example, an antigen-presenting cell i.e., a cell that displays a peptide/MHC complex on its cell surface, such as a dendritic cell) or tissue (e.g., lymphoid tissue) that will induce the desired immune response (i.e., a specific humoral response (i.e., B cell response) and/or induction of a specific cell-medicated immune response, which may include an immunogen-specific CD4 and/or CD8 T cell response, which CD8 T cell response may include a cytotoxic T cell (CTL) response). The recombinant expression vectors may therefore also include, for example, lymphoid tissue-specific transcriptional regulatory elements (TRE) such as a B lymphocyte, T lymphocyte, or dendritic cell specific TRE. Lymphoid tissue specific TRE are known in the art (see, e.g., Thompson et al., Mol. Cell. Biol. 12, 1043-53 (1992); Todd et al., J. Exp. Med. 177, 1663-74 (1993); Penix et al., J. Exp. Med. 178:1483-96 (1993)).

In a particular embodiment, the recombinant expression vector is plasmid DNA or cosmid DNA. Plasmid DNA or cosmid DNA containing one or more polynucleotides encoding an immunogen as described herein is readily constructed using standard techniques well known in the art. The vector genome may be typically constructed in a plasmid form that can then be transfected into a packaging or producer cell line. The plasmid generally comprises sequences useful for replication of the plasmid in bacteria. Such plasmids are well known in the art. In addition, vectors that include a prokaryotic origin of replication may also include a gene whose expression confers a detectable or selectable marker such as a drug resistance. Typical bacterial drug resistance products are those that confer resistance to ampicillin or tetracycline. For analysis to confirm that the correct nucleotide sequences are incorporated in plasmids, the plasmid may be replicated in *E. coli*, purified, and analyzed by restriction endonuclease digestion and/or its nucleotide sequence determined by conventional methods.

C. Viral Vectors

In other particular embodiments, the recombinant expression vector is a viral vector. Exemplary recombinant expression viral vectors include a lentiviral vector genome, poxvirus vector genome, vaccinia virus vector genome, adenovirus vector genome, adenovirus-associated virus vector genome, herpes virus vector genome, and alpha virus vector genome. Viral vectors may be live, attenuated, replication conditional or replication deficient, and typically is a non-pathogenic (defective), replication competent viral vector.

By way of example, in a specific embodiment, when the viral vector is a vaccinia virus vector genome, the polynucleotide encoding an immunogen of interest may be inserted into a non-essential site of a vaccinia viral vector. Such non-essential sites are described, for example, in Perkus et al., Virology 152:285 (1986); Hruby et al., Proc. Natl. Acad. Sci. USA 80:3411 (1983); Weir et al., J. Virol. 46:530 (1983). Suitable promoters for use with vaccinia viruses include but are not limited to P7.5 (see, e.g., Cochran et al., J. Virol. 54:30 (1985); P11 (see, e.g., Bertholet, et al., Proc. Natl. Acad. Sci. USA 82:2096 (1985)); and CAE-1 (see, e.g., Patel et al., Proc. Natl. Acad. Sci. USA 85:9431 (1988)). Highly attenuated strains of vaccinia are more acceptable for use in humans and include Lister, NYVAC, which contains specific genome deletions (see, e.g., Guerra et al., J. Virol. 80:985-98 (2006); Tartaglia et al., AIDS Research and Human Retroviruses 8:1445-47 (1992)), or MVA (see, e.g., Gheradi et al., J. Gen. Virol. 86:2925-36 (2005); Mayr et al., Infection 3:6-14 (1975)). See also Hu et al. (J. Virol. 75:10300-308 (2001), describing use of a Yaba-Like disease virus as a vector for cancer therapy); U.S. Pat. Nos. 5,698,530 and 6,998,252. See also, e.g., U.S. Pat. No. 5,443,964. See also U.S. Pat. Nos. 7,247,615 and 7,368,116.

In certain embodiments, an adenovirus vector or adenovirus-associated virus vector may be used for expressing an immunogen of interest. Several adenovirus vector systems and methods for administering the vectors have been described (see, e.g., Molin et al., J. Virol. 72:8358-61 (1998); Narumi et al., Am J. Respir. Cell Mol. Biol. 19:936-41 (1998); Mercier et al., Proc. Natl. Acad. Sci. USA 101:6188-93 (2004); U.S. Pat. Nos. 6,143,290; 6,596,535; 6,855,317; 6,936,257; 7,125,717; 7,378,087; 7,550,296).

Retroviral vector genomes may include those based upon murine leukemia virus (MuLV), gibbon ape leukemia virus (GaLV), ecotropic retroviruses, simian immunodeficiency virus (SIV), human immunodeficiency virus (HIV), and combinations (see, e.g., Buchscher et al., J. Virol. 66:2731-39 (1992); Johann et al., J. Virol. 66:1635-40 (1992); Sommerfelt et al., Virology 176:58-59 (1990); Wilson et al., J. Virol. 63:2374-78 (1989); Miller et al., J. Virol. 65:2220-24 (1991); Miller et al., Mol. Cell. Biol. 10:4239 (1990); Kolberg, NIH Res. 4:43 1992; Cornetta et al., Hum. Gene Ther. 2:215 (1991)).

D. Lentiviral Vectors

In a more specific embodiment, the recombinant expression viral vector is a lentiviral vector genome. The genome can be derived from any of a large number of suitable, available lentiviral genome based vectors, including those identified for human gene therapy applications (see, e.g., Pfeifer et al., Annu. Rev. Genomics Hum. Genet. 2:177-211 (2001)). Suitable lentiviral vector genomes include those based on Human Immunodeficiency Virus (HIV-1), HIV-2, feline immunodeficiency virus (FIV), equine infectious anemia virus, Simian Immunodeficiency Virus (SIV), and maedi/visna virus. A desirable characteristic of lentiviruses is that they are able to infect both dividing and non-dividing cells, although target cells need not be dividing cells or be stimulated to divide. Generally, the genome and envelope glycoproteins will be based on different viruses, such that the resulting viral vector particle is pseudotyped. Safety features of the vector genome are desirably incorporated. Safety features include self-inactivating LTR and a non-integrating genome. Exemplary vectors contain a packaging signal (psi), a Rev-responsive element (RRE), splice donor, splice acceptor, central poly-purine tract (cPPT), and WPRE element. In certain exemplary embodiments, the viral vector genome comprises sequences from a lentivirus genome, such as the HIV-1 genome or the SIV genome. The viral genome construct may comprise sequences from the 5' and 3' LTRs of a lentivirus, and in particular may comprise the R and U5 sequences from the 5' LTR of a lentivirus and an inactivated or self-inactivating 3' LTR from a lentivirus. The LTR sequences may be LTR sequences from any lentivirus from any species. For example, they may be LTR sequences from HIV, SIV, FIV or BIV. Typically, the LTR sequences are HIV LTR sequences.

The vector genome may comprise an inactivated or self-inactivating 3' LTR (see, e.g., Zufferey et al., J. Virol. 72: 9873, 1998; Miyoshi et al., J. Virol. 72:8150, 1998; both of which are incorporated in their entirety). A self-inactivating vector generally has a deletion of the enhancer and promoter sequences from the 3' long terminal repeat (LTR), which is copied over into the 5' LTR during vector integration. In one instance, the U3 element of the 3' LTR contains a deletion of its enhancer sequence, the TATA box, Sp1 and NF-kappa B sites. As a result of the self-inactivating 3' LTR, the provirus that is generated following entry and reverse transcription will comprise an inactivated 5' LTR. The rationale is to improve safety by reducing the risk of mobilization of the vector genome and the influence of the LTR on nearby cellular promoters. The self-inactivating 3' LTR may be constructed by any method known in the art.

Optionally, the U3 sequence from the lentiviral 5' LTR may be replaced with a promoter sequence in the viral construct, such as a heterologous promoter sequence. This can increase the titer of virus recovered from the packaging cell line. An enhancer sequence may also be included. Any enhancer/promoter combination that increases expression of the viral RNA genome in the packaging cell line may be used. In one example, the CMV enhancer/promoter sequence is used (see, e.g., U.S. Pat. Nos. 5,385,839 and 5,168,062).

In certain embodiments, the risk of insertional mutagenesis is minimized by constructing the lentiviral vector genome to be integration defective. A variety of approaches can be pursued to produce a non-integrating vector genome. These approaches entail engineering a mutation(s) into the integrase enzyme component of the pol gene, such that it encodes a protein with an inactive integrase. The vector genome itself can be modified to prevent integration by, for example, mutating or deleting one or both attachment sites, or making the 3' LTR-proximal polypurine tract (PPT) non-functional through deletion or modification. In addition, non-genetic approaches are available; these include pharmacological agents that inhibit one or more functions of integrase. The approaches are not mutually exclusive, that is, more than one of them can be used at a time. For example, both the integrase and attachment sites can be non-functional, or the integrase and PPT site can be non-functional, or the attachment sites and PPT site can be non-functional, or all of them can be non-functional.

Integrase is involved in cleavage of viral double-stranded blunt-ended DNA and joining the ends to 5'-phosphates in the two strands of a chromosomal target site. Integrase has three functional domains: N-terminal domain, which contains a zinc-binding motif (HHCC); the central domain core, which contains the catalytic core and a conserved DD35E motif (D64, D116, E152 in HIV-1); and a C-terminal domain, which has DNA binding properties. Point mutations introduced into integrase are sufficient to disrupt normal function. Many integrase mutations have been constructed and characterized (see, e.g., Philpott and Thrasher, Human Gene Therapy 18:483, 2007; Apolonia, Thesis submitted to University College London, April 2009, pp, 82-97; Engelman et al., J. Virol. 69: 2729, 1995; Nightingale et al., Mol. Therapy, 13: 1121, 2006). The sequence encoding the integrase protein can be deleted or mutated to render the protein inactive, preferably without significantly impairing reverse transcriptase activity or nuclear targeting, thereby only preventing integration of the provirus into the target cell genome. Acceptable mutations can reduce integrase catalysis, strand transfer, binding to att sites, binding to host chromosomal DNA, and other functions. For example, a single aspartic acid to asparagine substitution at residue 35 of HIV or SIV integrase completely abolishes viral DNA integration. Deletions of integrase will generally be confined to the C-terminal domain. Deletion of coding sequence for residues 235-288 result in a useful non-functional integrase (see, e.g., Engelman et al., J. Virol. 69:2729, 1995). As further examples, mutations can be generated, for example, Asp64 (residue numbers are given for HIV-1, corresponding residue numbers for integrase from other lentiviruses or retroviruses can be readily determined by one of ordinary skill) (e.g., D64E, D64V), Asp116 (e.g., D116N), Asn120 (e.g., N120K), Glu152, Gln148 (e.g., Q148A), Lys156, Lys159, Trp235 (e.g., W235E), Lys264 (e.g., K264R), Lys266 (e.g., K266R), Lys273 (e.g., K273R). Other mutations can be constructed and tested for integration, transgene expression, and any other desirable parameter. Assays for these functions are well known. Mutations can be generated by any of a variety of techniques, including site-directed mutagenesis and chemical synthesis of nucleic acid sequence. One mutation may be made or more than one of these mutations can be present in integrase. For example, an integrase may have mutations at two amino acids, three amino acids, four amino acids, and so on.

Alternatively or in combination with the use of integrase mutant(s), the attachment sites (att) in U3 and U5 can also be mutated. Integrase binds to these sites and the 3'-terminal dinucleotide is cleaved at both ends of the vector genome. A CA dinucleotide is located at the recessed 3' end; the CA is required for processing, mutation of the nucleotides blocks integration into the host chromosome. The A of the CA dinucleotide is the most critical nucleotide for integration, and mutations at both ends of the genome will give the best results (see, e.g., Brown et al., J. Virol. 73:9011 (1999)). In one exemplification, the CA at each end is changed to TG. In other exemplifications, the CA at each end is changed to TG at one end and GT at the other end. In other exemplifications, the CA at each end is deleted; in other exemplifications, the A of the CA is deleted at each end.

Integration can also be inhibited by mutation or deletion of polypurine tract (PPT) (see, e.g., WO 2009/076524), located proximally to the 3' LTR. The PPT is a polypurine sequence of about 15 nucleotides that can serve as a primer binding site for plus-strand DNA synthesis. In this instance, mutations or deletions of PPT targets the reverse transcription process. Without wishing to be held to a particular mechanism, by mutating or deleting PPT, production of linear DNA is radically reduced, and essentially only 1-LTR DNA circles are produced. Integration requires a linear double-stranded DNA vector genome, and integration is essentially eliminated without it. As stated herein, a PPT can be made non-functional by mutation or by deletion. Typically, the entire about 15 nt PPT is deleted, although in some embodiments, shorter deletions of 14 nt, 13, nt, 12 nt, 11 nt, 10 nt, 9 nt, 8 nt, 7 nt, 6 nt, 5 nt, 4 nt, 3 nt and 2 nt may be made. When mutations are made, typically multiple mutations are made, especially in the 5' half of the PPT (see, e.g., McWilliams et al., J. Virol. 77:11150, 2003), although single and double mutations in the first four bases still reduce transcription. Mutations made at the 3' end of PPT generally have a more dramatic effect (see, e.g., Powell et al., J. Virol. 70:5288, 1996).

The U3 region may comprise a PPT (polypurine tract) sequence immediately upstream. In certain specific embodiments, any one of at least three different U3 regions (at the 3' end) may be included in the lentiviral vector (see SEQ ID NOS:13-15). The constructs contain deletions in the U3 regions. The SIN construct has a deletion of about 130 nucleotides in the U3 (see, e.g., Miyoshi, et al. J. Virol. 72: 8150, 1998; Yu et al., Proc. Natl. Acad. Sci. USA 83: 3194, 1986), which removes the TATA box, thereby abolishing LTR promoter activity. The deletions in constructs 703 and 704 increase expression from lentivirus vectors (see, e.g., Bayer et al., Mol. Therapy. 16: 1968, 2008). In addition, construct 704 contains a deletion of the 3' PPT, which decreases integration of the vector (see, e.g., WO 2009/076524). See also U.S. patent application Ser. No. 12/842,609 and International Patent Application Publication No. WO 2011/011584 (International Patent Application No. PCT/US10/042,870), which are each incorporated by reference in their entirety.

These different approaches to make a vector genome non-integrating can be used individually or in combination. Using more than one approach may be used to build a fail-safe vector through redundant mechanisms. Thus, PPT mutations or deletions can be combined with att site mutations or deletions or with Integrase mutations or PPT mutations or deletions can be combined with both att site mutations or deletions and Integrase mutations. Similarly, att site mutations or deletions and Integrase mutations may be combined with each other or with PPT mutations or deletions.

As described herein, lentiviral vector constructs may also contain a promoter for expression in mammalian cells. Promoters, which are discussed in greater detail herein, include, for example, the human ubiquitin C promoter (UbiC), the cytomegalovirus immediate early promoter (CMV), and the Rous sarcoma virus (RSV) promoter.

E. Virus-Like Particles

In various embodiments, virus-like particles (VLP) are provided that comprise a at least one HSV2 immunogen that induces an immune response to the immunogen and to its respective designated antigen.

An HSV-1 or HSV-2 virus-like particle can be prepared by allowing VP5, VP19, VP23, VP22a, and the maturational protease (UL26 gene product) to self-assemble in vitro. See, for example, Newcomb et al., *J. Virol, September* 1994, 6059-6063.; Newcomb et al., *J. Mol. Biol.*, 263; 432-446 (1996); Thomsen et al., *J Virol*, April 1994, 2442-2457; all incorporated by reference in their entirety. The virus-like particles described herein may comprise one or more HSV-2 immunogens (i.e., at least one, at least two, at least three immunogens, etc.), which immunogens are described in greater detail herein. In particular embodiments, at least one, two, or three, or more immunogens from HSV-2 may be enclosed in or associated with a virus-like particle. By way of example, an immunogen may be an HSV-2 protein, such as UL19 (e.g., UL19 Upper Domain Fragment or an immunogenic fragment or variant thereof) and/or gD, (or an immunogenic fragment or variant thereof) and/or UL47 (or an immunogenic fragment or variant thereof), or may be another immunogenic fragment or region of the HSV-2 protein.

Regulatory Expression Sequences

As described herein, the recombinant expression vector comprises at least one regulatory expression sequence. In certain embodiments, when the recombinant expression vector comprises a viral vector genome, expression of the at least one immunogen is desired in particular target cells.

Typically, for example, in a lentiviral vector the polynucleotide sequence encoding the immunogen is located between the 5' LTR and 3' LTR sequences. Further, the encoding nucleotide sequence(s) is preferably operatively linked in a functional relationship with other genetic or regulatory sequences or features, for example transcription regulatory sequences including promoters or enhancers, that regulate expression of the immunogen in a particular manner. In certain instances, the useful transcriptional regulatory sequences are those that are highly regulated with respect to activity, both temporally and spatially. Expression control elements that may be used for regulating the expression of the encoded polypeptides are known in the art and include, but are not limited to, inducible promoters, constitutive promoters, secretion signals, enhancers, and other regulatory sequences.

The polynucleotide encoding the immunogen and any other expressible sequence is typically in a functional relationship with internal promoter/enhancer regulatory sequences. With respect to lentiviral vector constructs, an "internal" promoter/enhancer is one that is located between the 5' LTR and the 3' LTR sequences in the viral vector and is operatively linked to the encoding polynucleotide sequence of interest. The internal promoter/enhancer may be any promoter, enhancer or promoter/enhancer combination known to increase expression of a gene with which it is in a functional relationship. A "functional relationship" and "operatively linked" mean, without limitation, that the sequence is in the correct location and orientation with respect to the promoter and/or enhancer such that the sequence of interest will be expressed when the promoter and/or enhancer is contacted with the appropriate molecules.

The choice of an internal promoter/enhancer is based on the desired expression pattern of the immunogen and the specific properties of known promoters/enhancers. Thus, the internal promoter may be constitutively active. Non-limiting examples of constitutive promoters that may be used include the promoter for ubiquitin (see, e.g., U.S. Pat. No. 5,510,474; WO 98/32869); CMV (see, e.g., Thomsen et al., Proc. Natl. Acad. Sci. USA 81:659, 1984; U.S. Pat. No. 5,168,062); beta-actin (Gunning et al. 1989 Proc. Natl. Acad. Sci. USA 84:4831-4835); and pgk (see, for example, Adra et al. 1987 Gene 60:65-74; Singer-Sam et al. 1984 Gene 32:409-417; and Dobson et al. 1982 Nucleic Acids Res. 10:2635-2637).

Alternatively, the promoter may be a tissue specific promoter. In some embodiments, the promoter is a target cell-specific promoter. Targeting dendritic cells may enhance the immune response, particularly the cellular cytotoxic response that is useful for immunity for HSV-2. For example, the promoter can be from any product expressed by dendritic cells, including CD11c, CD103, TLRs, DC-SIGN, BDCA-3, DEC-205, DCIR2, mannose receptor, Dectin-1, Clec9A, MHC class II. In addition, promoters may be selected to allow for inducible expression of the immunogen. A number of systems for inducible expression are known in the art, including the tetracycline responsive system, the lac operator-repressor system, as well as promoters responsive to a variety of environmental or physiological changes, including heat shock, metal ions, such as metallothionein promoter, interferons, hypoxia, steroids, such as progesterone or glucocorticoid receptor promoter, radiation, such as VEGF promoter. A combination of promoters may also be used to obtain the desired expression of each of the immunogen-encoding polynucleotide sequences. The artisan of ordinary skill will be able to select a promoter based on the desired expression pattern of the polynucleotide sequence in the organism or the target cell of interest.

A recombinant expression vector, including a viral vector genome, may comprise at least one RNA Polymerase II or III responsive promoter. This promoter can be operatively linked to the polynucleotide sequence of interest and can also be linked to a termination sequence. In addition, more than one RNA Polymerase II or III promoter may be incorporated. RNA polymerase II and III promoters are well known to persons of skill in the art. A suitable range of RNA polymerase III promoters can be found, for example, in Paule and White, Nucleic Acids Res., Vol. 28, pp 1283-1298 (2000). RNA polymerase II or III promoters also include any synthetic or engineered DNA fragment that can direct RNA polymerase II or III to transcribe downstream RNA coding sequences. Further, the RNA polymerase II or III (Pol II or III) promoter or promoters used as part of the viral vector genome can be inducible. Any suitable inducible Pol II or III promoter can be used with the methods described herein. Particularly suited Pol II or III promoters include the tetracycline responsive promoters provided in Ohkawa and Taira, Human Gene Therapy, 11:577-585 (2000) and in Meissner et al., Nucleic Acids Res., 29:1672-1682 (2001).

An internal enhancer may also be present in the recombinant expression vector, including a viral vector genome, to increase expression of the polynucleotide sequence of interest. For example, the CMV enhancer (see, e.g., Boshart et al., Cell 41:521, 1985) may be used. Many enhancers in viral genomes, such as HIV, CMV, and in mammalian genomes have been identified and characterized (see, e.g., publically available databases such as GenBank). An enhancer can be used in combination with a heterologous promoter. One of ordinary skill in the art will be able to select the appropriate enhancer based on the desired expression pattern.

When targeting delivery of a recombinant expression vector, including a viral vector genome, to a particular target cell, the vector genome will usually contain a promoter that is recognized by the target cell and that is operatively linked to the sequence of interest, viral components (when the vector is a viral vector), and other sequences discussed herein. A promoter is an expression control element formed by a nucleic acid sequence that permits binding of RNA polymerase and transcription to occur. Promoters may be inducible, constitutive, temporally active or tissue specific. The activity of inducible promoters is induced by the presence or absence of biotic or abiotic factors. Inducible promoters can be a useful tool in genetic engineering because the expression of genes to which they are operatively linked can be turned on or off at certain stages of development of an organism, its manufacture, or in a particular tissue. Inducible promoters can be grouped as chemically-regulated promoters, and physically-regulated promoters. Typical chemically-regulated promoters include, not are not limited to, alcohol-regulated promoters (e.g., alcohol dehydrogenase I (alcA) gene promoter), tetracycline-regulated promoters (e.g., tetracycline-responsive promoter), steroid-regulated promoter (e.g., rat glucocorticoid receptor (GR)-based promoter, human estrogen receptor (ER)-based promoter, moth ecdysone receptor-based promoter, and the promoters based on the steroid/retinoid/thyroid receptor superfamily), metal-regulated promoters (e.g., metallothionein gene-based promoters), and pathogenesis-related promoters (e.g., *Arabidopsis* and maize pathogen-related (PR) protein-based promoters). Typical physically-regulated promoters include, but are not limited to, temperature-regulated promoters (e.g., heat shock promoters), and light-regulated promoters (e.g., soybean SSU promoter). Other exemplary promoters are described elsewhere, for example, in patents and published patent applications that can be identified by searching the U.S. Patent and Trademark Office databases.

One of skill in the art will be able to select an appropriate promoter based on the specific circumstances. Many different promoters are well known in the art, as are methods for operatively linking the promoter to the polynucleotide sequence to be expressed. Both native promoter sequences and many heterologous promoters may be used to direct expression in the packaging cell and target cell. Heterologous promoters are typically used because they generally permit greater transcription and higher yields of the desired protein as compared to the native promoter.

The promoter may be obtained, for example, from the genomes of viruses such as polyoma virus, fowlpox virus, adenovirus, bovine papilloma virus, avian sarcoma virus, cytomegalovirus, a retrovirus, hepatitis-B virus, and Simian Virus 40 (SV40). The promoter may also be, for example, a heterologous mammalian promoter, for example, the actin promoter or an immunoglobulin promoter, a heat-shock promoter, or the promoter normally associated with the native sequence, provided such promoters are compatible with the target cell. In one embodiment, the promoter is the naturally occurring viral promoter in a viral expression system. In some embodiments, the promoter is a dendritic cell-specific promoter. The dendritic cell-specific promoter can be, for example, CD11c promoter.

Transcription may be increased by inserting an enhancer sequence into the vector(s). Enhancers are typically cis-acting elements of DNA, usually about 10 to 300 base pairs in length, that act on a promoter to increase its transcription. Many enhancer sequences are now known from mammalian genes (globin, elastase, albumin, alpha-fetoprotein, and insulin) and from eukaryotic cell viruses. Examples include the SV40 enhancer on the late side of the replication origin (base pair 100-270), the cytomegalovirus early promoter enhancer, the polyoma enhancer on the late side of the replication origin, and adenovirus enhancers. The enhancer may be spliced into the vector at a position 5' or 3' to the antigen-specific polynucleotide sequence, but is preferably located at a site 5' from the promoter.

Expression vectors may also contain sequences necessary for the termination of transcription and for stabilizing the mRNA. These sequences are often found in the 5' and, occasionally 3', untranslated regions of eukaryotic or viral DNAs or cDNAs and are well known in the art.

A recombinant expression construction, including a viral vector genome, may also contain additional genetic elements. The types of elements that may be included in the construct are not limited in any way and may be chosen to achieve a particular result. For example, a signal that facilitates nuclear entry of the recombinant expression vector or viral genome in the target cell may be included. An example of such a signal is the HIV-1 flap signal. Additional regulatory sequences may be included that facilitate the characterization of the provirus integration site in the target cell. For example, a tRNA amber suppressor sequence may be included in the construct. An insulator sequence, for example from chicken β-globin, may also be included in the viral genome construct. This element reduces the chance of silencing an integrated provirus in the target cell due to methylation and heterochromatinization effects. In addition, the insulator may shield the internal enhancer, promoter and exogenous polynucleotide sequences from positive or negative positional effects from surrounding DNA at the integration site on the chromosome. In addition, the recombinant construct, including the vector genome, may contain one or more genetic elements designed to enhance expression of the gene of interest. For example, a woodchuck hepatitis virus responsive element (WRE) may be placed into the construct (see, e.g., Zufferey et al. 1999. J. Virol. 74:3668-81; Deglon et al., 2000. Hum. Gene Ther. 11:179-90).

When the recombinant expression vector is a viral vector genome, the viral vector genome is typically constructed in a plasmid form that may be transfected into a packaging or producer cell line for production of the viral vector genome construct. The plasmid generally comprises sequences useful for replication of the plasmid in bacteria. Such plasmids are well known in the art. In addition, vectors that include a prokaryotic origin of replication may also include a gene whose expression confers a detectable or selectable marker such as a drug resistance. Typical bacterial drug resistance products are those that confer resistance to ampicillin or tetracycline.

In certain configurations, recombinant expression vectors contain polynucleotide sequences that encode dendritic cell (DC) maturation/stimulatory factors. Exemplary stimulatory molecules include GM-CSF, IL-2, IL-4, IL-6, IL-7, IL-15, IL-21, IL-23, TNFα, B7.1, B7.2, 4-1BB, CD40 ligand (CD40L), drug-inducible CD40 (iCD40), and the like. These polynucleotides are typically under the control of one or more regulatory elements that direct the expression of the coding sequences in dendritic cells. In certain other particular embodiments, a recombinant expression vector is excluded that directs expression of and includes a nucleotide sequence that encodes both an immunogen and GM-CSF. Maturation of dendritic cells contributes to successful vaccination (see, e.g., Banchereau et al., Nat. Rev. Immunol. 5:296-306 (2005); Schuler et al., Curr. Opin. Immunol. 15:138-147 (2003); Figdor et al., Nat. Med. 10:475-480 (2004)). Maturation can transform DCs from cells actively involved in antigen capture into cells specialized for T cell priming. For example, engagement of CD40 by CD40L on CD4-helper T cells is a critical signal for DC maturation, resulting in potent activation of CD8+ T cells. Such stimulatory molecules are also referred to as maturation factors or maturation stimulatory factors. Immune checkpoints represent significant barriers to activation of functional cellular immunity in cancer, and antagonistic antibodies specific for inhibitory ligands on T cells including CTLA4 and programmed death-1 (PD-1) are examples of targeted agents being evaluated in the clinics. A significant tolerance mechanism in chronic infections and cancer is the functional exhaustion of antigen-specific T cells that express high levels of PD-1. As the potency of therapeutic immunization has been shown to be significantly enhanced by combination with immune checkpoint control, as a non-limiting example, it can be appreciated by those of ordinary skill in the art that an alternative approach to inhibiting immune checkpoint is to inhibit the expression of programmed death (PD) ligands one and two (PD-L1/L2). One way to accomplish inhibition is by the expression of RNA molecules such as those described herein, which repress the expression of PD-L1/L2 in the DCs transduced with a viral vector genome, such as the lentivirus vector genome, encoding one or more of the relevant molecules. Maturation of DCs or expression of particular elements such as immune checkpoints, for example PD-1 ligands, can be characterized by flow cytometry analysis of up-regulation of surface marker such as MHC II, and by profiling expressed chemokines and cytokines, for example, by performing techniques and methods described herein.

A sequence encoding a detectable product, usually a protein, can be included to allow for identification of cells that are expressing the desired immunogen. For example, a fluorescent marker protein, such as green fluorescent protein (GFP), is incorporated into the recombinant expression construct along with a polynucleotide sequence of interest (i.e., encoding at least one immunogen). In other instances, the protein may be detectable by an antibody, or the protein may be an enzyme that acts on a substrate to yield a detectable product, or may be a protein product that allows selection of a transfected or transduced target cell, for example confers drug resistance, such as hygromycin resistance. Typical selection genes encode proteins that confer resistance to antibiotics or other toxins suitable for use in eukaryotic cells, for example, neomycin, methotrexate, blasticidine, among others known in the art, or complement auxotrophic deficiencies, or supply critical nutrients withheld from the media. The selectable marker can optionally be present on a separate plasmid and introduced by co-transfection.

With respect to vector particles described herein, one or more multicistronic expression units may be used that include two or more of a polynucleotide sequence encoding an immunogen, and a sequence encoding an envelope molecule as described herein or one or more DC maturation factors necessary for production of the desired vector particle in packaging cells. The use of multicistronic vectors reduces the total number of nucleic acid molecules required and thus may avoid the possible difficulties associated with coordinating expression from multiple vector genomes. In a multicistronic vector the various elements to be expressed are operatively linked to one or more promoters (and other expression control elements as necessary). In some configurations, a multicistronic vector comprises a sequence encoding an at least one immunogen (i.e., one or more) of interest, a sequence encoding a reporter product, and a sequence encoding one or more vector particle components. In certain embodiments in which the recombinant construct comprises a polynucleotide that encodes an immunogen, the construct optionally encodes a DC maturation factor. In certain other embodiments, a multicistronic vector comprises a polynucleotide sequences that encode each of an immunogen, a DC maturation factor, and optionally viral components when the expression vector is a viral expression vector. In still other embodiments, multicistronic vectors direct expression and encode at least two or more immunogens.

Each component to be expressed in a multicistronic expression vector may be separated, for example, by an internal ribosome entry site (IRES) element or a viral 2A element, to allow for separate expression of the various proteins from the same promoter. IRES elements and 2A elements are known in the art (see, e.g., U.S. Pat. No. 4,937,190; de Felipe et al. 2004. Traffic 5: 616-626). In one embodiment, oligonucleotides such as furin cleavage site sequences (RAKR) (see, e.g., Fang et al. Nat. Biotech. 23: 584-590) linked with 2A-like sequences from foot-and-mouth diseases virus (FMDV); equine rhinitis A virus (ERAV); and thosea asigna virus (TaV) (see, e.g., Szymczak et al. 2004 Nat. Biotechnol. 22: 589-594) are used to separate genetic elements in a multicistronic vector. The efficacy of a particular multicistronic vector can readily be tested by detecting expression of each of the genes using standard protocols.

In a specific exemplification, a viral vector genome comprises: a cytomegalovirus (CMV) enhancer/promoter sequence; the R and U5 sequences from the HIV 5' LTR; a packaging sequence (ψ); the HIV-1 flap signal; an internal enhancer; an internal promoter; a gene of interest; the woodchuck hepatitis virus responsive element; a tRNA amber suppressor sequence; a U3 element with a deletion of its enhancer sequence; the chicken β-globin insulator; and the R and U5 sequences of the 3' HIV LTR. In some exemplifications, the vector genome comprises an intact lentiviral 5' LTR and a self-inactivating 3' LTR (see, e.g., Iwakuma et al. Virology 15:120, 1999).

Construction of the vector genome can be accomplished using any suitable genetic engineering techniques known in the art, including, without limitation, the standard techniques of restriction endonuclease digestion, ligation, transformation, plasmid purification, and DNA sequencing, for example as described in Sambrook et al. (1989 and 2001 editions; Molecular Cloning: A Laboratory Manual, Cold Spring Harbor Laboratory Press, NY); Coffin et al. (Retroviruses. Cold Spring Harbor Laboratory Press, N.Y. (1997)); and "RNA Viruses: A Practical Approach" (Alan J. Cann, Ed., Oxford University Press, (2000), each of the foregoing which is incorporated herein by reference in its entirety.

Vectors constructed for transient expression in mammalian cells may also be used. Transient expression involves the use of an expression vector that is able to replicate efficiently in a host cell, such that the host cell accumulates many copies of the expression vector and, in turn, synthesizes high levels of a the polypeptide encoded by the immunogen-specific polynucleotide in the expression vector. See Sambrook et al., supra, pp. 16.17-16.22, 1989. Other vectors and methods suitable for adaptation to the expression of polypeptides are well known in the art and are readily adapted to the specific circumstances.

By using the teachings provided herein and the knowledge in the art, a person skilled in the art will recognize that the efficacy of a particular expression system can be tested by transfecting packaging cells with a vector comprising a polynucleotide sequence encoding a reporter protein and measuring the expression using a suitable technique, for example, measuring fluorescence from a green fluorescent protein conjugate. Other suitable reporter genes are well known in the art.

The following examples are offered by way of illustration, and not by way of limitation.

EXAMPLES

Example 1

Enhancement of CD4 T Cell-Based Immunogenicity Against Hsv-2 GD2 Protein when Formulated with the Adjuvant GLA-SE Following Multiple Vaccinations in Mice In this example, the ability of GLA-SE to augment CD4 T cell responses following immunization of mice with a recombinant protein vaccine is assessed.

Figure 2:
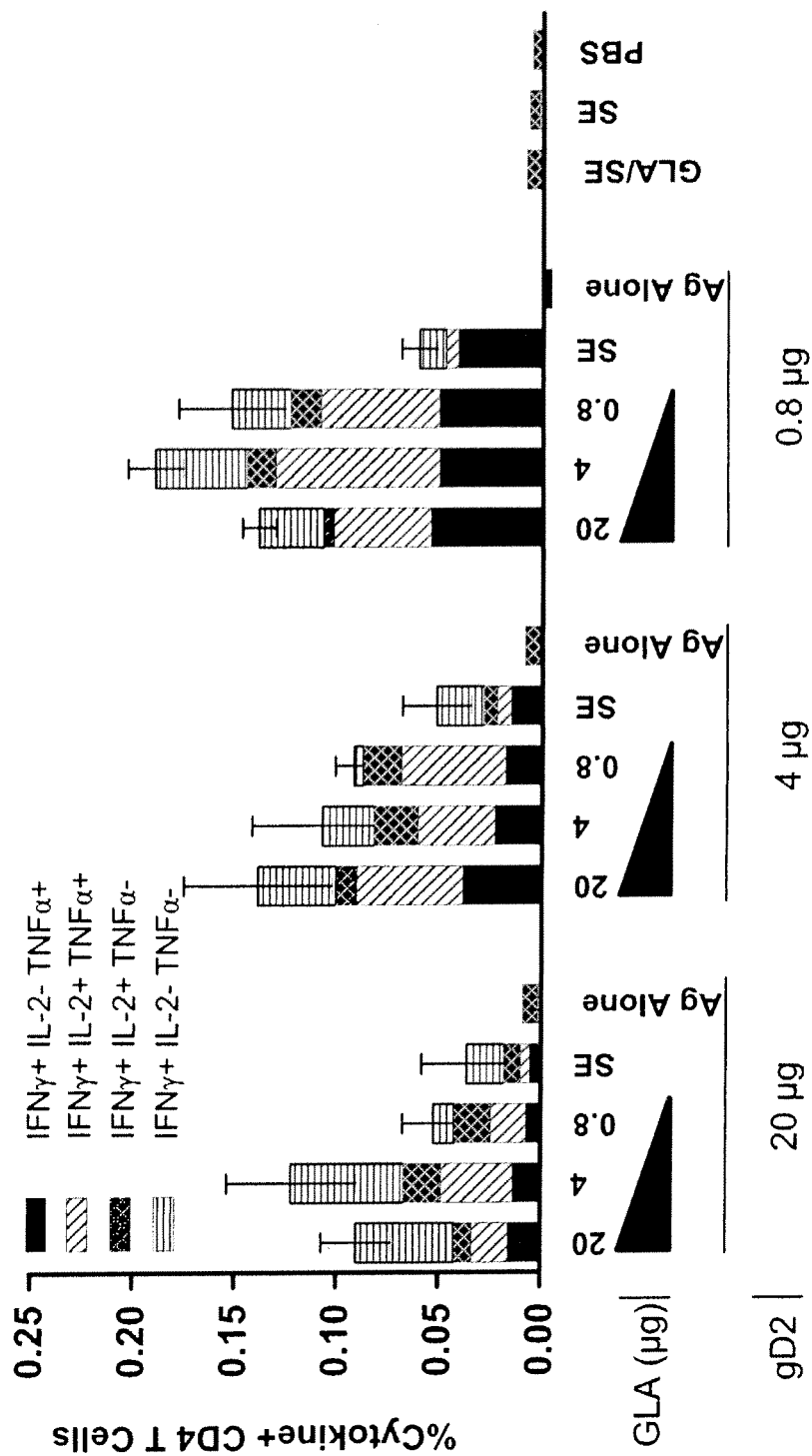
FIG. 2 shows gD2-specific CD4 T cell responses. Data were obtained after Balb/c mice (4/group) were immunized twice i.m. at a 28 day interval with a bivalent vaccine comprised of varying levels of recombinant protein and GLA, as indicated. The graphs are results of flow cytometry analyses for intracellular production of IL-2, TNF-αc, and IFN-γ.

Groups of five Balb/c mice were immunized via a prime/boost immunization regimen (d0 prime/d21 boost) with either 0.8, 4, or 20 µg of recombinant gD protein in combination with either 0.8, 4, or 20 µg of GLA-SE (SE percentage is 2% in this and all following studies), SE alone, or PBS, delivered intramuscularly in 100 µl (50 µl each leg). Mice immunized with GLA-SE, SE alone, or PBS in the absence of recombinant protein served as negative controls. Antigen-specific splenic CD4 T cell responses were measured on day 4 post-boost by Intracellular Cytokine Staining (ICS) for IFN-γ, TNF-α, and IL-2 after ex-vivo re-stimulation of splenocyte cultures for 5 hours with $gD_{272-285}$ peptide, which had previously been identified as a CD4 T cell epitope in gD2 that is presented in mice with the H-2d haplotype. As depicted in FIG. 2, a CD4 T cell response to immunization with each dose of gD2 recombinant protein was observed only when either GLA-SE or SE was included as an adjuvant. At each dose of recombinant gD2 antigen and at each dose of GLA-SE, the magnitude of the gD2-specific CD4 T cell response was increased over the response observed to the same amount of recombinant gD2 antigen formulated with SE alone. In addition, the quality of the responding antigen-specific CD4 T cell population, as measured by the frequency of IFN-γ+, TNF-α+, and IL-2+ CD4 T cells (triple positive) within the responding CD4 T cell population was increased at each dose of recombinant gD2 protein and at each dose of GLA over that observed when gD2 was formulated with SE alone. The data from this study indicate that the formulation of the adjuvant GLA-SE with recombinant HSV-2 protein antigen substantially increases the performance of the vaccine over that which is achieved by immunizing with recombinant protein alone or recombinant protein formulated with SE alone as measured by both the magnitude and quality of the cellular immune response.

Example 2

GLA Augments CD8 T Cell Responses in Mice

In this example, the ability of GLA-SE to augment CD8 T cell responses is assessed following immunization of mice with a recombinant protein vaccine.

Figure 3:
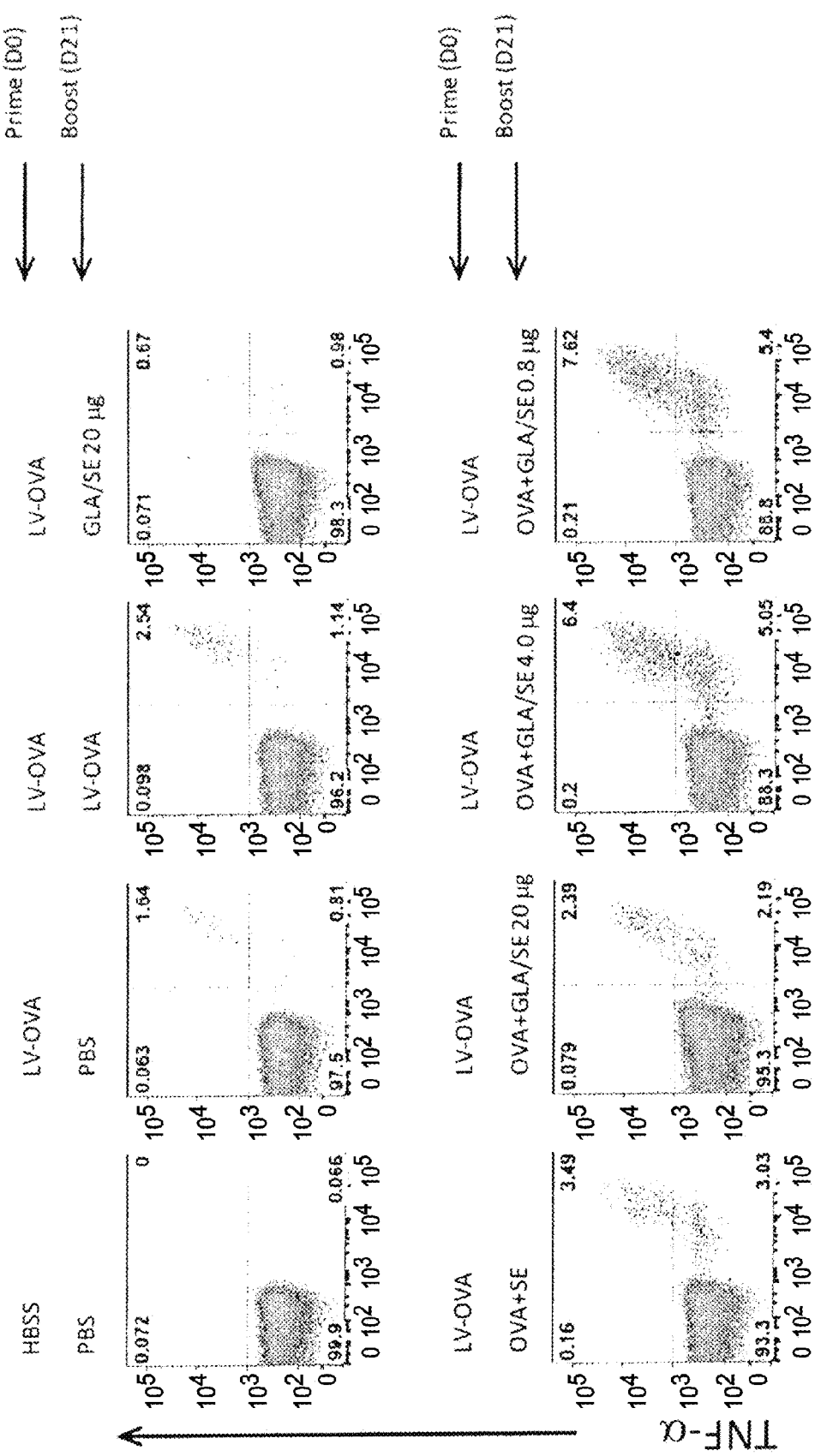
FIG. 3 shows splenic CD8 T cell responses to OVA257 peptide analyzed on D25 post-prime (D4 post-Boost); recombinant OVA=5 µg; SE=2%; lentivirus delivered s.c.; recombinant OVA delivered i.m.
Figure 4:
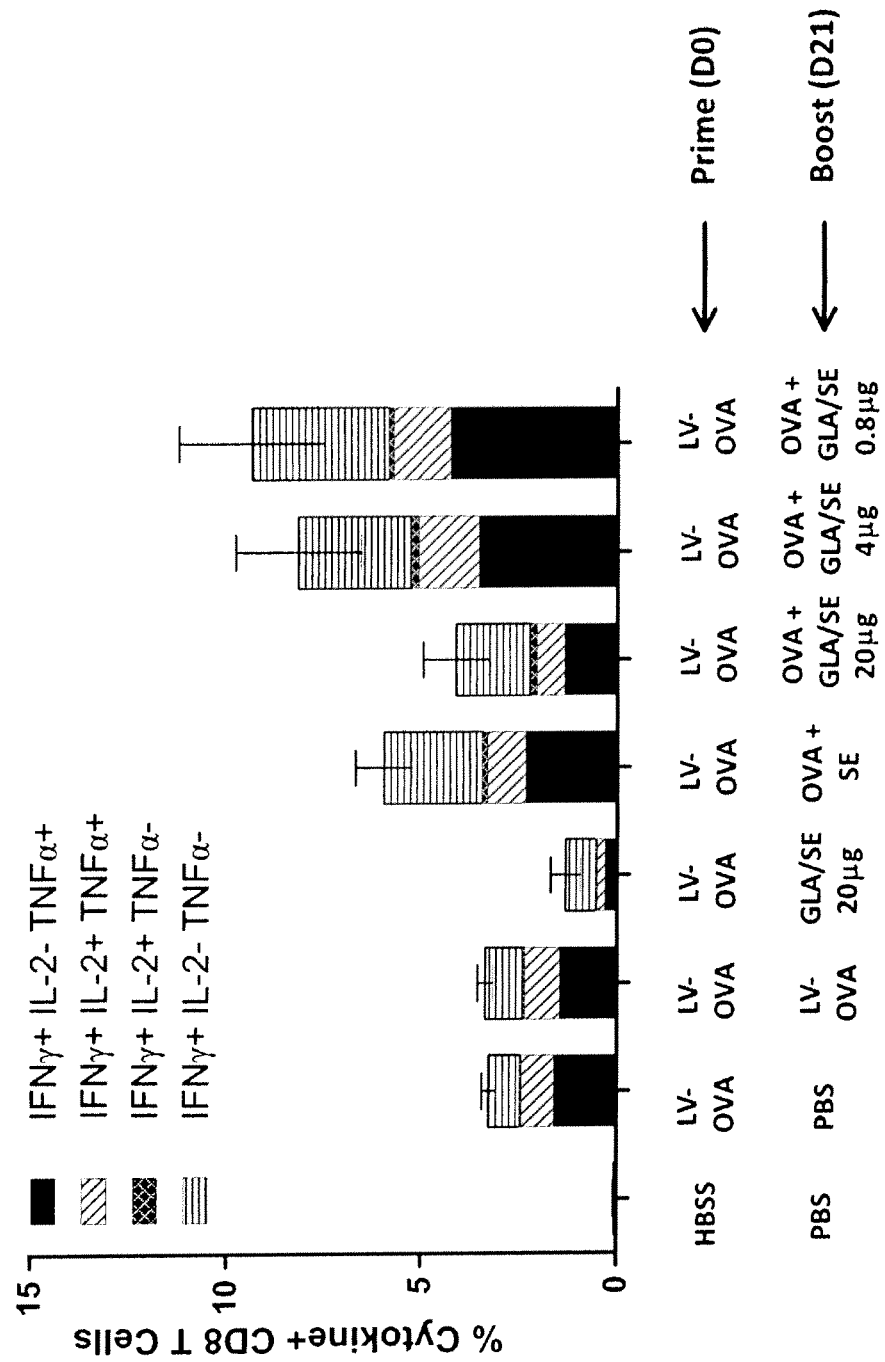
FIG. 4 is a graph showing percent cytokine positive CD8 T cells measured 4 days after a boost. Priming took place on day 0 and boosting on day 21. Column HAL d0 HBSS, d21, PBS; HA2, d0, LV-OVA, d21, PBS; HA3, d0 LV-OVA, d21 LV-OVA; HA4, d0 LV-OVA, d21 20 µg GLA-SE; HA5, d0 LV-OVA, d21 OVA+SE; HA6, d0 LV-OVA, d21 OVA+20 µg GLA-SE; HA7, d0 LV-OVA, d21, 4 µg OVA+GLA-SE; HA8, d0 LV-OVA, d21 OVA+0.8 µg GLA-SE.

Ovalbumin is used as a model protein. Female C57Bl/6 mice were injected s.c. with lentivirus-encoding ovalbumin ("LV-OVA" in FIGS. 3 and 4) and boosted by i.m. injection on day 21 with recombinant ovalbumin adjuvanted with various doses of GLA-SE ("OVA+GLA/SE" in FIGS. 3 and 4). Four days later, splenic T cell responses were measured by intracellular cytokine staining (ICS) to the following in vitro stimulants: OVA MHC Class I peptides 55-62 and 257-264 and MHC Class II peptide 323-339, or antibodies to CD3 and to CD28. CD8 T cells are identified as those secreting any of the cytokines, IFN-γ, IL-2, and TNF-α, As shown in FIG. 3, there was a higher percentage of CD8 T cells in mice that received a boost of antigen, with the highest percentages in mice that received GLA-SE with the antigen in the boost. FIG. 4 provides experimental detail of the ratios of four subsets of CD8 T cells. Therefore, an i.m. vaccine 'boost' with recombinant OVA protein+GLA-SE boosted pre-existing CD8 T cells that had been generated via previous LV vaccination. The mid (4 µg) and low (0.8 µg) doses of GLA provided the highest increase of CD8 T cells under these experimental settings. Therefore, these data show that GLA adjuvanted protein can be used to boost a pre-existing CD8 memory T cell response specific for the protein. Activation of CD8 memory cells is considered to be a desirable property of a therapeutic vaccine against HSV-2 for treatment of infected individuals, underscoring the superior properties GLA adjuvanted protein may confer to an HSV-2 vaccine.

Example 3

Figure 5A:
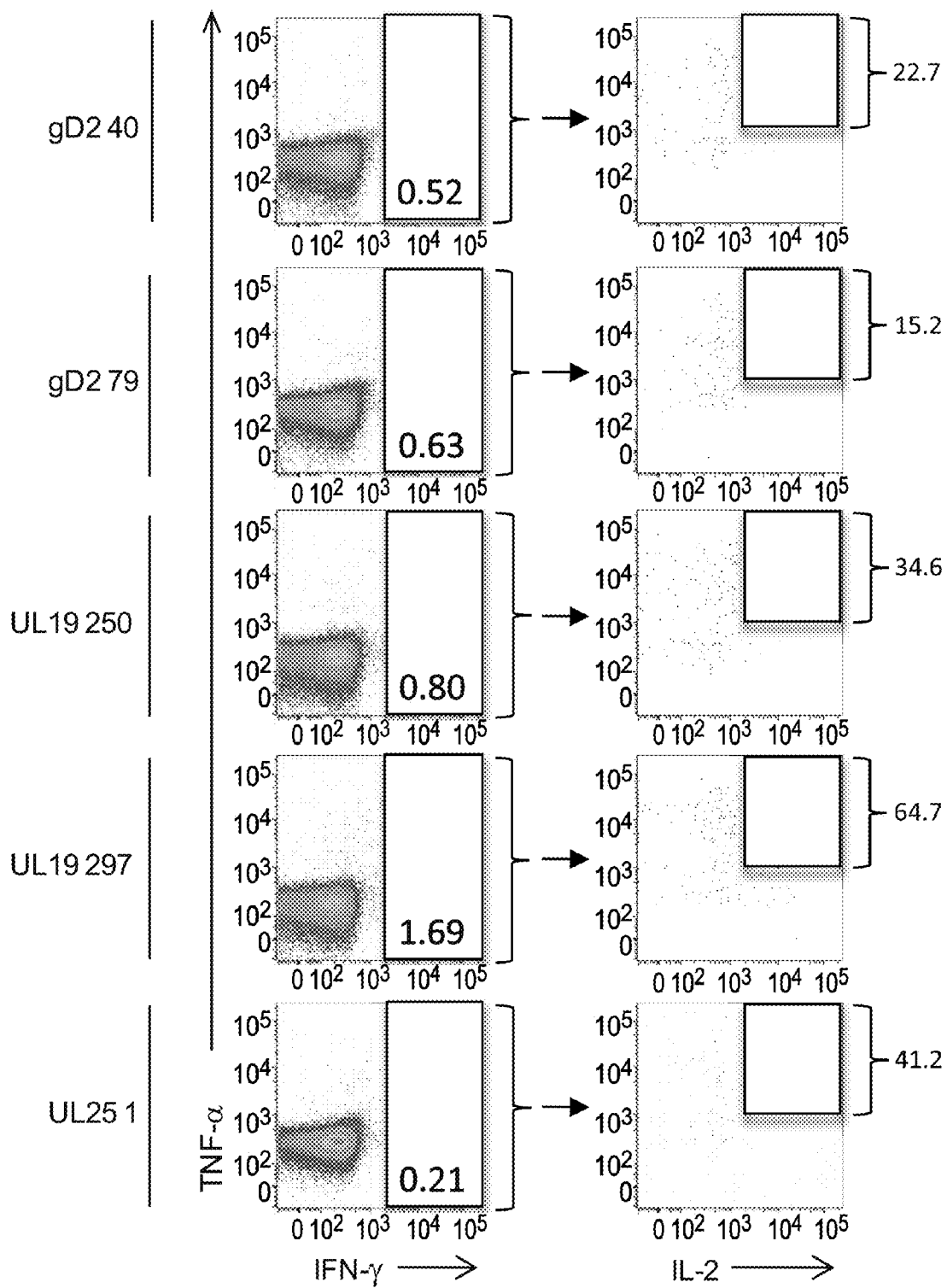
FIGS. 5A-B show data obtained after groups of C57BL/6 mice (5/group) were immunized via a prime/boost immunization regimen (d0 prime/d21 boost) with either 5 µg of recombinant gD, UL19, or UL25 protein in combination with 5 µg of GLA-SE. Splenic CD4 T cell responses were measured on day 4 post-boost by intracellular staining for IFN-γ, TNF-α, and IL-2 after ex vivo re-stimulation with 15-mer peptides previously identified as containing CD4 epitopes for the corresponding recombinant protein immunogen. A) Representative ICS dot plot of the CD4 T cell response to each 15-mer peptide indicated in mice immunized with the corresponding recombinant protein immunogen. B) Percent cytokine positive CD4 T cells are depicted for each group.
Figure 5B:
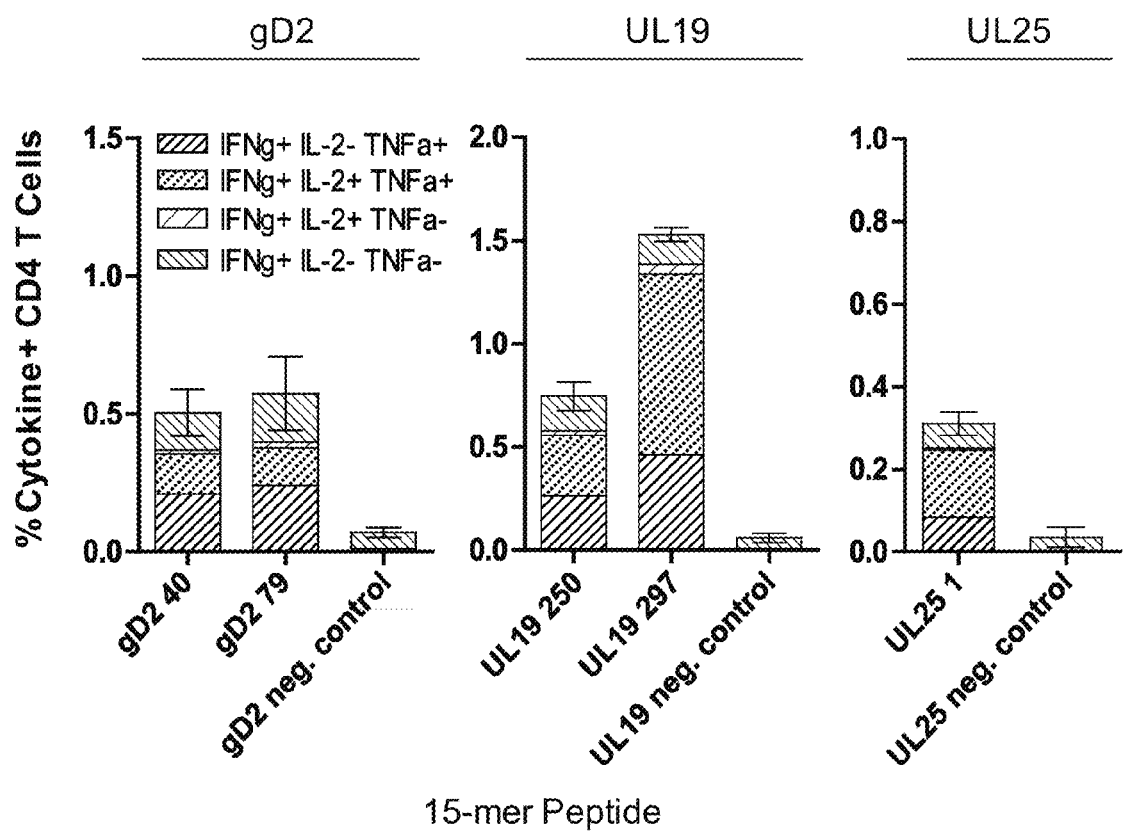

CD4 T Cell-Based Immunogenicity Against Individual HSV-2 GD2, UL19, and UL25 Proteins Following Multiple Vaccinations in Mice The goal of this set of studies was to identify a single mouse strain in which the CD4 T cell-based immunogenicity against each protein subunit in the vaccine could be evaluated. To this end, a series of experiments were conducted in mice to identify individual CD4 T cell epitopes within each HSV-2 antigen (i.e. gD2, UL19, and UL25) within the context of different MHC haplotypes (i.e. BALB/c (H-2$^d$), C57BL/6 (H-2$^b$), and CB6F1 (H-2$^d$+2$^b$)). The experimental strategy consisted of the immunization of naïve mice with 5 μg of each recombinant protein antigen as a monovalent immunogen formulated with 5 μg GLA-SE intramuscularly in 100 μl (50 μl each leg) within the context of a prime/boost immunization regimen (d0 prime/d21 boost). Antigen-specific CD4 T cell responses were analyzed on day 4 post-boost using 15-mer peptide libraries (11 aa overlap between peptides) whose sequence was derived from the corresponding amino acid sequence of the monovalent immunogen. In the primary screens, splenic CD4 cells were analyzed for the production of IFN-γ, TNF-α, and IL-2 in response to the ex vivo simulation of splenocytic cultures with pools of individual 15-mer peptides from the peptide library that corresponded to the individual HSV-2 encoded antigen. Observed CD4 T cell responses in the peptide pools were considered to be positive hits, and secondary (and in some cases tertiary) screens were subsequently conducted with an identical immunization and analysis strategies using either individual peptides within the positive pools from the previous screen as ex vivo stimulates or peptides within the positive pools from the previous screen re-pooled in different combinations. As shown in FIGS. 5A-B, these studies identified individual 15-mer peptides against which an antigen-specific CD4 T cell response could be observed for each of the individual recombinant HSV-2 proteins within the vaccine (i.e. gD2, UL19, and UL25) within the context of the MHC haplotype H-2b (C57BL/6 mice).

Example 4

Figure 6A:
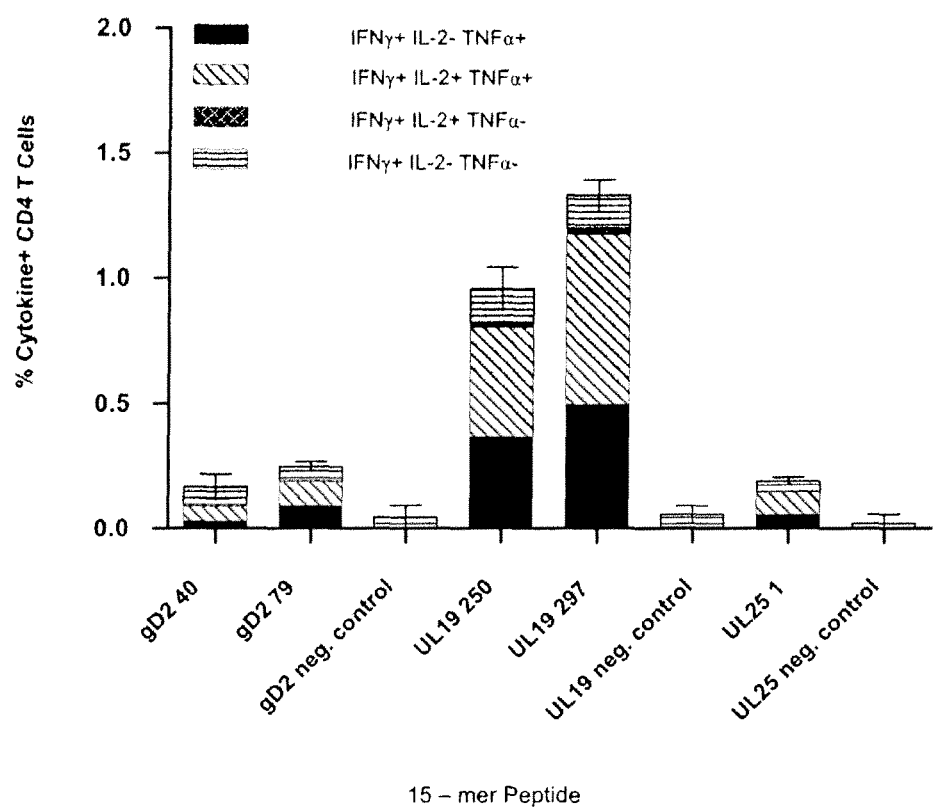
FIGS. 6 A-B show data obtained after a group of five C57BL/6 mice were immunized via a prime/boost regimen (d0 prime/d21 boost) with recombinant gD, UL19, and UL25 proteins delivered in combination and formulated on an equimolar basis (0.8, 3.3, and 1.4 µg of protein, respectively) in combination with 5.5 µg of GLA-SE. Splenic CD4 T cell responses were measured on day 4 post-boost by intracellular staining for IFN-γ, TNF-α, and IL-12 after ex vivo restimulation with 15-mer peptides previously identified as containing CD4 T cell epitopes for each recombinant protein immunogen. An individual peptide which lacks a CD4 T cell epitope from each peptide library was included as a negative control. A) percent cytokine positive CD4 T cells are depicted for each group. B) Serum endpoint titers (defined as the reciprocal of the highest serum dilution that is >2 times background) for antigen-specific antibodies of the IgG1 subclass for each recombinant protein immunogen within the trivalent vaccine.
Figure 6B:
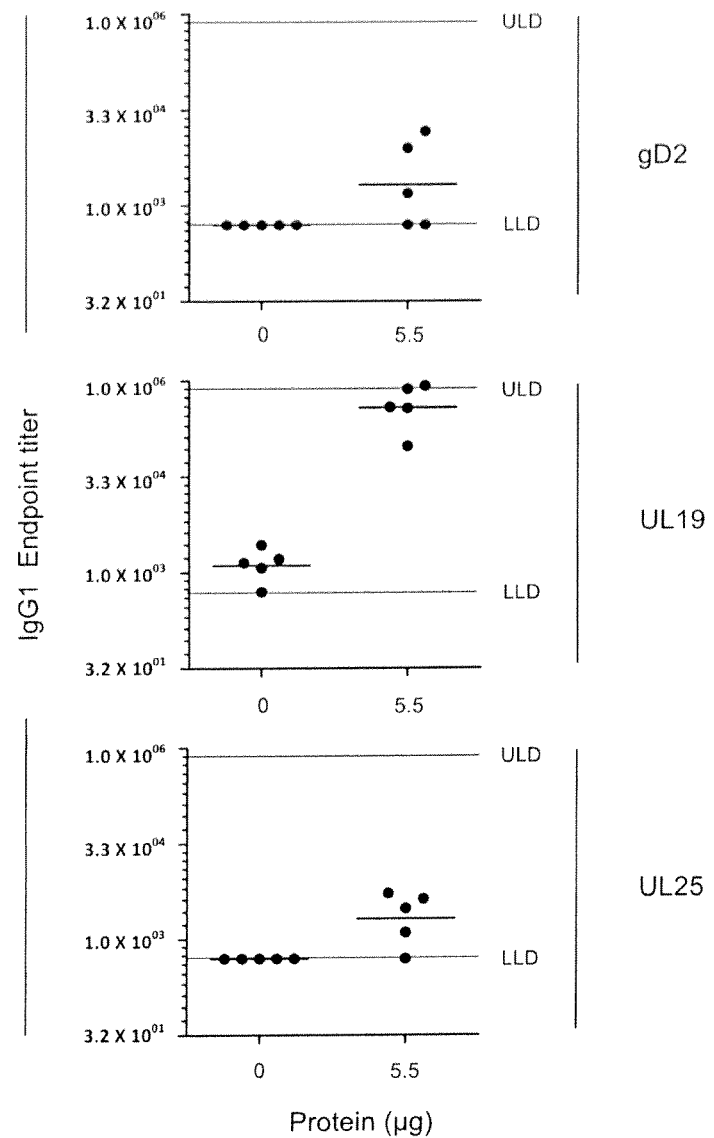

CD4 T and B Cell-Based Immunogenicity Against Each Individual HSV-2 Subunit Protein Following Multiple Vaccinations of a Trivalent Formulation in Mice This example demonstrates the CD4 T cell and B cell-based immunogenicity against each of the individual recombinant protein subunits within the vaccine when they are delivered together as a trivalent formulation with GLA-SE in C57BL/6 mice. The experimental strategy consisted of using two groups of five C57BL/6 mice. One group was immunized via a prime/boost immunization regimen (d0 prime/d21 boost) with recombinant HSV-2 gD2, UL19, and UL25 proteins delivered in combination and formulated on an equi-molar basis (0.8, 3.3, and 1.4 μg of protein, respectively) in combination with 5.5 μg of GLA-SE delivered intramuscularly in 100 μl (50 μl each leg). The second group was mock immunized with vehicle (PBS). The animals were sacrificed on day 4 post-boost for the harvesting of the spleens and peripheral blood (via cardiac puncture). Antigen-specific splenic CD4 T cell responses were measured by ICS for IFNγ, TNFα, and IL-2 after the ex vivo re-stimulation of splenocyte cultures with the 15-mer peptides previously identified as containing CD4 T cell epitopes for each recombinant protein immunogen within the trivalent vaccine (see Example 3). The serum of each vaccinated and mock vaccinated mouse was analyzed for the presence of antigen-specific antibodies of the IgG1 subclass against each of the recombinant protein immunogens within the trivalent vaccine by direct ELISA. As shown in FIGS. 6A-B, antigen-specific CD4 T cell and antibody responses were observed to each of the HSV-2 recombinant protein antigens when delivered together as a trivalent formulation with GLA-SE. These data support the significant immunogenicity of the trivalent vaccine and its ability to elicit a comprehensive immune response (both humoral and cellular) against HSV-2 proteins. Unexpectedly, the magnitude of the immune responses generated were greatest for the UL19 antigen. UL19 has never been included as a component of any of the prior recombinant subunit-based vaccines administered for the treatment or prevention of HSV-2 infection in humans. These data provide evidence that the claimed vaccines display superior properties over the prior art vaccines.

Example 5

Figure 7A:
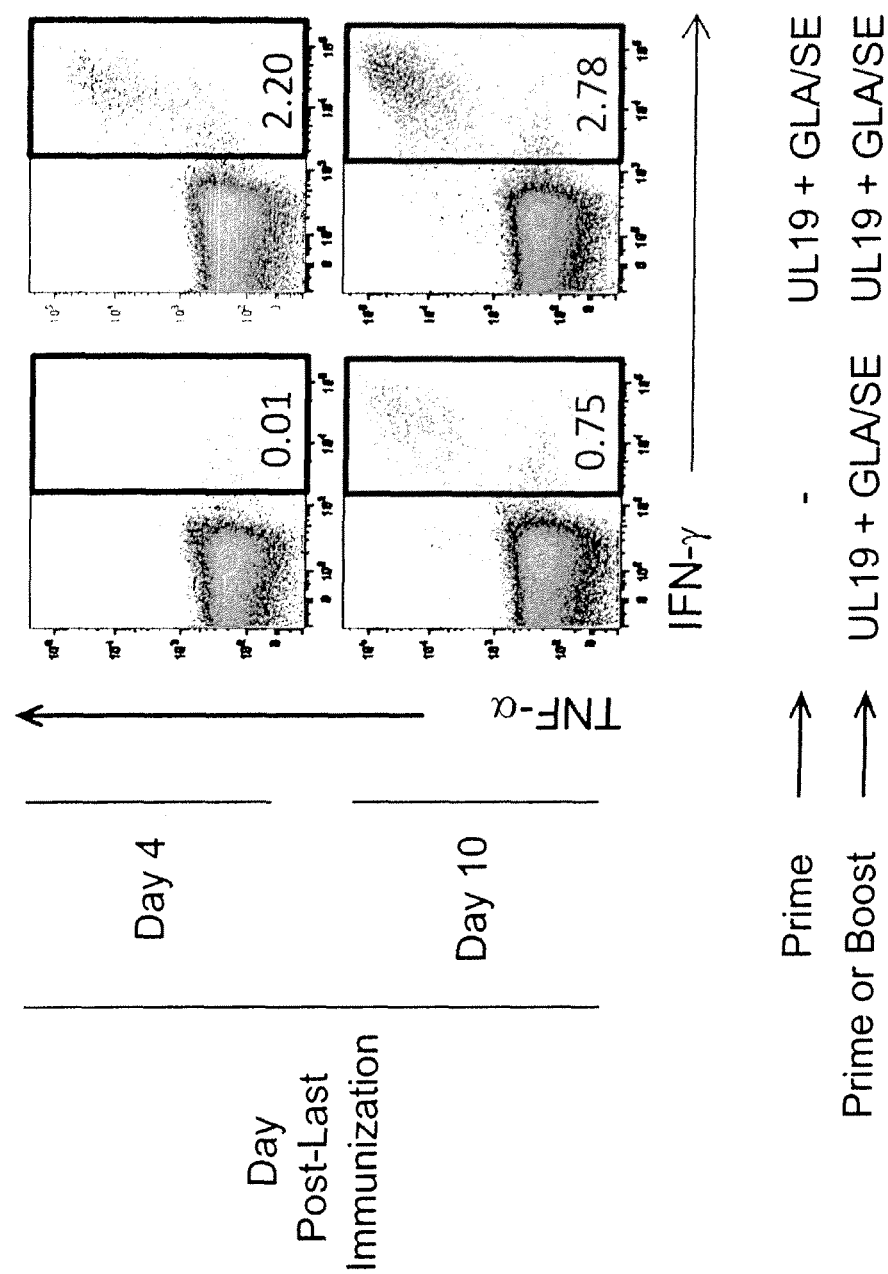
FIGS. 7 A-B show data obtained when groups of C57BL/6 mice (5/group) were immunized via a prime (d0) or prime boost (d0 prime/d21 boost) immunization regimen with 5 µg recombinant UL19 protein delivered in combination with 5 µg of GLA-SE. Splenic CD4 T cell responses were measured on day 4 or day 10 post-last immunization by ICS for IFN-γ, TNF-α, and IL-12 after ex vivo re-stimulation with 15-mer peptides previously identified as containing CD4 T cell epitopes for UL19. A) Representative ICS dot plots of the CD4 T cell response to UL19 15-mer peptide 297 indicated in mice immunized with the corresponding recombinant protein immunogen. Percent cytokine positive DC4 T cells are depicted for each group. B) Percent cytokine positive CD4 T cells responding to UL19 15-mer 250 or 297 are depicted for each group.
Figure 7B:
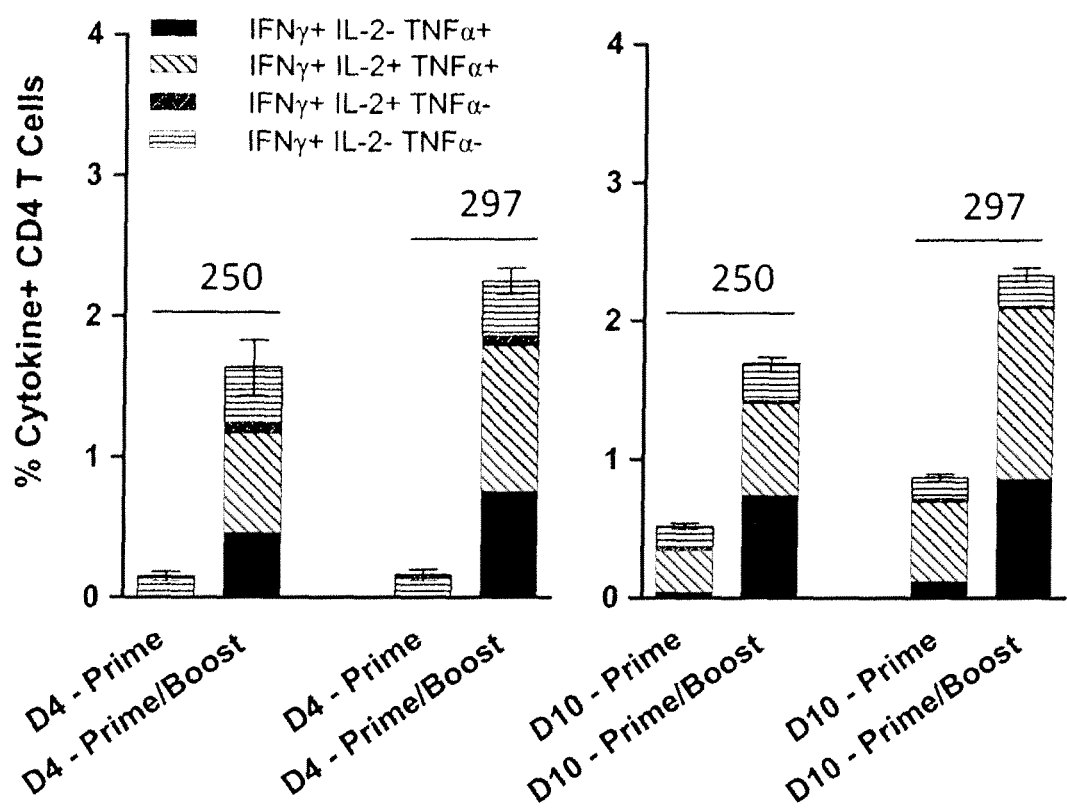
Figure 8A:
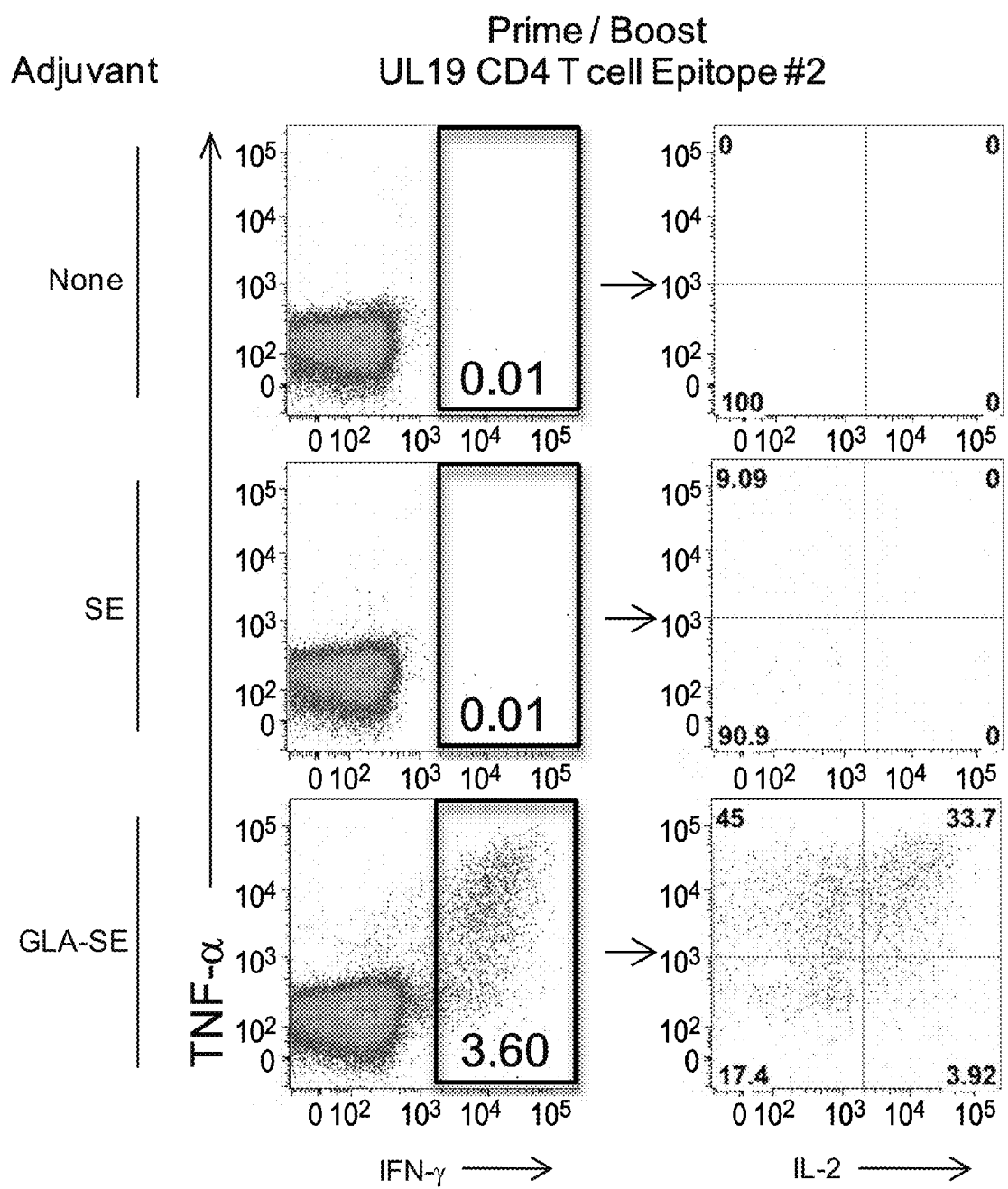
FIGS. 8A-B show data obtained when groups of C57BL/6 mice (5/group) were immunized via a prime (d0) or prime boost (d0 prime/d21 boost) immunization regimen with 5 µg recombinant UL19 protein delivered alone or in combination with 5 µg of SE or GLA-SE. Splenic CD4 T cell responses were measured on day 5 or day 10 post-last immunization by ICS for IFN-γ, TNF-α, and IL-12 after ex vivo re-stimulation with 15-mer peptides previously identified as containing CD4 T cell epitopes for UL19. A) Representative ICS dot plots of the CD4 T cell response to UL19 15-mer peptide 297 indicated in mice immunized with the corresponding recombinant protein immunogen. Percent cytokine positive CD4 T cells are depicted for each group. B) Percent cytokine positive CD4 T cells responding to UL19 15-mer 250 or 297 are depicted for each group.
Figure 8B:
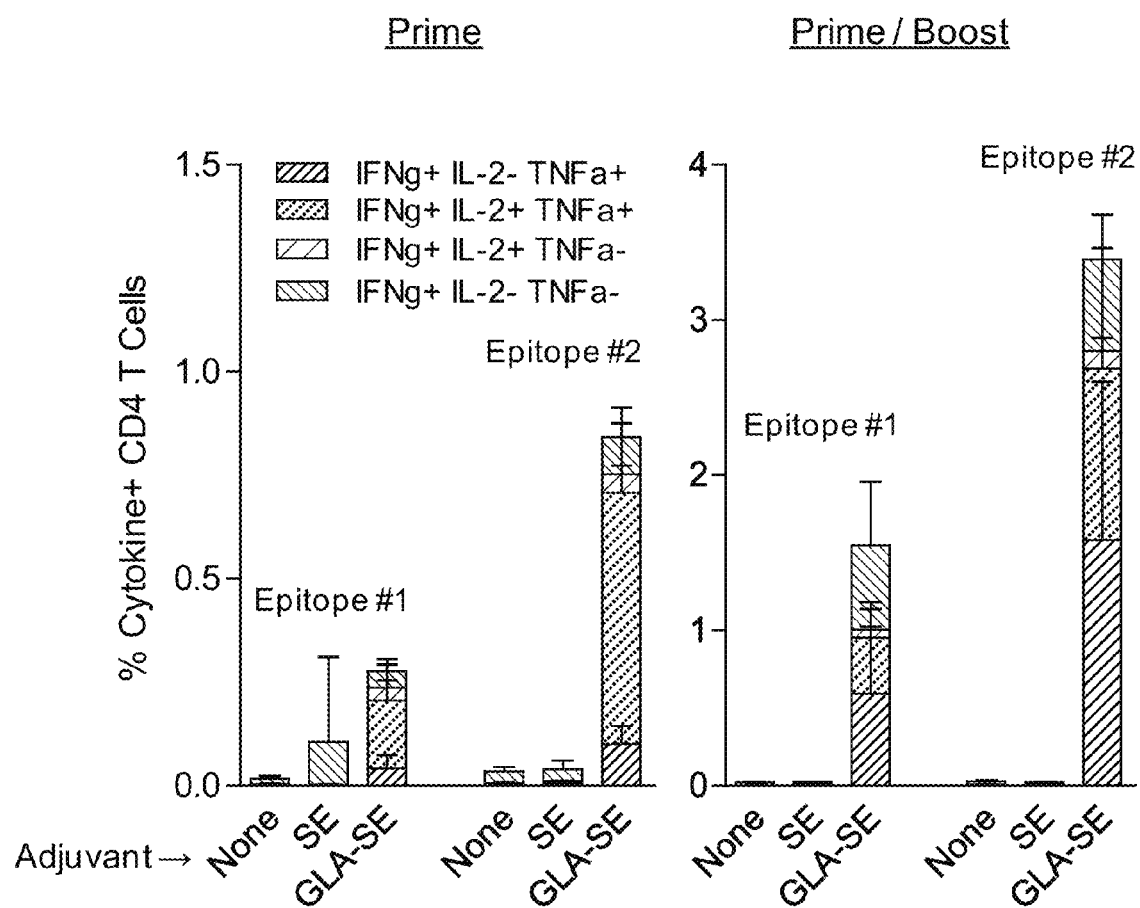

Antigen-Specific CD4 T Cell Responses Following Single and Multiple Immunizations of HSV-2 UL19 with GLA-SE in Mice This Example shows the CD4 T cell-based immunogenicity generated by single and repeat immunizations of HSV-2 UL19 formulated with GLA-SE in mice. For this study, two groups of five C57BL/6 mice received one immunization and two groups of five c57BL/6 mice received two immunizations (separated by 21 days) with 5 μg of recombinant UL19 protein antigen as a monovalent immunogen with 5 μg GLA-SE. The groups of mice were sacrificed at either day 4 or 10 after the final immunization for the analysis of antigen-specific CD4 T cell responses. The immunizations that the respective analysis groups received were staggered in time such that all four groups of mice were sacrificed on the same day for the analysis of the antigen-specific CD4 T cell response. The antigen-specific CD4 T cell response to the immunogen was measured by the production of IFN-γ, TNF-α, and IL-2 in response to the ex vivo stimulation of splenocytes with the individual UL19 15-mer peptides numbers 250 and 297 that had been previously identified as containing CD4 T cell epitopes specific for UL19 (see Example 3). As depicted in FIGS. 7A-B, at day four post-last immunization UL19-specific CD4 T cell responses were only detected in animals that received two immunizations, whereas UL19-specific CD4 T cell responses were detected at day 10 post-last immunization within both the prime and the prime/boost arms of the experiment. At day 10 post-last immunization, the magnitude of the response was markedly increased (~2.5 fold) in the animals that received two immunizations as compared to those that received only a single immunization. These findings show that repeat administration of a vaccine containing a recombinant HSV-2 protein+GLA-SE is a superior protocol for increasing the response and the magnitude of the ensuing antigen-specific CD4 T cell response To test the dependence of the increase in the CD4 T cell response following repeat administration of the vaccine on GLA-SE, a similar experiment was performed in which groups of mice were immunized with UL19 protein alone or protein formulated with SE alone, or GLA-SE. The groups of mice were sacrificed at either day 5 or 10 post final immunization for the analysis of antigen-specific CD4 T cell responses. The antigen-specific CD4 T cell response to the immunogen was measured by the production of IFN-γ, TNF-α, and IL-2 in response to the ex vivo stimulation of splenocytes with the individual UL19 15-mer peptides numbers 250 and 297 that had been previously identified as containing CD4 T cell epitopes specific for UL19 (see Example 3). As depicted in FIGS. 8A-B, animals that received two immunizations as compared to those that received only a single immunization displayed a significant increase in the antigen-specific CD4 T cell response, confirming the results of the previous experiment. Importantly, this increase was found to be dependent upon the GLA-SE adjuvant as mice receiving two immunizations displayed no significant CD4 T cell responses when the immunogen was administered alone or with SE in the absence of GLA.

Example 6

Figures 9A, 9B, 9C:
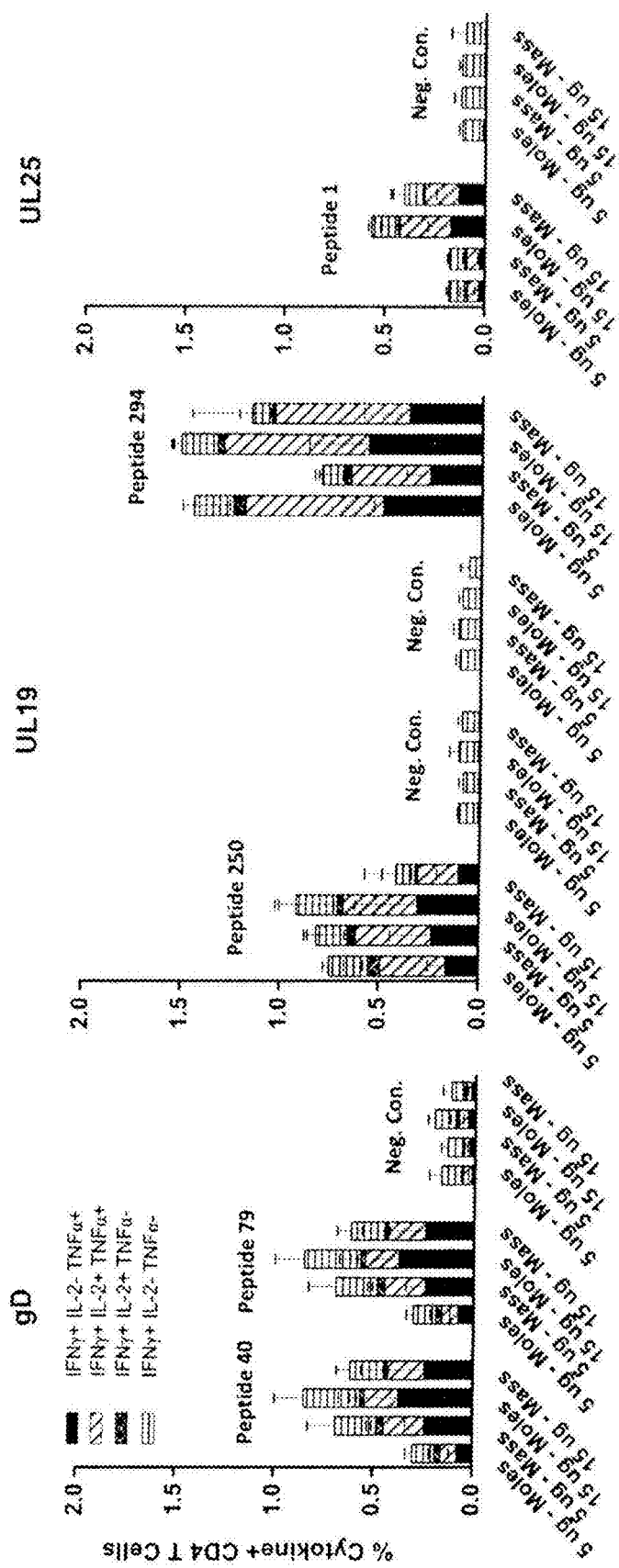
FIGS. 9A-C show data obtained when groups of C57BL/6 mice (5/group) were immunized via a prime boost (d0 prime/d21 boost) immunization regimen with recombinant proteins formulated on either an equimolar or an equimass basis. Total protein delivered was either 5 µg or 15 µg. Splenic CD4 T cell responses were measured on day 5 post-last immunization by intracellular staining for IFN-γ, TNF-α, and IL-12 after ex vivo re-stimulation with 15-mer peptides previously identified as containing CD4 T cell epitopes. A) Percent cytokine positive CD4 T cells responding to gD peptides are depicted. B) Percent cytokine positive CD4 T cells responding to UL19 peptides are depicted. C) Percent cytokine positive CD4 T cells responding to UL25 peptides are depicted.

Antigen-Specific CD4 T Cell Responses Following Immunization with Trivalent HSV Vaccine Formulated with GLA-SE in Mice This Example shows that CD4 T cell responses can be generated against each subunit of a trivalent subunit vaccine comprising the gD2, UL19, and UL25 antigens formulated in GLA-SE when the recombinant proteins are formulated on an equi-molar as well as an equi-mass basis. Groups of female C57BL/6 mice (5 mice/group) were immunized with a trivalent vaccine wherein the total protein was either 5 μg or 15 μg on either an equi-molar or an equi-mass basis. Mice received a second immunization with a homologous formulation at day 21 and T cell responses were measured after ex vivo restimulation with an appropriate peptide by ICS five days following the last immunization. As shown in FIG. 9, epitope-specific CD4 T cell responses are generated against each individual component of the trivalent HSV-2 subunit vaccine. Positive responses were observed despite whether the recombinant protein components are formulated on an equi-molar or an equi-mass basis, indicating that the responses are not significantly impacted or altered based on relative protein composition of the vaccine.

Example 7

Mouse and Guinea Pig Challenge Models

Protective efficacy of a vaccine is demonstrated in mice by prevention of death and reduction of viral load following challenge with virulent HSV-2 virus. Groups of ten six to eight week old female Balb/c mice receive three intramuscular injections of vaccine at 0, 2, and 4 weeks, followed by viral challenge at 6 weeks using 50 times the $LD_{50}$ (307pfu) of HSV-2 virus administered by vaginal inoculation. Following challenge, mice are inspected twice daily, assessed for clinical score, and euthanized if pre-morbid. On days 1, 3, and 5 after challenge, vaginal swabs are taken for measurement of viral load by quantitative real-time PCR analysis of HSV-2 DNA. Sera are collected prior to each vaccination, prior to viral challenge, and on day 14 following challenge in surviving animals. Neutralizing antibody titers and the ratio of antigen-specific IgG1/IgG2a titers are measured to correlate these responses with survival and vaginal DNA titers. Splenocytes from day 14 survivors are isolated for studies of T cell responses. Negative control groups, receiving injections lacking protein and adjuvant or injected with adjuvant alone, typically die within two weeks following viral challenge, while positive control groups, receiving the attenuated live HSV-2 vaccine typically survive viral challenge.

Therapeutic efficacy is demonstrated in HSV-2 infected guinea pigs as detected by a reduction in lesions and vaginal HSV-2 shedding following recovery from primary HSV-2 infection. Female Hartley guinea pigs are infected by rupturing the vaginal closure membrane with a calcium alginate-tipped swab followed by instillation of $1 \times 10^{5.7}$ pfu HSV-2 strain MS by plastic catheter. The animals are evaluated daily and the severity of the primary genital skin disease is quantified using an established lesion score-scale. Following resolution of the primary genital skin disease, animals (12/group) that experience clinically symptomatic infection are randomized to three groups that include the vaccine candidate (Group 1), the corresponding adjuvant minus antigen (Group 2), and vehicle control treated animals (Group 3). Beginning on day 15 after HSV-2 infection, all animals are examined daily for the presence of recurrent viral lesions on the perineum. In addition, daily vaginal swab samples are collected from all animals and stored frozen (−80° C.) for DNA extraction and quantitative PCR analysis of viral DNA. On day 21 after HSV-2 infection, animals in Groups 1 and 2 are immunized by bilateral intramuscular injection in the rear legs. The animals receive a second immunization on day 42 post challenge. Daily swabbing and scoring continue until day 63 post challenge. The primary endpoints are the impact of immunization on the frequency of symptomatic recurrent lesions and on the frequency and magnitude of virus shedding into the genital tract. This is be measured as the percentage of days that animals are positive for HSV-2 DNA by PCR ("shedding rate") and the quantity of HSV-2 DNA shed, expressed as a cumulative copy number during the observation period.

Example 8

Safety and Immunogenicity of Vaccine in Humans

The safety and immunogenicity of gD2, UL19 and UL25 antigens formulated with GLA-SE, or SE alone may be tested in a Phase 1A/1B study design using HSV-2 seronegative subjects (target for prophylactic vaccine) and HSV-2 seropositive subjects (target for immunotherapeutic vaccine). The study design may follow that established by the HIV Vaccine Trials Network (HVTN), and has been used in 40 human HIV-1 phase IA vaccine trials in the last 10 years.

The design of these Phase 1A trials can consist of a standardized format of 12 subjects per group (10 vaccine-2 placebo) and be based upon the ability to define a serious adverse event at a 15% prevalence. Vaccines that are not immunogenic (<2 of 10 subjects develop immunity) can also be defined. In the HSV-2 Phase 1A study, subjects may receive 3 i.m. immunizations of 1 μg or 2.5 μg GLA-SE at 4 week intervals. A total of 48 HSV seronegative and HSV-2 seropositive subjects (HSV-1 seropositive or HSV-1 seronegative) may be immunized in the Phase 1A trial.

HSV-2 seronegative subjects may be defined by Western Blot at Day 0. In addition to safety assessments, subjects on study may be monitored for a possible vaccine-induced HSV-2 specific immune humoral and cellular immune response, and frequency of recurrence of genital ulcers (HSV-2 seropositive subjects only). For the HSV-2 infected population, two pre-vaccination time points may be used to establish T cell levels to gD2, UL19, and UL25 antigens and antibody to gD2. Cellular immunity to HSV-2 recombinant proteins may be assessed by IFN-γ ELISPOT and ICS assays, and gD2-specific humoral immunity by ELISA and neutralizing antibody assays.

Example 9

Enhancement of Antibody-Based Immunogenicity Against HSV-2 GD2 Protein when Formulated with the Adjuvant GLA-SE Following Multiple Vaccinations in Mice In this example, the ability of GLA-SE to augment CD4 T cell responses following immunization of mice with a recombinant protein vaccine is assessed.

Figure 10:
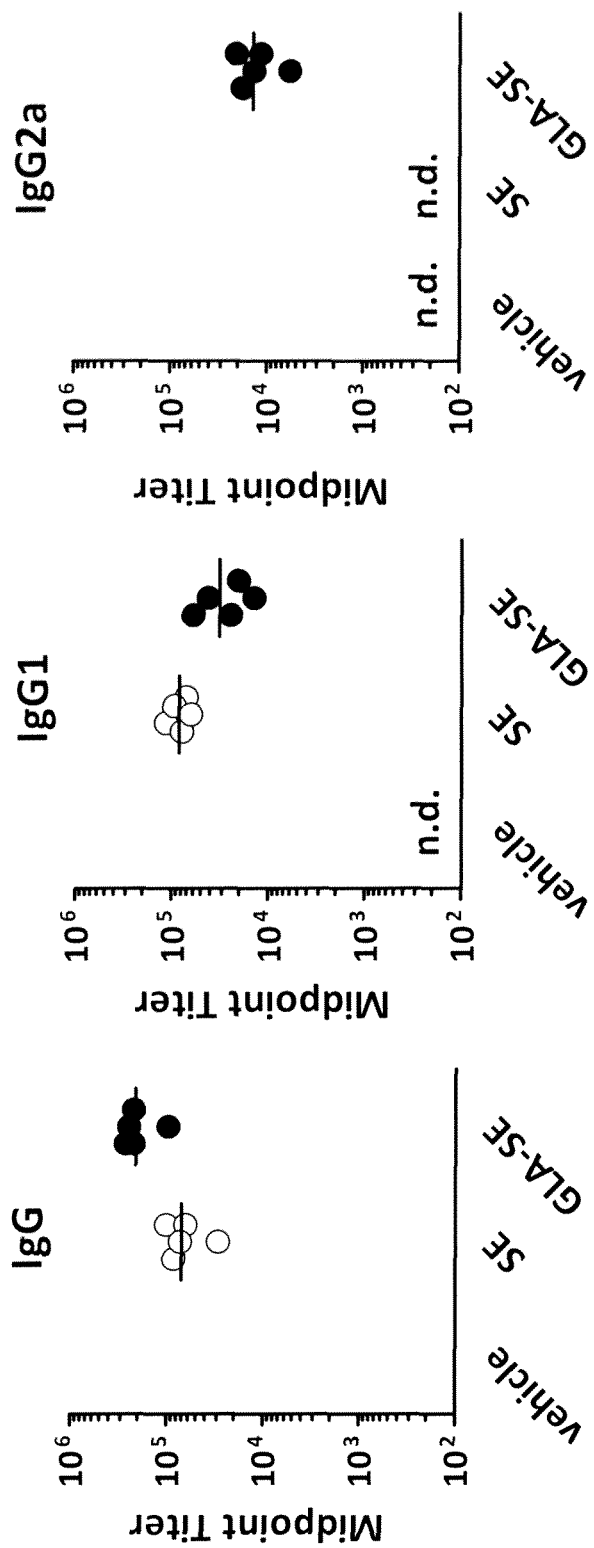
FIG. 10 shows data obtained when groups of BALB/c mice (5/group) were immunized via a prime/boost immunization regimen (d0 prime/d21 boost) with 4 µg of recombinant gD protein in combination with either 4 µg of GLA-SE, SE alone, or PBS vehicle, delivered intramuscularly in 100 µl (50 µl per leg). HSV-2 gD2-specific antibodies of the IgG, IgG1, and IgG2a isotypes were measured by ELISA.

Groups of five Balb/c mice were immunized via a prime/boost immunization regimen (d0 prime/d21 boost) with 4 μg of recombinant gD protein in combination with either 4 μg of GLA-SE, SE alone, or PBS vehicle, delivered intramuscularly in 100 μl (50 μl per leg). HSV-2 gD2-specific antibodies of the IgG, IgG1, and IgG2a isotypes were measured by ELISA. As depicted in FIG. 10, GLA-SE adjuvant enhanced the total IgG response against HSV-2 gD2, reduced the production of antigen-specific IgG1, and increased the production of antigen-specific IgG2a.

Example 10

Enhancement of CD8 T Cell-Based Immunogenicity Against HSV-2 UL19UD Protein when Formulated with the Adjuvant GLA-SE In this example, the ability of GLA-SE to induce functional HSV-2 UL19-specific CD8 T cell responses following immunization of mice with a trivalent vaccine containing recombinant HSV-2 gD2, UL19 upper domain (UL19ud), and UL25 is assessed.

Figure 11:
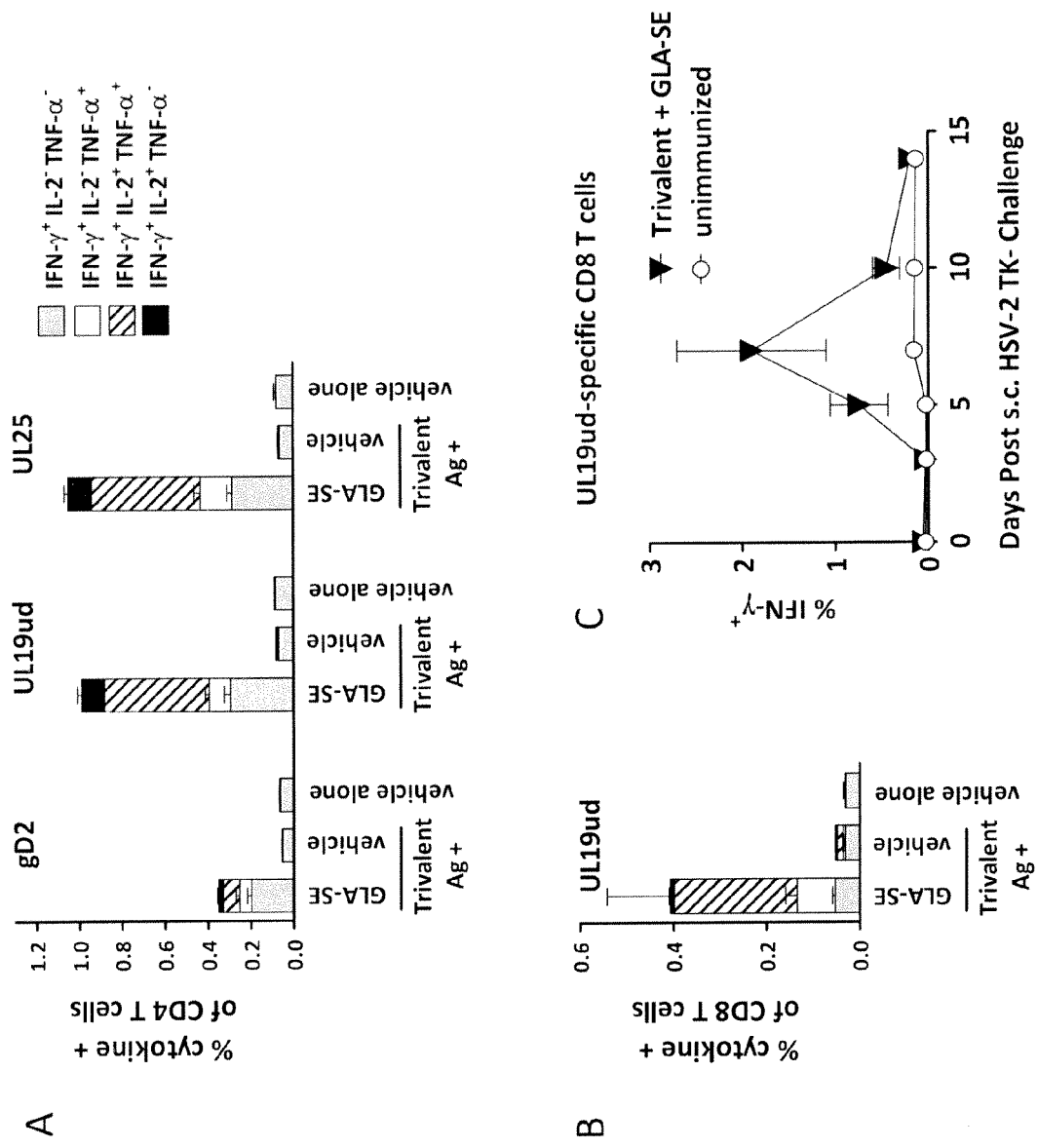
FIG. 11 shows data obtained when groups of five C57BL/6 mice were given a single intramuscular immunization of trivalent vaccine consisting of 5 µg each of recombinant gD2, UL19ud, and UL25 in combination with 5 µg GLA-SE or control vaccine articles. Antigen-specific splenic CD4 and CD8 T cell responses were measured on day 6 post-immunization by Intracellular Cytokine Staining (ICS) for IFN-γ, TNF-α, and IL-2 after ex-vivo re-stimulation of splenocyte cultures for 5 hours with gD2, UL19, or UL25 peptides. A) Frequency and cytokine phenotype of CD4 T cells responding to peptides from gD2, UL19ud, or UL25. B) Frequency and cytokine phenotype of CD8 T cells responding to UL19 peptides. C) Frequency of CD8 T cells responding to UL19 peptides in mice that were immunized 4 weeks earlier with trivalent vaccine with GLA-SE and challenged subcutaneously with attenuated HSV-2 thymidine kinase-deficient (TK−) virus.

Groups of five C57BL/6 mice were given a single intramuscular immunization of trivalent vaccine consisting of 5 μg each of recombinant gD2, UL19ud, and UL25 in combination with either 5 μg GLA-SE or 5% dextrose vehicle. Mice immunized with vehicle alone served as negative controls. Antigen-specific splenic CD4 and CD8 T cell responses were measured on day 6 post-immunization by Intracellular Cytokine Staining (ICS) for IFN-γ, TNF-α, and IL-2 after ex-vivo re-stimulation of splenocyte cultures for 5 hours with gD2, UL19, or UL25 peptides. As depicted in FIG. 11, panel A, a CD4 T cell response to each component of the trivalent vaccine (gD2, UL19ud, and UL25) was observed when GLA-SE was included as an adjuvant. Notably, as depicted in FIG. 11, panel B, a CD8 T cell response was observed against the UL19ud antigen when given with GLA-SE. Confirming that these CD8 T cells are functional, mice that were unimmunized or immunized 4 weeks earlier with trivalent vaccine with GLA-SE were challenged subcutaneously with attenuated HSV-2 thymidine kinase-deficient (TK−) virus and UL19-specific CD8 T cell responses were measured by ICS. As depicted in FIG. 11, panel C, the magnitude of the CD8 T cell response upon viral challenge was greater in mice previously immunized with vaccine.

Example 11

Enhancement of Prophylactic Antiviral Efficacy of Recombinant Hsv-2 Protein Vaccine when Formulated with the Adjuvant GLA-SE In this example, the ability of GLA-SE to enhance the ability of a bivalent recombinant HSV-2 protein vaccine to protect against lethal HSV-2 challenge is assessed.

Figure 12:
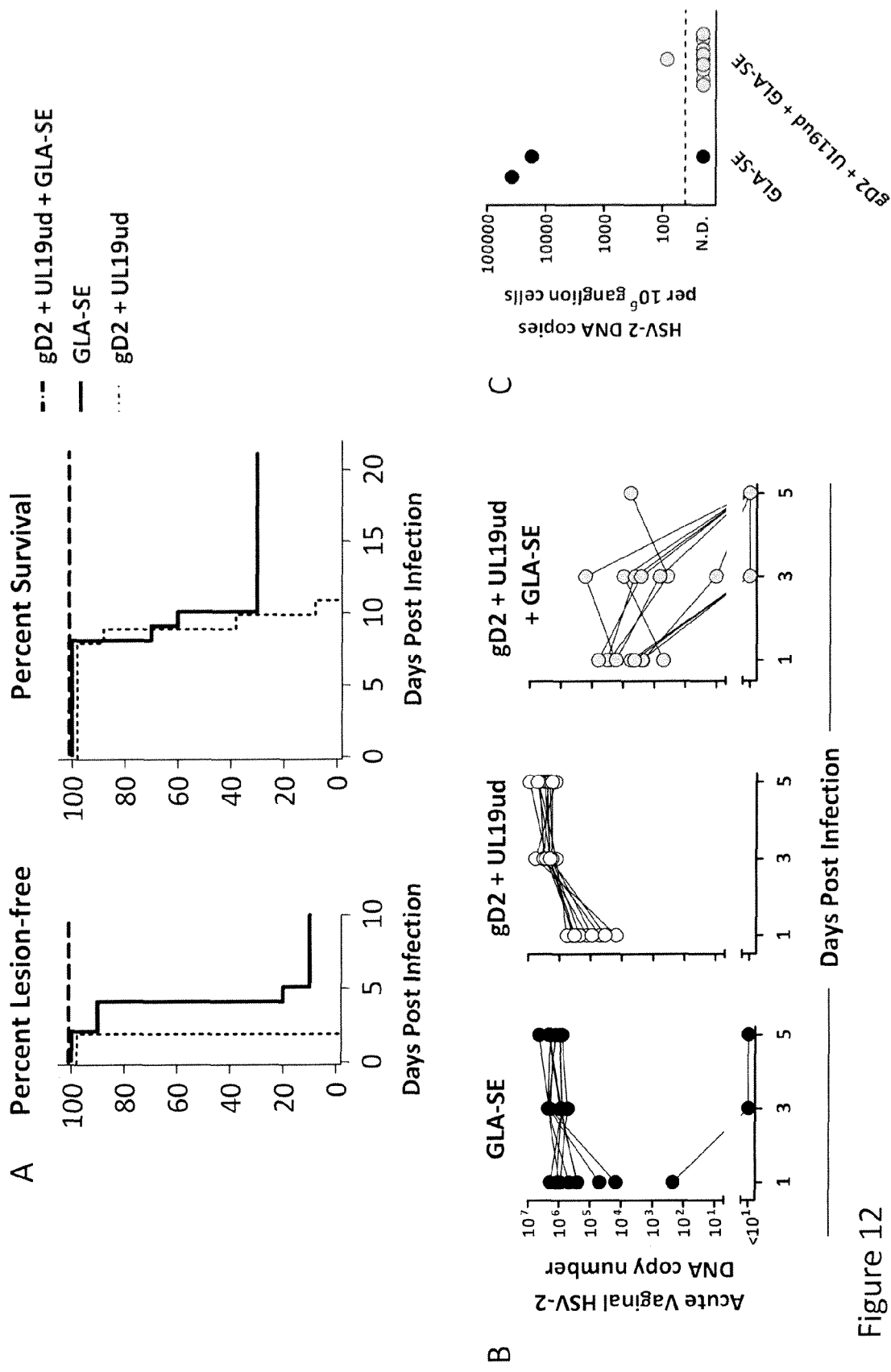
FIG. 12 shows data obtained when groups of ten C57BL/6 mice were given two intramuscular immunizations, separated by 28 days, of bivalent vaccine consisting of 5 µg each of recombinant gD2 and UL19ud in combination with either 5 µg GLA-SE or 5% dextrose vehicle. Mice immunized with 5 µg GLA-SE alone served as negative controls. 22 days after the second immunization, mice were treated with depot medroxyprogesterone acetate and then challenged six days later with a $50xLD_{50}$ dose of wild-type HSV-2 intravaginally. Mice monitored daily for formation of genital lesions and survival. On days 1, 3, and 5 post infection, vaginal swabs were collected for quantitation of HSV-2 DNA by PCR. Approximately 2 months post infection, the dorsal root ganglia were harvested from surviving mice and latent HSV-2 DNA was quantified by PCR. As depicted in FIG. 12, panel A, mice immunized with gD2 and UL19ud with GLA-SE has dramatically reduced lesion formation and increased survival compared to mice immunized with either gD2 and UL19ud alone or GLA-SE alone. Likewise, as depicted in FIG. 12, panel B, 9 out of 10 mice immunized with gD2 and UL19ud with GLA-SE had no detectable HSV-2 DNA by day 5, whereas mice in either control group showed sustained levels of HSV-2 in the vagina through day 5. As depicted in FIG. 12, panel C, though there were three survivors in the GLA-SE only group, 2 out of 3 of these mice showed significant levels of latent HSV-2 in the dorsal root ganglia, mice immunized with gD2 and UL19ud with GLA-SE showed little to no detectable HSV-2 in the ganglia.

Groups of ten C57BL/6 mice were given two intramuscular immunizations, separated by 28 days, of bivalent vaccine consisting of 5 μg each of recombinant gD2 and UL19ud in combination with either 5 μg GLA-SE or 5% dextrose vehicle. Mice immunized with 514 GLA-SE alone served as negative controls. 22 days after the second immunization, mice were treated with depot medroxyprogesterone acetate and then challenged six days later with a $50xLD_{50}$ dose of wild-type HSV-2 intravaginally. Mice monitored daily for formation of genital lesions and survival. On days 1, 3, and 5 post infection, vaginal swabs were collected for quantitation of HSV-2 DNA by PCR. Approximately 2 months post infection, the dorsal root ganglia were harvested from surviving mice and latent HSV-2 DNA was quantified by PCR. As depicted in FIG. 12, panel A, mice immunized with gD2 and UL19ud with GLA-SE has dramatically reduced lesion formation and increased survival compared to mice immunized with either gD2 and UL19ud alone or GLA-SE alone. Likewise, as depicted in FIG. 12, panel B, 9 out of 10 mice immunized with gD2 and UL19ud with GLA-SE had no detectable HSV-2 DNA by day 5, whereas mice in either control group showed sustained levels of HSV-2 in the vagina through day 5. As depicted in FIG. 12, panel C, though there were three survivors in the GLA-SE only group, 2 out of 3 of these mice showed significant levels of latent HSV-2 in the dorsal root ganglia, mice immunized with gD2 and UL19ud with GLA-SE showed little to no detectable HSV-2 in the ganglia.

Example 12

Enhancement of Expansion of Pre-Existing Memory CD8 T Cells by Recombinant HSV-2 Protein Vaccine when Formulated with the Adjuvant GLA-SE In this example, the ability of GLA-SE to enhance the ability of a trivalent recombinant HSV-2 protein vaccine to expand memory CD8 T cells previously induced by HSV-2 infection is assessed.

Figure 13:
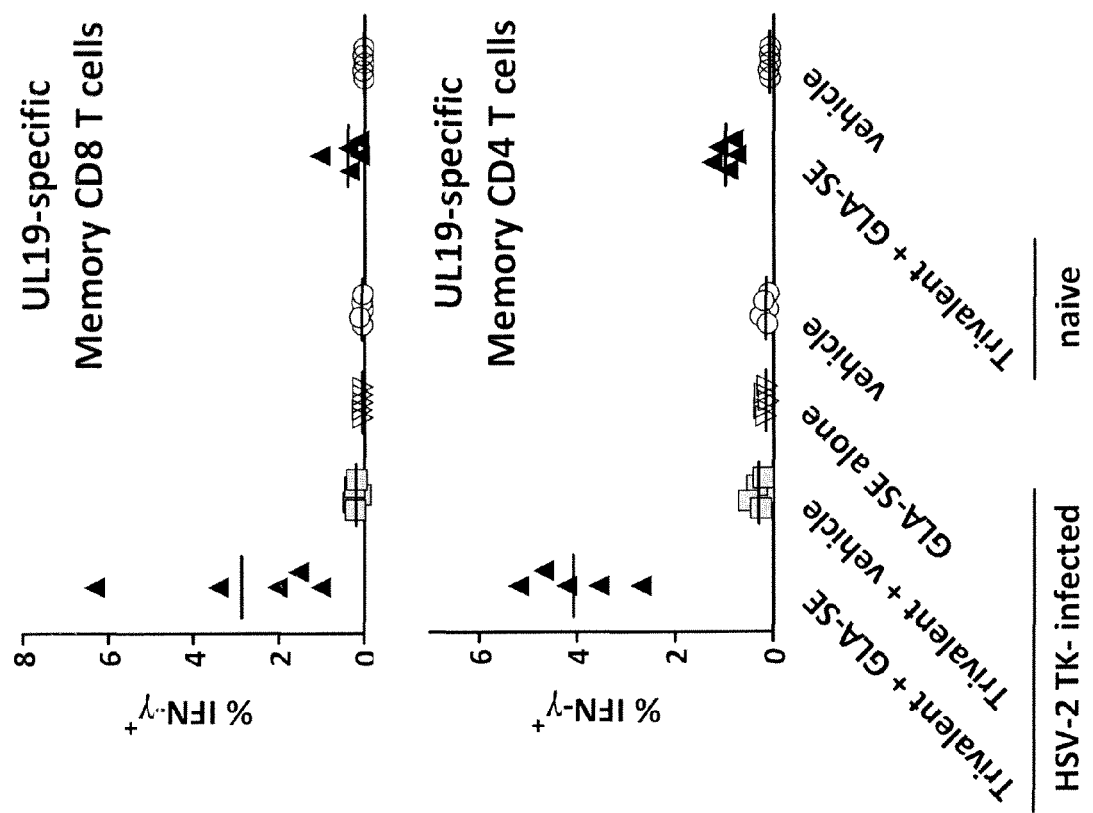
FIG. 13 shows data obtained when C57BL/6 mice (5/group) were infected subcutaneously with a sublethal dose of attenuated HSV-2 thymidine kinase-deficient (TK−) virus, then immunized 28 days later with a trivalent vaccine consisting of 5 µg each of recombinant gD2, UL19ud, and UL25 in combination with 5 µg GLA-SE or 5% dextrose vehicle. Control groups included infected mice treated with GLA-SE alone or vehicle alone, as well as naïve mice treated with vehicle alone. Six days post immunization, UL19-specific CD8 (upper panel) and CD4 (lower panel) T cell responses were measured by ICS after stimulation with UL19 peptides.

Groups of five C57BL/6 mice were infected subcutaneously with a sublethal dose of attenuated HSV-2 thymidine kinase-deficient (TK−) virus. 28 days later, infected or uninfected mice were immunized with a trivalent vaccine consisting of 5 μg each of recombinant gD2, UL19ud, and UL25 in combination with 5 μg GLA-SE or 5% dextrose vehicle. Control groups included infected mice treated with GLA-SE alone or vehicle alone, as well as naïve mice treated with vehicle alone. Six days post immunization, UL19-specific CD4 and CD8 T cell responses were measured by ICS. As depicted in FIG. 13, the frequency of UL19-specific CD4 and CD8 T cells was greater after immunization of previously infected mice, indicating that there was recall of infection-induced memory T cells. Importantly, maximum expansion of these memory T cells by recombinant protein vaccine required the presence of GLA-SE adjuvant.

Example 13

Ability of a Recombinant HSV-2 Protein Vaccine to Treat Recurrent HSV-2 in Guinea Pigs In this example, the ability of a trivalent recombinant HSV-2 protein vaccine to reduce the frequency of recurrent HSV-2 lesions is assessed.

Figure 14:
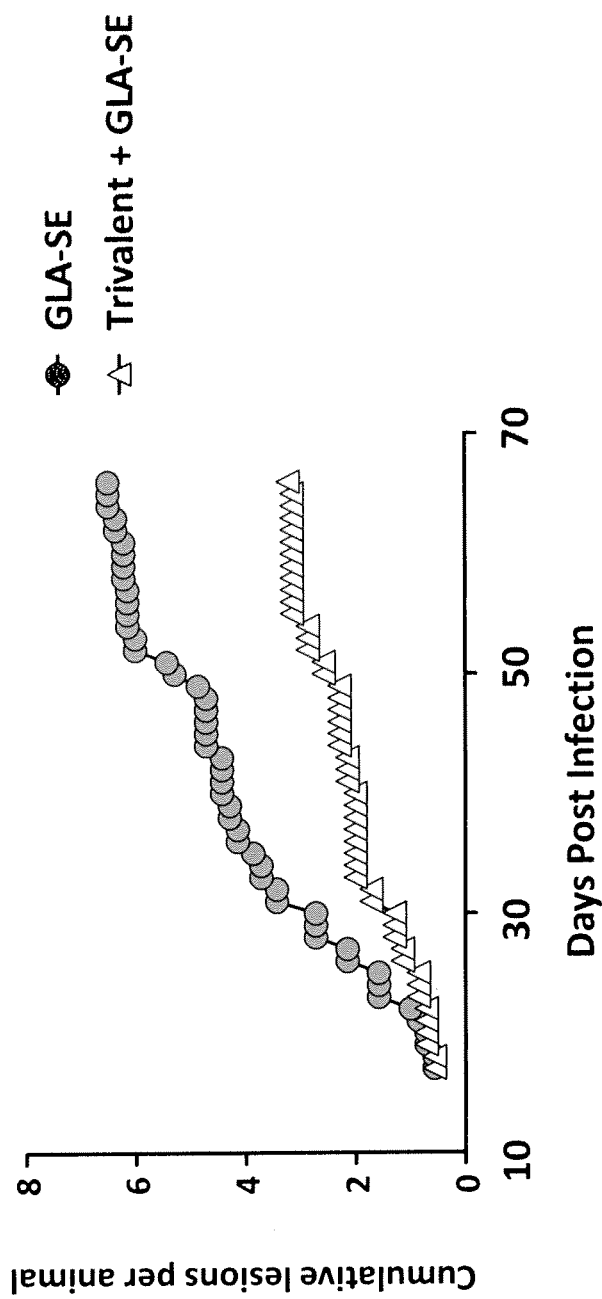
FIG. 14 shows data obtained when guinea pigs (7/group) were infected intravaginally with a sublethal dose of HSV-2 strain 333 virus and then treated on days 13 and 27 post infection with trivalent vaccine consisting of 5 µg each of recombinant gD2, UL19ud, and UL25 in combination with 5 µg GLA-SE. Infected guinea pigs treated with GLA-SE alone served as negative controls. Animals were monitored daily for vaginal lesions and scores of 0-4 were assigned for each lesion day. Daily lesions scores in each group were averaged and plotted versus time.

Groups of seven guinea pigs infected intravaginally with a sublethal dose of HSV-2 strain 333 virus. On days 13 and 27 post infection, guinea pigs were immunized with a trivalent vaccine consisting of 5 μg each of recombinant gD2, UL19ud, and UL25 in combination with 5 μg GLA-SE. Infected guinea pigs treated with GLA-SE alone served as negative controls. Animals were monitored daily for vaginal lesions and scores of 0-4 were assigned for each lesion day. Daily lesions scores in each group were averaged and plotted versus time. As depicted in FIG. 14, animals treated with trivalent vaccine plus GLA-SE had approximately a 50% reduction in recurrent lesions compared to animals treated with GLA-SE alone.

Example 14

Identification of Epitopes that React with Neutralizing Antibody

In this example, serum from mice immunized with HSV-2 or humans infected with HSV-2 is used to identify epitopes that react with the immune serum. Serum that contains neutralizing antibodies is pre-incubated with overlapping peptides of HSV-2 envelope glycoproteins and then assayed for its ability to inhibit infection of cells with HSV-2. A reduction of inhibition indicates that the peptide has an epitope that reacts with the neutralizing antibody.

Groups of five Balb/c mice are immunized via a prime/boost immunization regimen (d0 prime/d21 boost) with HSV-2. Mice are injected in rear footpads with 50 μL of culture medium containing nothing (mock) or 1×106 pfu of HSV-2. From days −1 to +20, mice receive 1 mg/mL acyclovir in drinking water to minimize pathogenesis of primary infection. Serum is obtained from blood samples drawn 7-10 days after the booster injection. Sera are prepared from peripheral blood samples collected from humans identified as sero-positive for HSV-2.

Sera are tested for HSV-2 specific antibodies and for neutralizing activity. Anti-HSV-2 antibodies are tested for by Western blotting or by ELISA (e.g., HerpeSelect ELISA, Focus Diagnostics, Cypress Calif.). For Western blotting, proteins from Vero cells infected with HSV-2 are separated by polyacrylamide gel electrophoresis and transferred to polyvinylidene difluoride (PVDF, Immobilon P, Millipore, Mass.) substrate. The PVDF substrate is blocked with 0.5% Tween 20 in PBS for 1 hr. Sera samples are diluted in PBS, 0.5% fetal bovine serum and incubated with the PVDF substrate overnight. The substrate is washed in PBS, 0.5% Tween® 20 and then either anti-human or anti-mouse antibody conjugated to peroxidase is added. A chemiluminescence substrate (e.g., ECL-WB detection system, Amersham, Ill.) is added and signal detected.

The neutralizing activity of HSV-specific antibodies is tested. Human or mouse sera are treated at 56° C. for 30 min to inactivate complement. Serial twofold dilutions of serum are prepared in DMEM containing 5% FBS and then mixed with an equal volume of HSV-2 virus adjusted to give 100 plaques per well in the absence of neutralizing antibody. The virus serum mixture is incubated for 1 h at 37° C., overlaid with medium, transferred to wells containing permissive cells, such as Vero cells, and further incubated at 37° C. for 24 h. Medium is removed and cells are washed with PBS. The cells are fixed with a 2:1 mixture of methanol and acetone, and then dried. Plaques are visualized with a cocktail of polyclonal antibodies to gD2, gB2, and gC2 using horseradish peroxidase-conjugated protein A, followed by addition of the substrate 4-chloro-1-naphthol. The neutralization titer is expressed as the dilution of serum that reduced the number of plaques by 50%.

Inhibition of antibody activity is measured by incubating a peptide with the serum sample containing neutralizing antibody prior to mixing the antibody with the virus. Peptide that binds to neutralizing antibody will result in an increase in the number of plaques.

Peptides are synthesized as a set of staggered peptides. Each peptide is staggered by four amino acids. Each peptide is 25 amino acids long, although shorter or longer peptides may be used.

Example 15

Construction of Immunogenic Protein Derived from HSV-2 Envelope Glycoprotein and Containing a Leader Sequence In this example, an immunogenic protein is constructed from gD2 sequence and comprises the gD2 leader sequence.

The leader sequence of gD2 is 40 amino acids long (residues 1-40 in SEQ ID No.: 1). A nucleotide sequence encoding a 100 amino acid fragment (residues 1-100) is inserted into an expression vector. Site-directed mutagenesis is used to change residues 38-42 from CysAlaLysTyr (SEQ ID NO: 16) to GlyLeuAlaVal (SEQ ID NO: 17) or other sequence that isn't cleaved during protein synthesis. CHO cells are transformed with the vector containing the altered sequence and gD2 protein is isolated. Alternatively, the nucleotide sequence is inserted into a baculovirus expression vector and protein isolated from Sf9 cells. Verification that the leader sequence is present is obtained by HPLC analysis.

Example 16

Construction of Immunogen Derived from HSV-2 Envelope Glycoprotein

In this example, an immunogenic protein is constructed, starting from gD2 sequence.

Peptides identified in Example 14 are used to construct an immunogen in various ways. In one method, individual peptides are synthesized with a Cys at the N-terminus and conjugated to KLH (keyhole limpet hemocyanin) by standard methods. In another method, nucleotide sequence encoding each of the peptides identified in example 14 is ligated together and inserted into an expression vector. The peptides may be from the same or different glycoproteins. The vector is used to transform eukaryotic cells and protein isolated. In yet another method, a nucleotide sequence encoding a fragment of at least 100 amino acids that encompasses one or more of the identified peptides is inserted into an expression vector, which is used to transform eukaryotic cells.

Example 17

Immunogenicity of Protein Derived from HSV-2 Glycoprotein

This example demonstrates the B cell-based immunogenicity against the individual recombinant proteins from Examples above following administration to mice.

The experimental strategy consists of using two groups of five C57BL/6 mice. One group is immunized via a prime/boost immunization regimen (d0 prime/d21 boost) with one of the immunogens described in Examples above in combination with 5.5 μg of GLA-SE adjuvant delivered intramuscularly in 100 μl (50 μl each leg). The second group is mock immunized with vehicle (PBS). The animals are sacrificed on day 4 post-boost for the harvesting of the spleens and peripheral blood (via cardiac puncture). The serum of each vaccinated and mock-vaccinated mouse is analyzed for the presence of antigen-specific antibodies against each of the recombinant protein immunogens by direct ELISA. Neutralizing assay as described above is performed as well.

Example 18

Mouse and Guinea Pig Challenge Models

Protective efficacy of a vaccine is demonstrated in mice by prevention of death and reduction of viral load following challenge with virulent HSV-2 virus. Groups of ten six to eight week old female Balb/c mice receive three intramuscular injections of vaccine at 0, 2, and 4 weeks, followed by viral challenge at 6 weeks using 50 times the LD50 ($3 \times 10^7$ pfu) of HSV-2 virus administered by vaginal inoculation. Following challenge, mice are inspected twice daily, assessed for clinical score, and euthanized if pre-morbid. On days 1, 3, and 5 after challenge, vaginal swabs are taken for measurement of viral load by quantitative real-time PCR analysis of HSV-2 DNA. Sera are collected prior to each vaccination, prior to viral challenge, and on day 14 following challenge in surviving animals. Neutralizing antibody titers and the ratio of antigen-specific IgG1/IgG2a titers are measured to correlate these responses with survival and vaginal DNA titers. Splenocytes from day 14 survivors are isolated for studies of T cell responses. Negative control groups, receiving injections lacking protein and adjuvant or injected with adjuvant alone, typically die within two weeks following viral challenge, while positive control groups, receiving the attenuated live HSV-2 vaccine typically survive viral challenge.

Therapeutic efficacy is demonstrated in HSV-2 infected guinea pigs as detected by a reduction in lesions and vaginal HSV-2 shedding following recovery from primary HSV-2 infection. Female Hartley guinea pigs are infected by rupturing the vaginal closure membrane with a calcium alginate-tipped swab followed by instillation of $1\times10^{5-7}$ pfu HSV-2 strain MS by plastic catheter. The animals are evaluated daily and the severity of the primary genital skin disease is quantified using an established lesion score-scale. Following resolution of the primary genital skin disease, animals (12/group) that experience clinically symptomatic infection are randomized to three groups that include the vaccine candidate (Group 1), the corresponding adjuvant minus antigen (Group 2), and vehicle control treated animals (Group 3). Beginning on day 15 after HSV-2 infection, all animals are examined daily for the presence of recurrent viral lesions on the perineum. In addition, daily vaginal swab samples are collected from all animals and stored frozen (−800 C) for DNA extraction and quantitative PCR analysis of viral DNA. On day 21 after HSV-2 infection, animals in Groups 1 and 2 are immunized by bilateral intramuscular injection in the rear legs. The animals receive a second immunization on day 42 post challenge. Daily swabbing and scoring continue until day 63 post challenge. The primary endpoints are the impact of immunization on the frequency of symptomatic recurrent lesions and on the frequency and magnitude of virus shedding into the genital tract. This is be measured as the percentage of days that animals are positive for HSV-2 DNA by PCR ("shedding rate") and the quantity of HSV-2 DNA shed, expressed as a cumulative copy number during the observation period.

Example 19

Safety and Immunogenicity of Vaccine in Humans

The safety and immunogenicity of immunogens described above formulated with GLA-SE, or SE alone may be tested in a Phase 1A/1B study design using HSV-2 seronegative subjects (target for prophylactic vaccine) and HSV-2 seropositive subjects (target for immunotherapeutic vaccine). The study design may follow that established by the HIV Vaccine Trials Network (HVTN), and has been used in 40 human HIV-1 phase IA vaccine trials in the last 10 years.

The design of these Phase 1A trials consists of a standardized format of 12 subjects per group (10 vaccine-2 placebo) and is based upon the ability to define a serious adverse event at a 15% prevalence. Vaccines that are not immunogenic (<2 of 10 subjects develop immunity) are also defined. In the HSV-2 Phase 1A study, subjects receive 3 i.m. immunizations of 1 μg or 2.5 μg GLA-SE at 4 week intervals. A total of 48 HSV seronegative and HSV-2 seropositive subjects (HSV-1 seropositive or HSV-1 seronegative) are immunized in the Phase 1A trial.

HSV-2 seronegative subjects are defined by Western Blot at Day 0. In addition to safety assessments, subjects on study may be monitored for a possible vaccine-induced HSV-2 specific immune humoral and cellular immune response, and frequency of recurrence of genital ulcers (HSV-2 seropositive subjects only). For the HSV-2 infected population, two pre-vaccination time points may be used to establish antibody to gD2. Cellular immunity to HSV-2 recombinant proteins may be assessed by IFN-γ ELISPOT and ICS assays, and gD2-specific humoral immunity by ELISA and neutralizing antibody assays.

From the foregoing it will be appreciated that, although specific embodiments have been described herein for purposes of illustration, various modifications may be made without deviating from the spirit and scope of the invention. Accordingly, the invention is not limited except as by the appended claims.

What is claimed is:

1. A method for treating an Herpes Simplex virus type 2 infection (HSV-2) in a subject, comprising administering to the subject an immunogenic pharmaceutical composition comprising, (i) (a) an immunogenic fragment of an Herpes Simplex virus type 2 (HSV-2) UL19 polypeptide wherein the immunogenic fragment of UL19 comprises the amino acid sequence set forth in SEQ ID NO:12, wherein the immunogenic fragment of (i)(a) lacks at least 75% of amino acids 1-450 of SEQ ID NO: 4 and lacks at least 75% of amino acids of 1055-1374 of SEQ ID NO: 4 or an immunogenic variant thereof that retains at least 90% amino acid identity over the full length of the immunogenic fragment, (b) glycoprotein D of HSV-2 (gD2), wherein the gD2 comprises the amino acid sequence set forth in SEQ ID NO:2 or 3, or an immunogenic fragment thereof comprising at least 15 contiguous amino acids of SEQ ID NO: 2 or 3, (c) and UL25, wherein the UL25 comprises the amino acid sequence set forth in SEQ ID NO:5 or an immunogenic fragment thereof comprising at least 15 contiguous amino acids of SEQ ID NO: 5; and (ii) Glucopyranosyl Lipid Adjuvant (GLA).

2. A method for generating an immune response to HSV-2 in a subject, comprising administering to the subject an immunogenic pharmaceutical composition comprising, (i) (a) an immunogenic fragment of an Herpes Simplex virus type 2 (HSV-2) UL19 polypeptide wherein the immunogenic fragment of UL19 comprises the amino acid sequence set forth in SEQ ID NO:12 , wherein the immunogenic fragment of (i)(a) lacks at least 75% of amino acids 1-450 of SEQ ID NO: 4 and lacks at least 75% of amino acids of 1055-1374 of SEQ ID NO: 4 or an immunogenic variant thereof that retains at least 90% amino acid identity over the full length of the immunogenic fragment, (b)glycoprotein D of HSV-2 (gD2), wherein the gD2 comprises the amino acid sequence set forth in SEQ ID NO:2 or 3, or an immunogenic fragment thereof comprising at least 15 contiguous amino acids of SEQ ID NO: 2 or 3, (c) and UL25, wherein the UL25 comprises the amino acid sequence set forth in SEQ ID NO:5 or an immunogenic fragment thereof comprising at least 15 contiguous amino acids of SEQ ID NO: 5; and (ii) Glucopyranosyl Lipid Adjuvant (GLA).

3. The method of claim 1, wherein the immunogenic fragment of an HSV-2 UL19 polypeptide has the amino acid sequence set forth in SEQ ID NO:12.

4. The method of claim 1, wherein the immunogenic pharmaceutical composition further comprises one or more HSV-2 proteins, or an immunogenic fragment thereof, selected from the group consisting of UL47, ICPO, UL46, UL39, UL7 and UL26.

5. The method of claim 1, wherein the GLA is in the form of an oil-in-water emulsion or is in an aqueous form.

6. The method of claim 1, wherein the immunogenic pharmaceutical composition further comprises a second adjuvant.

7. The method of claim 6, wherein the second adjuvant is selected from the group consisting of a TLR7 agonist, a TLR9 agonist, alum; an emulsion; a saponin; a cytokine; an unmethylated CpG dinucleotide; and a modified saponin.

8. The method of claim 6, wherein the second adjuvant is an oil-in-water emulsion.

9. The method of claim 2, wherein the immunogenic fragment of an HSV-2 UL19 polypeptide has the amino acid sequence set forth in SEQ ID NO:12.

10. The method of claim 2, wherein the immunogenic pharmaceutical composition further comprises one or more HSV-2 proteins, or an immunogenic fragment thereof, selected from the group consisting of UL47, ICP0, UL46, UL39, UL7 and UL26.

11. The method of claim 2, wherein the GLA is in the form of an oil-in-water emulsion or is in an aqueous form.

12. The method of claim 2, wherein the immunogenic pharmaceutical composition further comprises a second adjuvant.

13. The method of claim 12, wherein the second adjuvant is selected from the group consisting of a TLR7 agonist, a TLR9 agonist, alum; an emulsion; a saponin; a cytokine; an unmethylated CpG dinucleotide; and a modified saponin.

14. The method of claim 12, wherein the second adjuvant is an oil-in-water emulsion.

* * * * *